(12) United States Patent
Massberg et al.

(10) Patent No.: US 7,514,543 B2
(45) Date of Patent: Apr. 7, 2009

(54) POLYNUCLEOTIDES ENCODING IMMUNOADHESINS COMPRISING A GLYCOPROTEIN VI DOMAIN

(75) Inventors: Steffen Massberg, München (DE); Meinrad Gawaz, München (DE); Andreas Bültmann, München (DE); Götz Münch, München (DE); Martin Ungerer, München (DE); Mario Peluso, München (DE)

(73) Assignee: Trigen GmbH, Martinsried (DE)

( * ) Notice: Subject to any disclaimer, the term of this patent is extended or adjusted under 35 U.S.C. 154(b) by 340 days.

(21) Appl. No.: 10/489,053

(22) PCT Filed: Jun. 5, 2003

(86) PCT No.: PCT/EP03/05929

§ 371 (c)(1),
(2), (4) Date: Sep. 24, 2004

(87) PCT Pub. No.: WO03/104282

PCT Pub. Date: Dec. 18, 2003

(65) Prior Publication Data

US 2005/0079541 A1      Apr. 14, 2005

(30) Foreign Application Priority Data

Jun. 7, 2002    (EP) .................................. 02012742

(51) Int. Cl.
C07H 21/04    (2006.01)
(52) U.S. Cl. ..................................... 536/23.1; 435/326
(58) Field of Classification Search ........................ None
See application file for complete search history.

(56) References Cited

U.S. PATENT DOCUMENTS

| | | | |
|---|---|---|---|
| 5,116,964 A | 5/1992 | Capon et al. | |
| 5,156,840 A * | 10/1992 | Goers et al. | 540/145 |
| 5,525,491 A * | 6/1996 | Huston et al. | 435/69.7 |
| 6,245,527 B1 | 6/2001 | Busfield et al. | |
| 6,383,779 B1 | 5/2002 | Busfield et al. | 435/69.1 |
| 6,406,697 B1 | 6/2002 | Capon et al. | |
| 2004/0152628 A9 | 8/2004 | Tandon et al. | |
| 2004/0157300 A1 | 8/2004 | Burger et al. | |
| 2005/0142140 A1 | 6/2005 | Massberg et al. | |

FOREIGN PATENT DOCUMENTS

| | | |
|---|---|---|
| EP | 0 832 971 A1 | 4/1998 |
| EP | 0 383 799 B1 | 5/1998 |
| EP | 0 314 317 B1 | 8/1998 |
| EP | 1 224 942 A1 | 7/2002 |
| EP | 1 228 768 A1 | 8/2002 |
| EP | 1 369 128 A | 12/2003 |
| EP | 1 369 128 A1 | 12/2003 |
| EP | 1 538 165 A | 6/2005 |
| WO | WO 99/50281 A2 | 10/1999 |
| WO | WO 99/58572 A1 | 11/1999 |
| WO | WO 00/68377 A1 | 11/2000 |
| WO | WO 01/00810 | 1/2001 |
| WO | WO 01/00810 A1 | 1/2001 |
| WO | WO 01/00810 A1 | 1/2001 |
| WO | WO 0100810 A1 * | 1/2001 |
| WO | WO 01/16321 | 3/2001 |
| WO | WO 01/16321 A1 | 3/2001 |
| WO | WO 02/080968 A1 | 10/2002 |
| WO | WO 02/096926 A1 | 12/2002 |
| WO | WO 03/008454 A2 | 1/2003 |
| WO | WO 03/054020 A2 | 7/2003 |
| WO | WO 03/055516 A1 | 7/2003 |
| WO | WO 03/097875 A1 | 11/2003 |
| WO | WO 03/103662 A2 | 12/2003 |

OTHER PUBLICATIONS

European Search Report corresponding to Application No. 02012742.9 mailed Sep. 19, 2003.

International Search Report corresponding to Application No. PCT/EP03/05929 mailed Mar. 4, 2004.

Jandrot-Perrus et al., "Cloning, Characterization, and Functional Studies of Human and Mouse Glycoprotein VI: A Platelet-Specific Collagen Receptor from the Immunoglobulin Superfamily," *Blood*, 96(5):1798-1807(Sep. 1, 2000).

Massberg et al., "Platelet-Endothelial Cell Interactions During Ischemia/Reperfusion: The Role of P-Selectin," *Blood*, 92(2):507-515 (Jul. 15, 1998).

Nieswandt et al., "Glycoprotein VI but not α2β1 Integrin is Essential for Platelet Interaction with Collagen," *The EMBO Journal*, 20(9):2120-2130(2001).

Nieswandt et al., "Long-Term Antithrombotic Protection by In Vivo Depletion of Platelet Glycoprotein VI in Mice," *J. Exp. Med.*, 193(4):459-469 (Feb. 19, 2001).

Rosenfeld et al., "Animal Models of Spontaneous Plaque Rupture: The Holy Grail of Experimental Atherosclerosis Research," *Curr. Atheroscler. Rep.*, 4(3):238-242 (May 2002).

Vinik et al, "Platelet Dysfunction in Type 2 Diabetes," *Diabetes Care*, 24(8):1476-1485 (Aug. 2001).

(Continued)

*Primary Examiner*—Michael Szperka
(74) *Attorney, Agent, or Firm*—Sterne, Kessler, Goldstein & Fox P.L.L.C.

(57) ABSTRACT

The present invention provides a fusion protein comprising (a) the extracellular domain of glycoprotein VI or a variant thereof that is functional for binding to collagen and (b) the Fc domain of an immunoglobulin or a function-conservative part thereof, characterised by a polypeptide chain having an amino acid sequence as shown in FIG. 7 and whereby the fusion protein is obtainable by a process which provides the fusion protein in the form of a specific dimer.

11 Claims, 27 Drawing Sheets

OTHER PUBLICATIONS

Capon et al., "Designing CD4 immunoadhesins for AIDS therapy," *Nature* 337:525-531, 1989.

Clemetson et al., "The Platelet Collagen Receptor Glycoprotein VI is a Member of the Immunoglobulin Superfamily Closely Related to FcαR and the Natural Killer Receptors," *The Journal of Biological Chemistry* 274(41):29019-29024, 1999.

Ezumi et al., "Molecular Cloning, Genomic Structure, Chromosomal Localization, and Alternative Splice Forms of the Platelet Collagen Receptor Glycoprotein VI," *Biochemical and Biophysical Research Communication* 277:27-36, 2000.

Gibbins et al., "Glycoprotein VI is the collagen receptor in platelets which underlies tyrosine phosphorylation of the Fc receptor γ-chain," *FEBS Letters* 413:255-259, 1997.

Grüner et al., "Relative antithrombotic effect of soluble GPVI dimer versus anti-GPVI antibodies in mice," *Blood First Edition Paper*, prepublished online Oct. 26, 2004, pp. 1-29.

Jandrot-Perrus et al., "Adhesion and Activation of Human Platelets Induced by Convulxin Involve Glycoprotein VI and Integrin $\alpha_2\beta_1$," *The Journal of Biological Chemistry* 272(43):27035-27041, 1997.

Jandrot-Perrus et al., "Cloning, characterization, and functional studies of human and mouse glycoprotein VI: a platelet-specific collagen receptor from the immunoglobulin superfamily," *Blood* 96(5):1798-1807, 2000.

Joutsi-Korhonen et al., "The low-frequency allele of the platelet collagen signaling receptor glycoprotein VI is associated with reduced functional responses and expressions," *Blood* 101(11):4372-4379, 2003.

Massberg et al., "Platelet-Endothelial Cell Interactions During Ischemia/Reperfusion: The Role of P-Selectin," *Blood* 92(2)507-515, 1998.

Massberg et al., "Soluble glycoprotein VI dimer inhibits platelet adhesion and aggregation to the injured vessel wall in vivo," *The FASEB Journal Express Article*, published online Dec. 4, 2003.

Massberg et al., "Soluble glycoprotein VI dimer inhibits platelet adhesion and aggregation to the injured vessel wall in vivo," *The FASEB Journal* 18:397-399, 2004.

Massberg et al., "Effects of a dimeric, soluble form of glycoprotein VI on platelet adhesion following vascular injury in vivo," *ESC Congress 2004*, Munich, Germany, Sep. 26, 2004 (Abstract only).

Miura et al., "Analysis of the Interaction of Platelet Collagen Receptor Glycoprotein VI (GPVI) with Collagen," *The Journal of Biological Chemistry* 277(38):46197-46204, 2002.

Moroi et al., "A new monoclonal antibody, mAb 204-11, that influences the binding of platelet GPVI to fibrous collagen," *Thromb Haemost* 89:996-1003, 2003.

Nieswandt et al., "Glycoprotein VI but not α2β1 integrin is essential for platelet interaction with collagen," *The EMBO Journal* 20(9):2120-2130, 2001.

Nieswandt et al., "Long-term Antithrombotic Protection by In Vivo Depletion of Platelet Glycoprotein VI in Mice," *J. Exp. Med.* 193(4):459-469, 2001.

Rosenfeld et al., "Animal Models of Spontaneous Plaque Rupture: The Holy Grail of Experimental Atherosclerosis Research," *Current Atherosclerosis Reports* 4:238-242, 2002.

Vinik et al., "Platelet Dysfunction in Type 2 Diabetes," *Diabetes Care* 24(8):1476-141485, 2001.

Vinik et al., "Diabetes and macrovascular disease," *Journal of Diabetes and Its Complications* 16:235-24, 2002.

GenBank Accession No. AB043819 including UniGene Cluster No. Hs.272216, Nov. 2, 2000.

GenBank Accession No. AX046772, Dec. 15, 2000.

Robinson and Sauer, "Optimizing the stability of single-chain proteins by linker length and composition mutagenesis," *Proc. Natl. Acad. Sci. USA*, vol. 95, pp. 5929-5934, May 1998.

Chamow and Ashkenazi eds., *Antibody Fusion Proteins*, Wiley-Liss, Inc., New York 1999, 312 pp.

Goto et al., "Involvement of Glycoprotein VI in Platelet Thrombus Formation of Both Collagen and von Willebrand Factor Surfaces Under Flow Conditions," *Circulation* 106:266-272, 2002 (Online Publication Jun. 17, 2002).

Konishi et al., "Platelets Activated by Collagen Through Immunoreceptor Tyrosine-Based Activation Motif Play Pivotal Role in Initition and Generation of Neointimal Hyperplasia After Vascular Injury," *Circulation* 105:912-916, 2002.

Massberg, S., "Glycoprotein VI—platelet adhesion molecule and therapeutic target," *Gesellschaft fur Mikrozirkulation und Vaskulare Biologie e.V. Annual Meeting 2004*, Berlin, *Final Program* p. 29, Oct. 8, 2004, Abstract Only.

Nieswandt and Watson, "Platelet-collagen interaction: is GPVI the central receptor?" *Blood* 102(2):449-461, Jul. 15, 2003.

Lecut et al., "Inhibition of Platelet-Collagen Interactions by Specific Anti-Human GPVI Monoclonal Antibodies," *Supplement J. Thrombosis and Haemostasis* Jul. 2001 Abstract Only.

Lecut et al., "Identification of Residues within Human Glycoprotein VI Involved in the Binding to Collagen," *J. Biological Chemistry* 279(5):52293-52299, 2004.

Penz et al., "Human atheromatous plaques stimulate thrombus formation by activating platelet glycoprotein VI," *FASEB J.* 19:898-909, 2005.

Smethurst et al., "Identification of the primary collagen-binding surface on human glycoprotein VI by site-directed mutagenesis and by a blocking phage antibody," *Blood* 103(3):903-911, Feb. 1, 2004.

International Search Report issued in PCT Patent Application No. PCT/EP2006/062908, dated Feb. 21, 2007.

Aruffo, A., "Immunoglobulin Fusion Proteins," in *Antibody Fusion Proteins*, Chamow, S.M., and Ashkenazi, A., eds., Wiley-Liss, Inc., New York, NY, pp. 221-241 (1999).

Croft, S.A., et al., "Novel Platelet Membrane Glycoprotein VI Dimorphism Is a Risk Factor for Myocardial Infarction," *Circulation 104*: 1459-1463, American Heart Association (Sep. 2001).

Moroi, M., et al., "A Patient with Platelets Deficient in Glycoprotein VI That Lack Both Collagen-induced Aggregation and Adhesion," *J. Clin. Invest. 84*:1440-1445, American Society for Clinical Investigation (1989).

Morton, L.F., et al., "Platelet Aggregation By a Collagen-Like Synthetic Peptide," *Thromb. Res. 72*:367-372, Pergamon Press (1993).

Robinson, C.R. and Sauer, R.T., "Optimizing the stability of single-chain proteins by linker length and composition mutagenesis," *Proc. Natl. Acad. Sci. U.S.A. 95*:5929-5934, National Academy of Sciences (1998).

Skolnick, J. and Fetrow, J.S., "From genes to protein structure and function: novel applications of computational approaches in the genomic era," *Trends Biotechnol. 18*:34-39, Elsevier Science Publishers (2000).

Sugiyama, T., et al., "A Novel Platelet Aggregating Factor Found in a Patient With Defective Collagen-Induced Platelet Aggregation and Autoimmune Thrombocytopenia," *Blood 69*:1712-1720, American Society of Hematology (1987).

Whisstock, J.C. and Lesk, A.M., "Prediction of protein function from protein sequence and structure," *Q. Rev. Biophys. 36*:307-340, Cambridge University Press (Aug. 2003).

Office Action for U.S. Appl. No. 11/009,106, Massberg, S., filed Dec. 10, 2004, mailed on Oct. 12, 2007.

\* cited by examiner

Fig. 1c
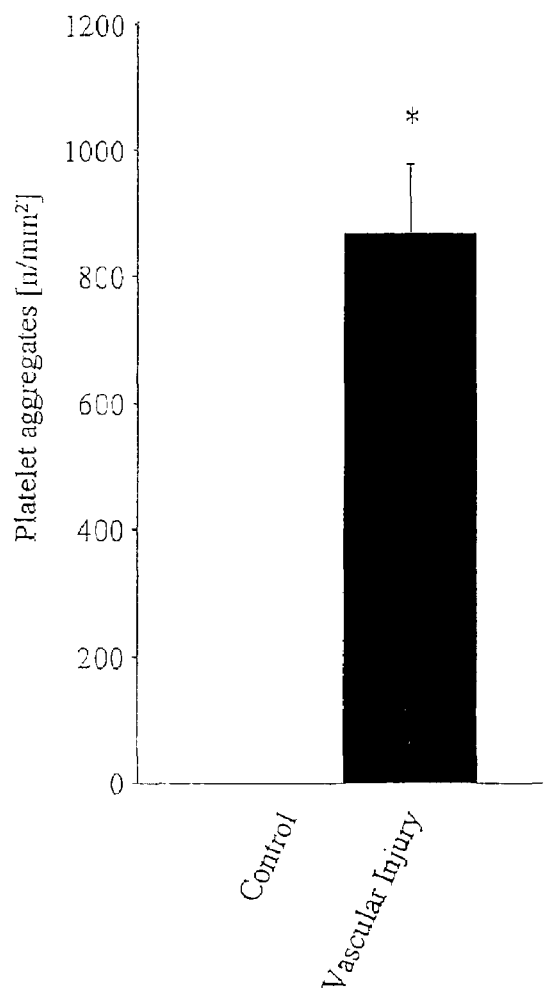
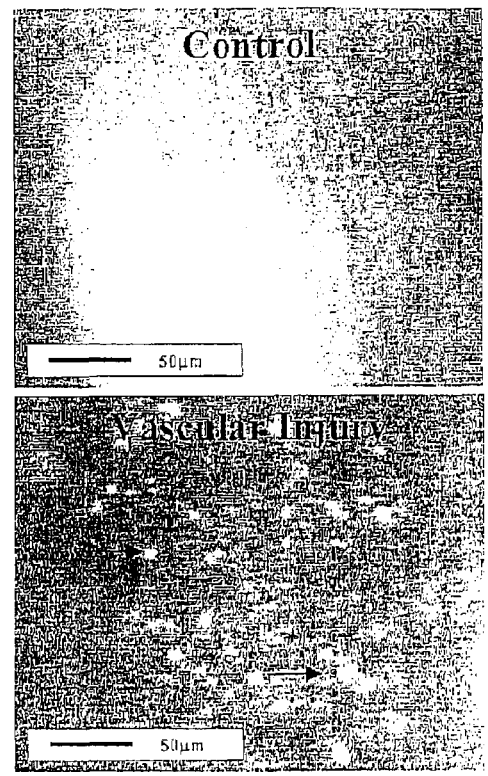

```
  1  MSPSPTALFC LGLCLGRVPA QSGPLPKPSL QALPSSLVPL EKPVTLRCQG
 51  PPGVDLYRLE KLSSSRYQDQ AVLFIPAMKR SLAGRYRCSY QNGSLWSLPS
101  DQLELVATGV FAKPSLSAQP GPAVSSGGDV TLQCQTRYGF DQFALYKEGD
151  PAPYKNPERW YRASFPIITV TAAHSGTYRC YSFSSRDPYL WSAPSDPLEL
201  VVTGTSVTPS RLPTEPPSSV AEFSEATAEL TVSFTNKVFT TETSRSITTS
251  PKESDSPAGP ARQYYTKGNG GRESKSCDKT HTCPPCPAPE LLGGPSVFLF
301  PPKPKDTLMI SRTPEVTCVV VDVSHEDPEV KFNWYVDGVE VHNAKTKPRE
351  EQYNSTYRVV SVLTVLHQDW LNGKEYKCKV SNKALPAPIE KTISKAKGQP
401  REPQVYTLPP SRDELTKNQV SLTCLVKGFY PSDIAVEWES NGQPENNYKT
451  TPPVLDSDGS FFLYSKLTVD KSRWQQGNVF SCSVMHEALH NHYTQKSLSL
501  SPGK*
```

Fig. 7

```
   1 ATGTCTCCAT CCCCGACCGC CCTCTTCTGT CTTGGGCTGT GTCTGGGGCG
  51 TGTGCCAGCG CAGAGTGGAC CGCTCCCCAA GCCCTCCCTC CAGGCTCTGC
 101 CCAGCTCCCT GGTGCCCCTG GAGAAGCCAG TGACCCTCCG GTGCCAGGGA
 151 CCTCCGGGCG TGGACCTGTA CCGCCTGGAG AAGCTGAGTT CCAGCAGGTA
 201 CCAGGATCAG GCAGTCCTCT TCATCCCGGC CATGAAGAGA AGTCTGGCTG
 251 GACGCTACCG CTGCTCCTAC CAGAACGGAA GCCTCTGGTC CCTGCCCAGC
 301 GACCAGCTGG AGCTCGTTGC CACGGGAGTT TTTGCCAAAC CCTCGCTCTC
 351 AGCCCAGCCC GGCCCGGCGG TGTCGTCAGG AGGGGACGTA ACCCTACAGT
 401 GTCAGACTCG GTATGGCTTT GACCAATTTG CTCTGTACAA GGAAGGGGAC
 451 CCTGCGCCCT ACAAGAATCC CGAGAGATGG TACCGGGCTA GTTTCCCCAT
 501 CATCACGGTG ACCGCCGCCC ACAGCGGAAC CTACCGATGC TACAGCTTCT
 551 CCAGCAGGGA CCCATACCTG TGGTCGGCCC CCAGCGACCC CCTGGAGCTT
 601 GTGGTCACAG GAACCTCTGT GACCCCCAGC CGGTTACCAA CAGAACCACC
 651 TTCCTCGGTA GCAGAATTCT CAGAAGCCAC CGCTGAACTG ACCGTCTCAT
 701 TCACAAACAA AGTCTTCACA ACTGAGACTT CTAGGAGTAT CACCACCAGT
 751 CCAAAGGAGT CAGACTCTCC AGCTGGTCCT GCCCGCCAGT ACTACACCAA
 801 GGGCAACGGC GGCCGCGAGT CCAAATCTTG TGACAAAACT CACACATGCC
 851 CACCGTGCCC AGCACCTGAA CTCCTGGGGG GACCGTCAGT CTTCCTCTTC
 901 CCCCCAAAAC CCAAGGACAC CCTCATGATC TCCCGGACCC CTGAGGTCAC
 951 ATGCGTGGTG GTGGACGTGA GCCACGAAGA CCCTGAGGTC AAGTTCAACT
1001 GGTACGTGGA CGGCGTGGAG GTGCATAATG CCAAGACAAA GCCGCGGGAG
1051 GAGCAGTACA ACAGCACGTA CCGTGTGGTC AGCGTCCTCA CCGTCCTGCA
1101 CCAGGACTGG CTGAATGGCA AGGAGTACAA GTGCAAGGTC TCCAACAAAG
1151 CCCTCCCAGC CCCCATCGAG AAAACCATCT CCAAAGCCAA AGGGCAGCCC
1201 CGAGAGCCAC AGGTGTACAC CCTGCCCCCA TCCCGGGATG AGCTGACCAA
1251 GAACCAGGTC AGCCTGACCT GCCTGGTCAA AGGCTTCTAT CCCAGCGACA
1301 TCGCCGTGGA GTGGGAGAGC AATGGGCAGC CGGAGAACAA CTACAAGACC
1351 ACGCCTCCCG TGCTGGACTC CGACGGCTCC TTCTTCCTCT ACAGCAAGCT
1401 CACCGTGGAC AAGAGCAGGT GGCAGCAGGG GAACGTCTTC TCATGCTCCG
1451 TGATGCATGA GGCTCTGCAC AACCACTACA CGCAGAAGAG CCTCTCCCTG
1501 TCTCCGGGTA AATGA
```

Fig. 8

Figure 9
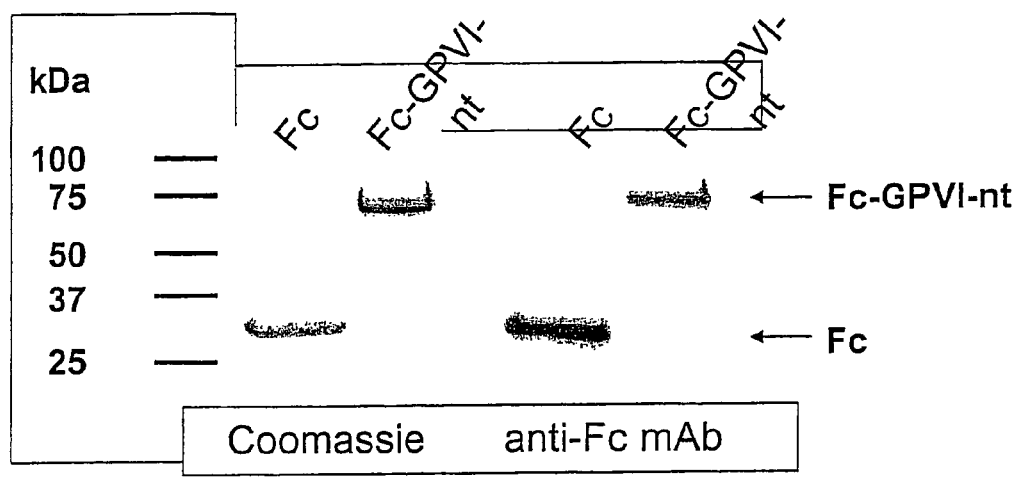
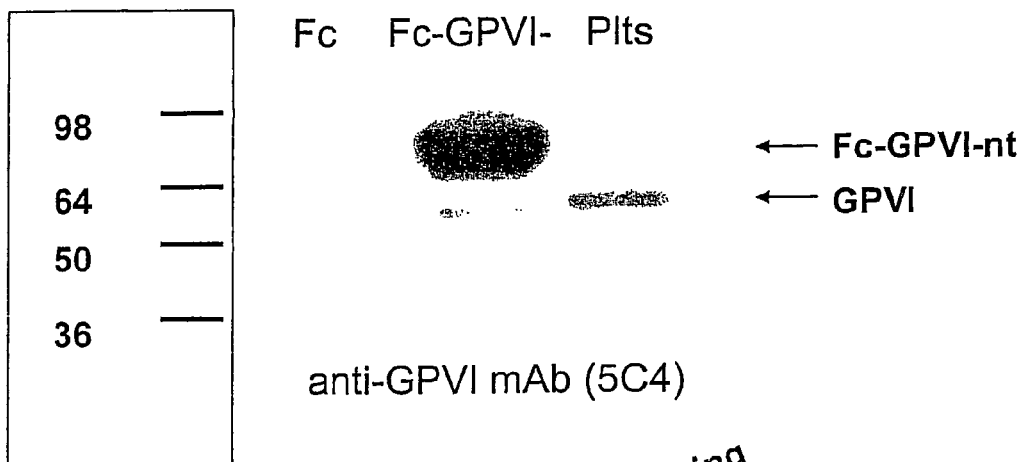
Coomassie Stain

*Figure 9 (continued)*
b
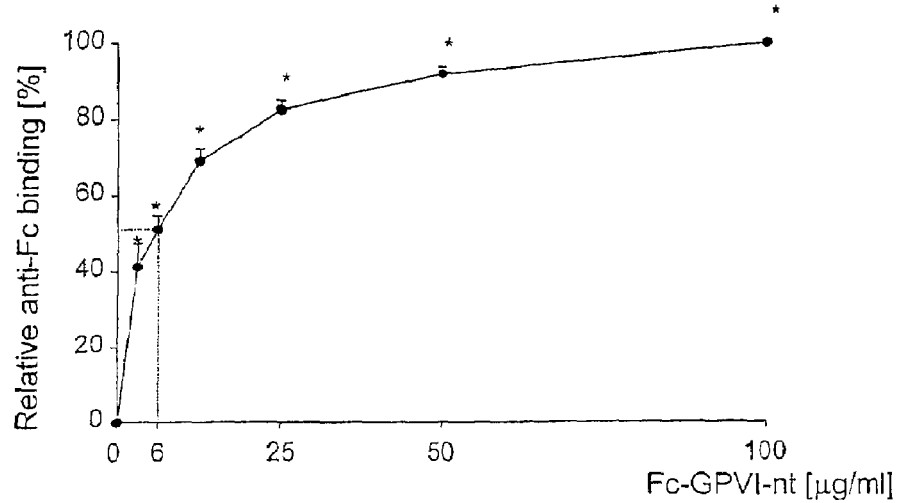
c
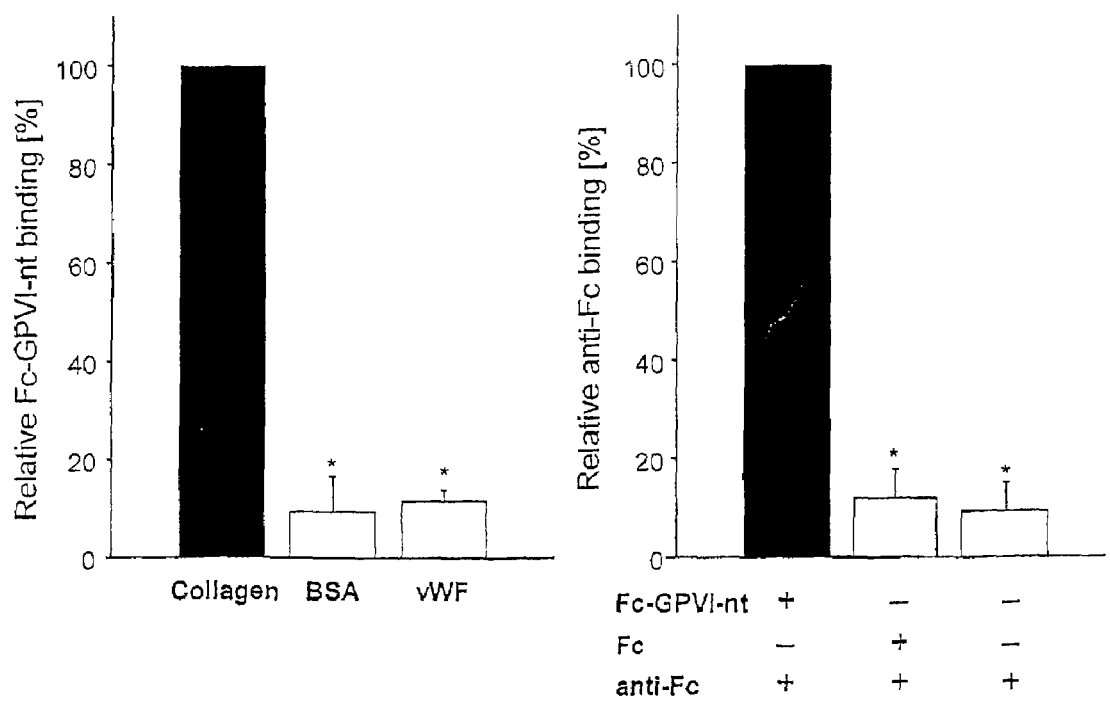

*Figure 9 (continued)*
d
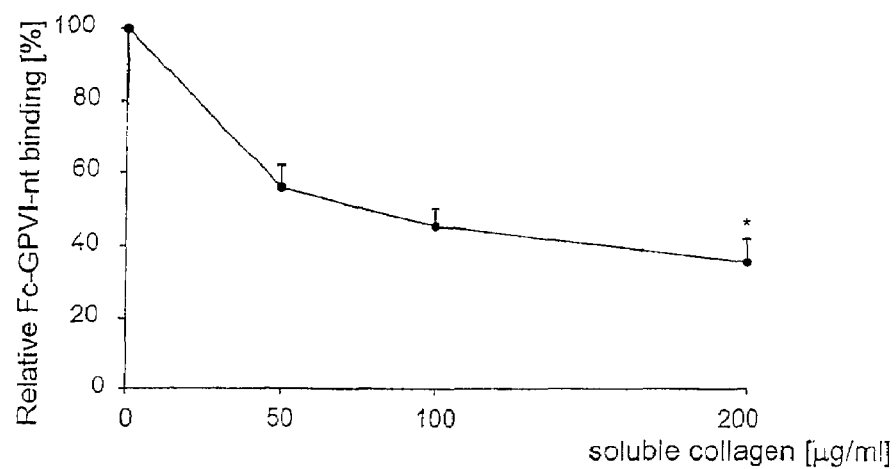
e
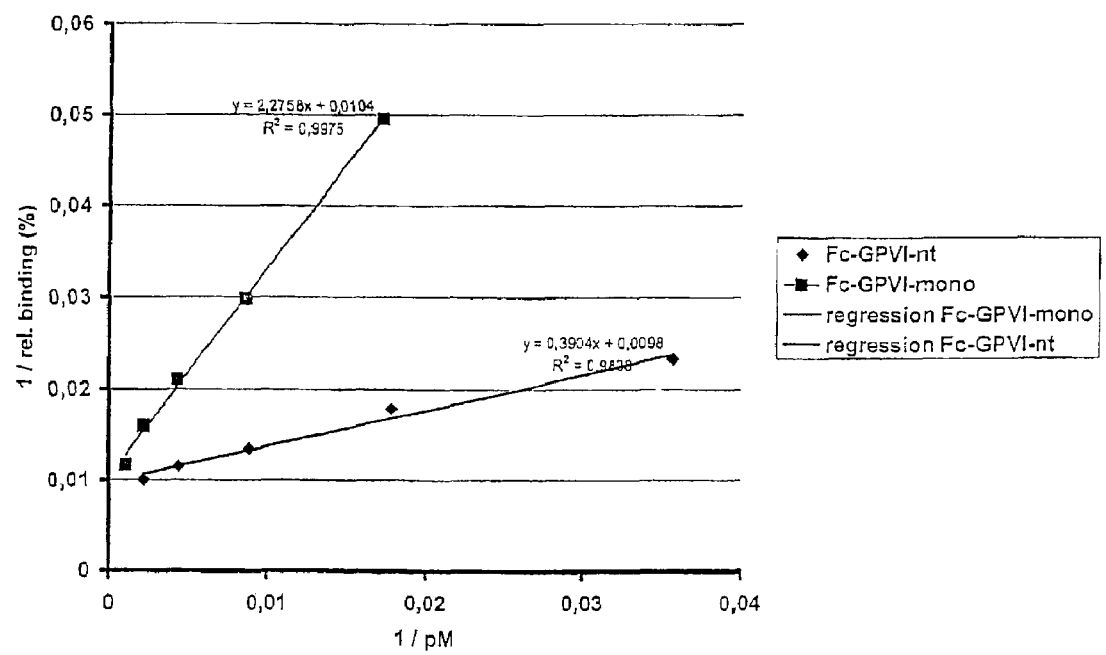

Figure 11  Platelet aggregation
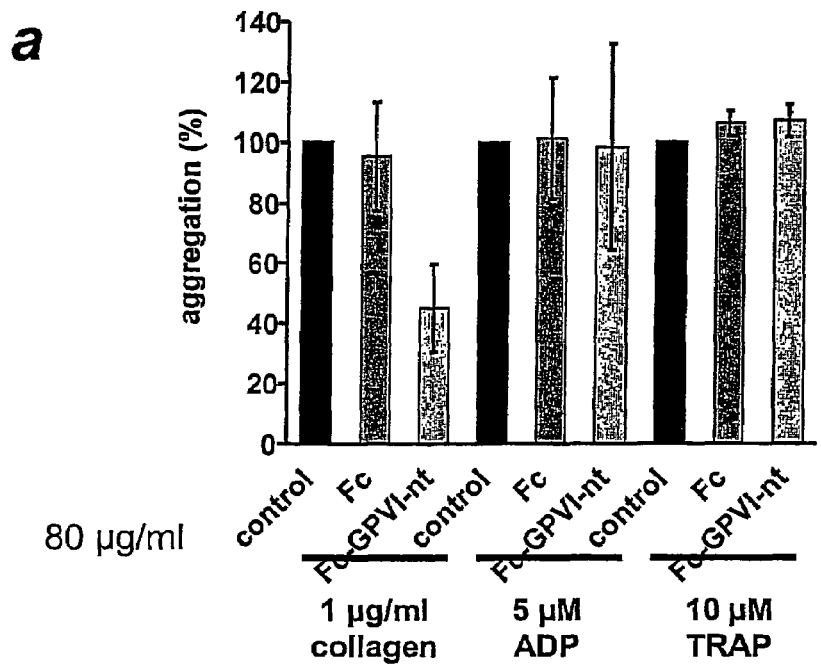
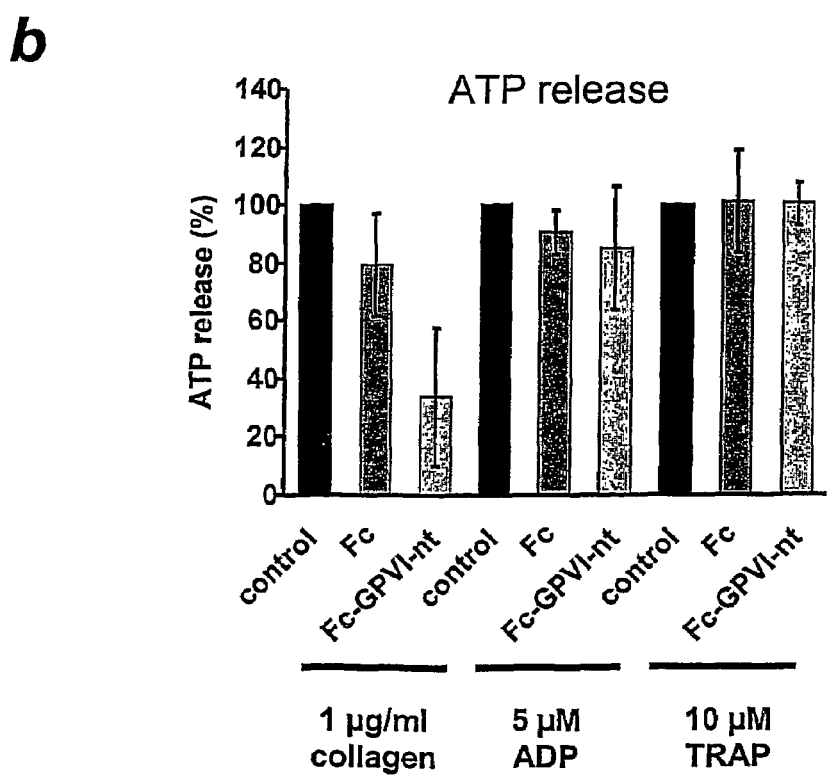

C

Figure 13
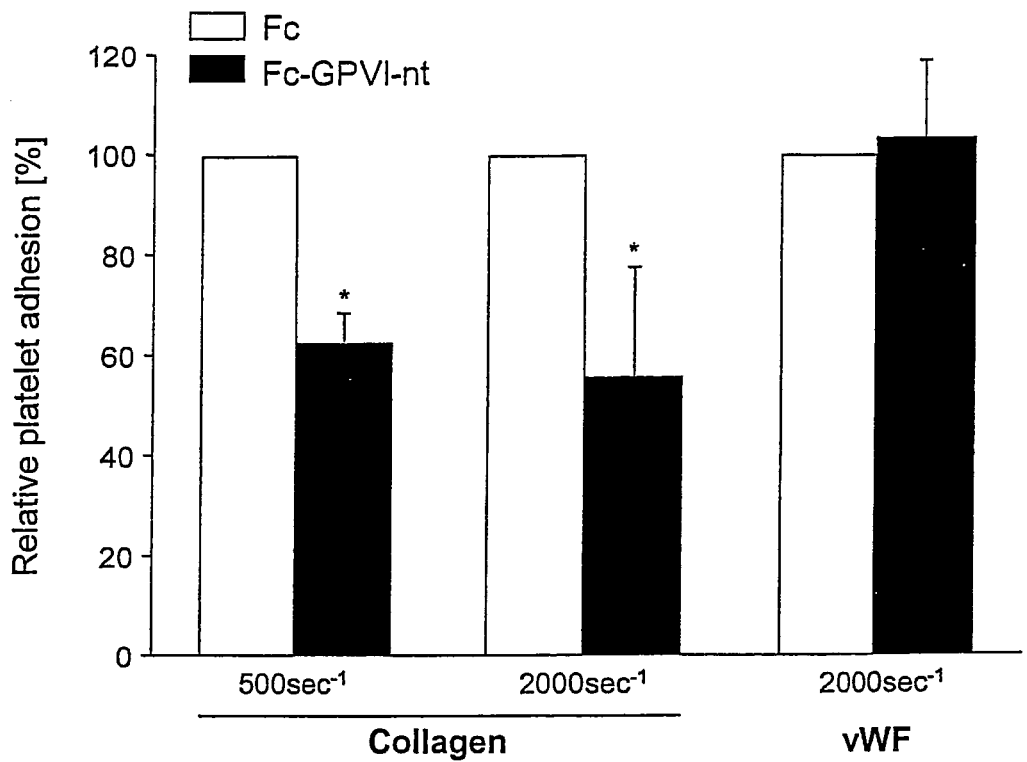
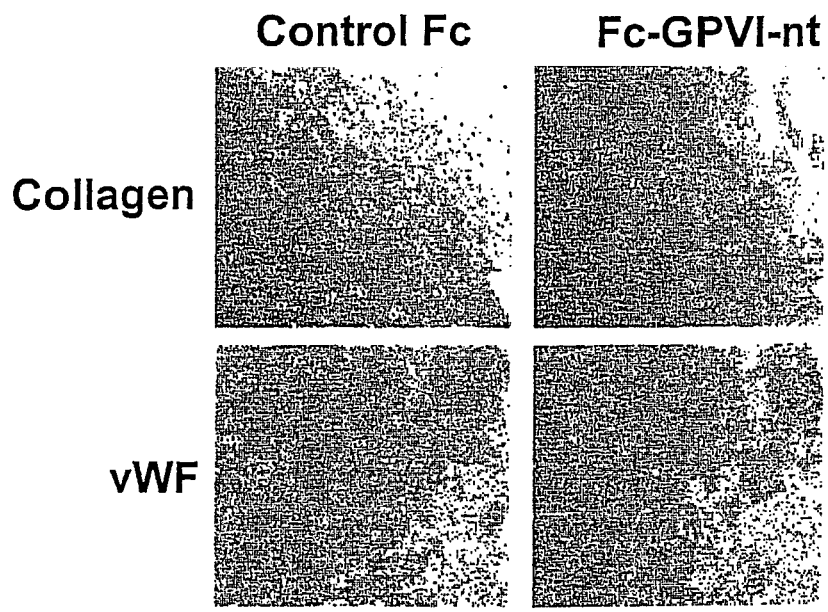

Figure 14
a
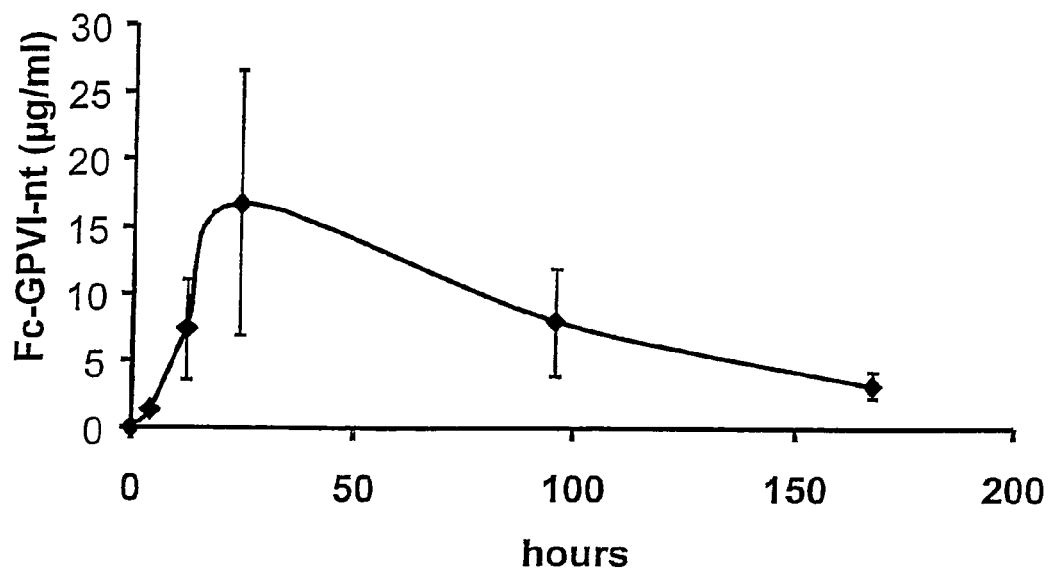
Fc-GPVI-nt Pharmacokinetic single dose
b
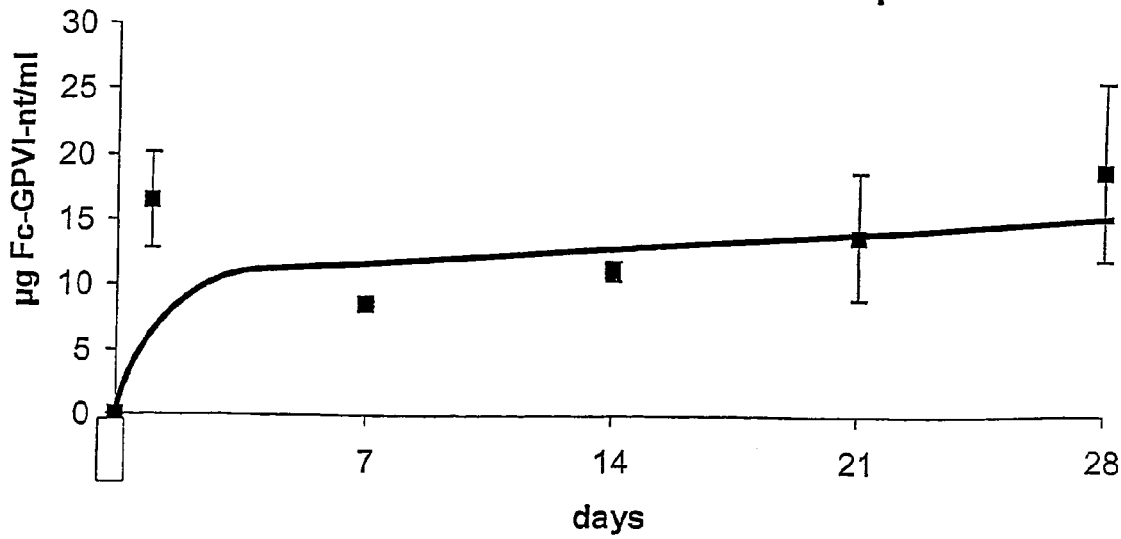
Fc-GPVI-nt Pharmacokinetic repeated dose

C a

*Figure 15 (continued)*
b
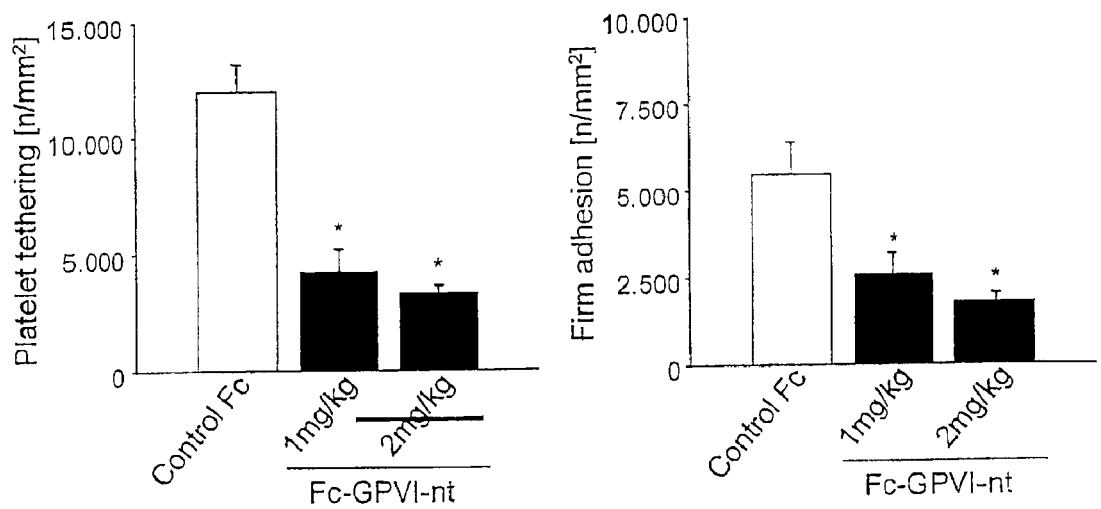
c
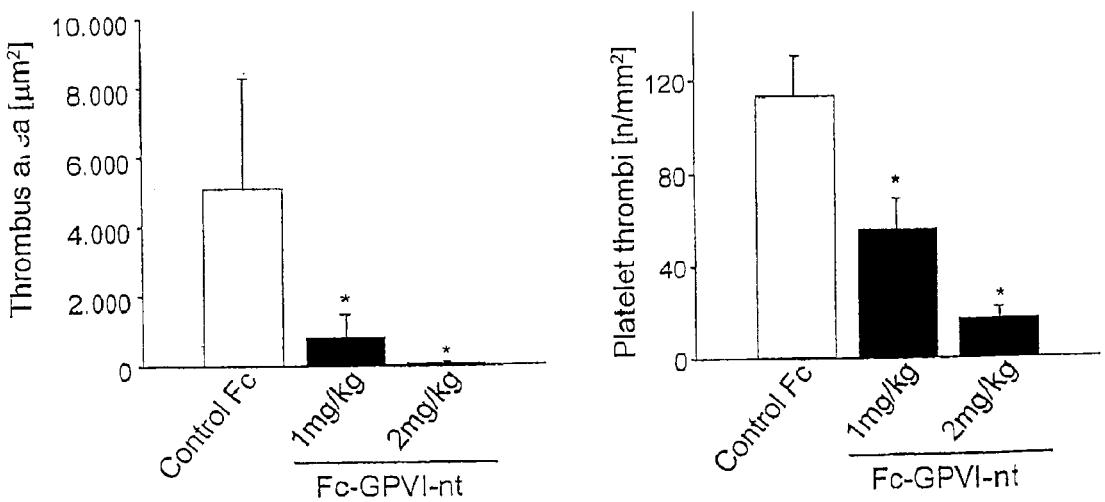

d

Figure 15 (continued)
e
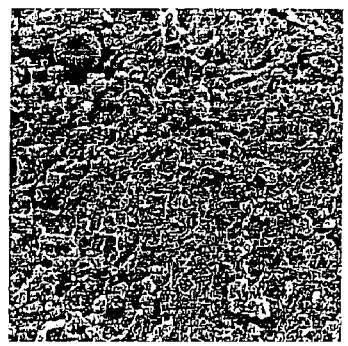
Fc
Fc-GPVI-nt
f
Fc
Fc-GPVI-nt
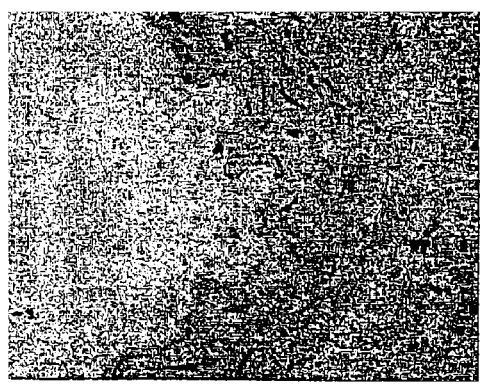

Figure 16
Fc-GPVI-nt
Fc

Figure 17
CD61 Expression on Human Platelets
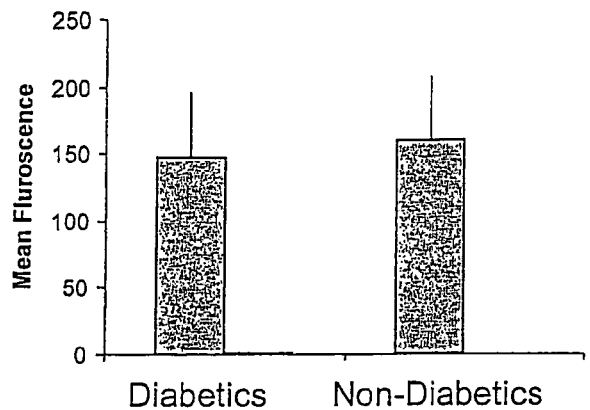
CD 32 Receptor Expression on human Platelets
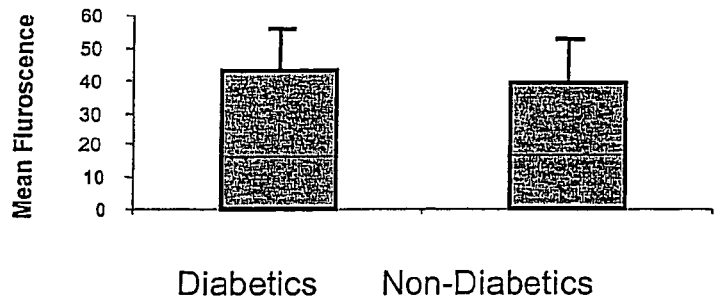
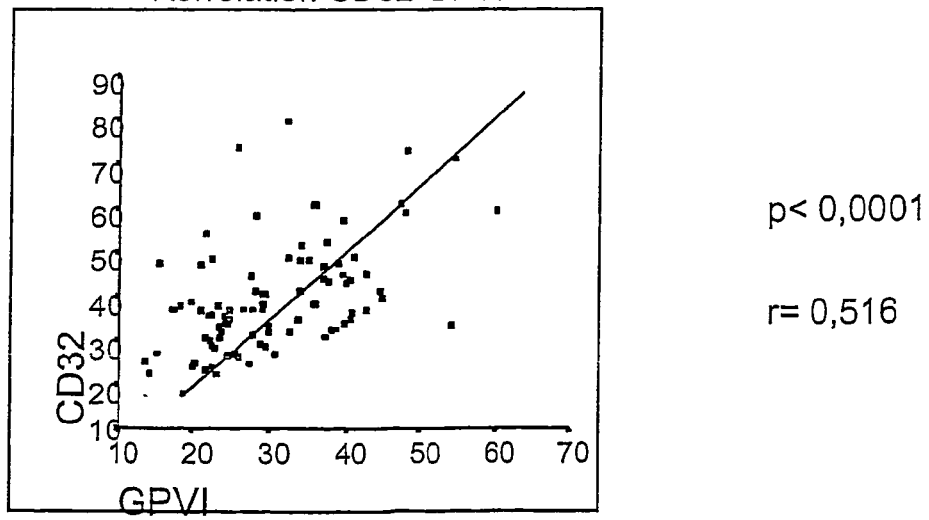
$p < 0{,}0001$
$r = 0{,}516$

Figure 18

MSPSPTALFCLGLCLGRVPAQSGPLPKPSLQALPSSLVPLEKPVTLRCQGPPGVDLYRLEKLSSSRYQDQ
AVLFIPAMKRSLAGRYRCSYQNGSLWSLPSDQLELVATGVFAKPSLSAQPGPAVSSGGDVTLQCQTRYG
FDQFALYKEGDPAPYKNPERWYRASFPIITVTAAHSGTYRCYSFSSRDPYLWSAPSDPLELVVTGTSVTP
SRLPTEPPSSVAEFSEATAELTVSFTNKVFTTETSRSITTSPKESDSPAGPARQYYTKGN*GGRP*APELLGG
PSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEALHNHYTQKSLSLSPG
K

US 7,514,543 B2

POLYNUCLEOTIDES ENCODING IMMUNOADHESINS COMPRISING A GLYCOPROTEIN VI DOMAIN

CROSS-REFERENCE TO RELATED APPLICATIONS

The present application is a 35 U.S.C. § 371 National Phase Application of International Application Serial No. PCT/EP02/05929, filed Jun. 5, 2003 and published in English as PCT Publication No. WO 03/104282 on Dec. 18, 2003, which claims priority to European Patent Application Serial No. EP 02 012 742.9, filed Jun. 7, 2002, the disclosures of each of which are incorporated herein by reference in their entireties.

The present invention relates to an immunoadhesin comprising a specific glycoprotein VI domain. The immunoadhesin of the invention is obtainable by a specific process providing the immunoadhesin in the form of a dimer. The present invention also relates to the use of the immunoadhesin of glycoprotein VI for the preparation of a medicament for the prevention of intraarterial thrombosis in a specific group of patients. Moreover, the present invention relates to the the use of the immunoadhesin of glycoprotein VI for the preparation of a medicament for the prevention and treatment of atheroprogression. The present invention also relates to the use of the immunoadhesin of glycoprotein VI for the preparation of a medicament for the prevention and treatment of chronic progression of atherosclerosis in diabetic patients. The present invention also relates to in vitro and in vivo screening methods for an Inhibitor of GPVI mediated adhesion of platelets to active intravascular lesions.

Acute coronary or carotid syndromes are a major cause of death in Western societies. Even in case of an initial survival of such a cardiovascular event, many patients suffer from life-threatening complications such as intravascular thrombosis leading to further myocardial infarction or stroke.

Intravascular thrombosis is the result of aggregation of platelets in a vessel whereby the blood flow in the vessel may be seriously reduced or even completely inhibited. Specifically, the disruption of an atherosclerotic plaque initiates a cascade of events culminating in arterial thrombosis and ischemia of the downstream tissue, precipitating diseases such as myocardial infarction or ischemic stroke. The first response to vascular injury is adhesion of circulating platelets to exposed subendothelial matrix proteins, which triggers subsequent platelet aggregation. Among the macromolecular components of the subendothelial layer fibrillar collagen is considered the most thrombogenic constituent, as it acts as a strong activator of platelets and supports platelet adhesion both in vitro and in vivo (1-3).

The platelet membrane proteins, which have been reported to be putative collagen receptors, may be divided into those which interact indirectly with collagen through collagen-bound von Willebrand factor (vWf), including GPIbα and the integrin $\alpha_{IIb}\beta_3$, and those which interact directly with collagen including GPVI, the integrin $\alpha_2\beta_1$, and CD36 (reviewed in (2)). Only recently, the platelet glycoprotein VI (GPVI) has been identified as the major platelet collagen receptor (4). GPVI is a 60-65 kDa type I transmembrane glycoprotein, which belongs to the immunoglobulin superfamily (5;6). In human and mouse platelets GPVI forms a complex with the FcR γ-chain at the cell surface (7;8). Ligand binding to GPVI triggers tyrosine phosphorylation of the ITAM motif of the Fc receptor g chain initiating downstream signaling via Syk kinases, LAT, SLP-76, and phospholipase C (9-13). Platelets deficient in GPVI show loss of collagen-induced adhesion and aggregation in vitro (4;14). Likewise, function blocking anti-GPVI monoclonal antibodies attenuate ex vivo platelet aggregation in response to collagen and collagen-related peptide CRP, which mimics collagen triple helix (15;16).

It is known that the problem of complications due to the aggregation of platelets can be addressed by administering inhibitors of platelet aggregation. For the treatment of acute coronary syndromes, GP IIb/IIIa inhibitors such as ReoPro significantly improve the outcome of patients. However, a recent meta-analysis of clinical trials revealed a significant remaining risk for death or myocardial infarction despite optimal antithrombotic intervention (Boersma E, Harrington R A, Moliterno D J, White H, Therouxi P, Van de Werf F, de Torbal A, Armstrong P W, Wallentin L C, Wilcox R G, Simes J, Califf R M, Topol E J, Simoons M L. Platelet glycoprotein IIb/IIIa inhibitors in acute coronary syndromes: a meta-analysis of all major randomised clinical trials. Lancet 2002; 359:189-98). Specific severe side effects of this therapeutic regimen are bleeding complications. These occurred in 2.4% of the patients with the most severe form of intracranial bleeding occuring in almost 0.1% of the treated patients. Several mechanistic shortcomings of the GP IIb/IIIa receptor blockade have been revealed which account for suboptimal effectivity and side effects (Dickfeld T, Ruf A, Pogatsa-Murray G, Muller I, Engelmann B, Taubitz W, Fischer J, Meier O, Gawaz M. Differential antiplatelet effects of various glycoprotein IIb-IIIa antagonists. Thromb Res. 2001; 101:53-64. Gawaz M, Neumann F J, Schomig A. Evaluation of platelet membrane glycoproteins in coronary artery disease: consequences for diagnosis and therapy. Circulation. 1999; 99:E1-E11).

The inhibition of platelet aggregation leads to a general impairment of the platelets with regard to their ability to aggregate. Accordingly, not only the undesired thrombosis formation is influenced, but also the general ability of the platelets to terminate bleeding. Therefore, the administration of inhibitors of platelet aggregation inherently leads to severe side effects such as bleedings which may cause further life-threatening complications. These side effects are of course still more problematic in patients suffering from diabetes.

Diabetes is one of the main risk factors for atherosclerosis. Additionally diabetes constitutes an increased risk of life threatening complications and excess morbidity in patients presenting with acute vascular and especially coronary syndromes. Diabetic patients with unstable angina present with a higher incidence of plaque ulceration and intracoronary thrombosis compared to non-diabetic patients. (Biondo-Zoccai GGL; Abbate A; Liuzzo G, Biasucci L: Atherothrombosis, inflammation, and diabetes. J Am Coll Cardiol 41; 1071-1077; 2003).

It is increasingly recognized that platelets are a major trigger for the progression of atherosclerosis. The link between increased atheroprogression, and increased platelet responsiveness and diabetes is so far an unresolved problem. Diabetic patients suffer from acute vascular complications independent of the degree of atherosclerosis indicative of different presently unknown mechanisms for platelet activation in the development of diabetic acute vascular complications and atherosclerotic acute vascular complications.

Therefore, it is the problem of the invention to provide a medicament which is useful for avoiding life-threatening complications subsequent to an acute coronary or carotid syndrome while maintaining the potency of the blood for hemostasis.

It is a further problem of the preent invention to provide a medicament for the treatment or prevention of atheroprogression.

It is a still further problem of the invention to provide a medicament for the treatment of diabetes, notably complications associated with diabetes.

It is a further problem of the invention to provide an in vitro and an in vivo screening method for inhibitors of adhesion of platelets to intravascular lesions.

GENERAL DESCRIPTION OF THE INVENTION

The above problems are solved according to the claims. The present invention provides the first direct in vivo evidence indicating that GPVI is in fact strictly required in the process of platelet recruitment under physiological shear stress following vascular injury. In different mouse models of endothelial denudation both inhibition or absence of GPVI virtually abolished platelet-vessel wall interactions and platelet aggregation, identifying GPVI as the major determinant of arterial thrombus formation. This indicates that inhibition of GPVI-ligand interactions prevents arterial thrombosis in the setting of atherosclerosis. The present invention uses the antithrombotic potential of a specific soluble form of GPVI. Specifically, a fusion protein is provided, which contains the extracellular domain of GPVI and a human N-terminal Fc tag. The soluble form of human GPVI specifically binds to collagen with high affinity and attenuated platelet adhesion to immobilized collagen in vitro and to sites of vascular injury in vivo. Accordingly, the present invention is based on the recognition that the precondition for intraarterial thrombosis as an acute clinical complication is the initial adhesion of platelets to active lesions in the vessel walls. The present inventors have recognised that platelet adhesion to subendothelial matrix collagen at a lesion of the vessel wall by the glycoprotein VI (GPVI) receptor represents the key event for the formation of thrombosis. The inhibition of the adhesion of platelets to subendothelial matrix collagen of the fusion protein of the invention is therefore capable of not only preventing adhesion of platelets to an active lesion, but also to prevent aggregation of platelets at the active lesion. Thereby, the formation of intravascular thrombosis can be efficiently avoided without impairing the general ability of the platelets for aggregation.

It is surprising that the complex process of the formation of thrombosis may be inhibited by the inhibition of a single platelet receptor in view of the fact that different components of the subendothelial layers are ligands and activators of platelets such as laminin, fibronectin, von Willebrand factor (vWf) and collagen. Moreover, a wide variety of receptors on the platelets had been proposed by in vitro examinations, but the relevant receptor or receptor combinations which influence adhesion of platelets to lesions in vivo had not been known before.

The present invention is also based on the recognition that GP VI is a major meditor of platelet activity for the progression of atherosclerosis. It is demonstrated that inhibition of the collagen-medited GPVI activation attenuates atheroprogression in atherosclerosis prone Apo e −/− mice (see FIG. 16). Moreover, it is demonstrated that the platelets from diabetic patients, who are also prone for advanced atherosclerosis and increased thrombotic complications show an increaed expression of the GPVI-coreceptor Fc-receptor. Therefore platelets from diabetics might show increased responsiveness to collagen stimulation leading to the clinically observed increased thrombotic complications in unstable angina, where collagen is uncovered from subendothelial vascular layers by plaque rupture or endothelial denudation.

The present invention provides therefore a treatment of atheroprogression in patients, notably in patients suffering from diabetes. Moreover, the invention provides a medicament for the treatment of acute vascular complications such as intravascular thrombosis especially in patients with diabetes. The immunoadhesin Fc-GPVI-nt is a potent therapeutic tool to attenuate atheroprogression and increased responsiveness of platelets to collagen via the GPVI receptor. Therefore, Fc-GPVI-nt is a medicament for treatment of atherosclerosis and particularly for the treatment of atherosclerotic complications in diabetes.

This invention provides a fusion protein (Fc-GPVI-nt) comprising the following segments:
(a) the extracellular domain of glycoprotein VI (GP VI) or a variant thereof that is functional for binding to collagen and
(b) the Fc domain of an immunoglobulin or a function-conservative part thereof.

The fusion protein is characterised by an amino acid sequence as shown in FIG. 7. The fusion protein according to the invention is obtained or obtainable by
(a) collecting 2 days after infection the culture supernatant of Hela cells infected with an adenovirus for Fc-GPVI-nt coding for an amino acid sequence as shown in FIG. 7;
(b) centrifuging (3800 g, 30 min, 4° C.) the supernatant of step (a);
(c) filtrating (0.45 µm) the supernatant of step (b);
(d) precipitating the immunoadhesin by addition of 1 vol. ammonium sulfate (761 g/l) and stirring overnight at 4° C.;
(e) pelletizing the proteins by centrifugation (3000 g, 30 min, 4° C.),
(f) dissolving the pelletized proteins of step (e) in 0.1 Vol PBS and dialysed in PBS overnight at 4° C.;
(g) clarifying the protein solution by centrifugation (3000 g, 30 min, 4° C.);
(h) loading the solution of step (g) on a protein A column (HiTrapυ protein A HP, Amersham Pharmacia Biotech AB, Uppsala, Sweden);
(i) washing the column with binding buffer (20 mM sodium phoshate buffer pH 7.0, 0.02% $NaN_3$) until $OD_{280}$<0.01;
(k) eluting fractions with elution buffer (100 mM glycine pH 2.7);
(l) neutralizing the eluted fractions with neutralisation buffer (1 M Tris/HCl pH 9.0, 0.02% $NaN_3$);
(m) pooling the fractions;
(n) dialysing the pooled fractions in PBS overnight at 4° C.,
(o) aliquoting the dialysed product and freezing at −20° C.

Under the above conditions, the fusion protein is obtained as a covalently linked dimer of a molecular mass of 160 kDa as measured under non-reducing conditions by SDS-PAGE. Dimerisation of the fusion protein presumably occurs by inter-chain disulfide bonds of cysteins in a specific domain adjacent to the GPVI fragment of the amino acid sequence as shown in FIG. 7. The dimeric nature of the fusion protein depends at least from the presence of a specific region between the Fc portion and the GPVI portion as contained in FIG. 7, and the preparation process. A monomeric fusion protein is not useful as a therapeutic agent in practice since the inferior binding properties of a monomeric fusion protein as compared to the dimeric fusion protein would require administration of protein in an amount which is in the order of one magnitude larger than the amount of the dimeric fusion protein for obtaining a similar effect, cf. FIG. 9(e). The administration of large amounts of protein is, however, problematic from a therapeuic and economic point of view, in particular in the treatment of chronic disease.

The fusion protein of the invention is an immunoadhesin. It has a segment (a) that has the function of the extracellular domain of platelet GP VI. Said GPVI may be a mammalian GPVI, preferably it is human GPVI. Said function is preferably binding to the GP VI ligand collagen. The whole extracellular domain of GPVI may be used for said fusion protein or any fragments thereof provided said fragments are capable of binding to collagen. A variant of the fusion protein may have a modification at one or several amino acids of said fusion protein (e.g. glycosylation, phosphorylation, acetylation, disulfide bond formation, biotinylation, chromogenic labelling like fluorescein labelling etc.). Preferably, a variant is a homolog of said fusion protein. An engineered variant may be tested easily for its capability of binding to collagen using the methods disclosed herein. Most preferably, the polypeptide of residues 1 to 267 of SEQ ID No: 1 is used as segment (a). However, said polypeptide may also be modified by exchanging selected amino acids or by truncating said sequence without abolishing said function.

Segment (b) of said fusion protein serves at least one of the following purposes: secretion of the fusion protein from cells that produce said fusion protein, providing segment (a) in a form (e.g. folding or aggregation state) functional for binding collagen, affinity purification of said fusion protein, recognition of the fusion protein by an antibody, providing favourable properties to the fusion protein when used as a medicament. Surprisingly and most importantly, segment (b) allows production of said fusion protein in mammalian, preferably human, cells and secretion to the cell supernatant in active form, i.e. in a form functional for binding to collagen. Segment (b) is most preferably an Fc domain of an immunoglobulin. Suitable immunoglobulins are IgG, IgM, IgA, IgD, and IgE. IgG and IgA are preferred. IgGs are most preferred. Said Fc domain may be a complete Fc domain or a function-conservative variant thereof. A variant of Fc is function-conservative if it retains at least one of the functions of segment (b) listed above. Most preferred is the polypeptide of residues 273 to 504 of SEQ ID No. 1. It is, however, general knowledge that such a polypeptide may be modified or truncatated without abolishing its function.

Segments (a) and (b) of the fusion protein of the invention may be linked by a linker. The linker may consist of about 1 to 100, preferably 1 to 10 amino acid residues.

Most preferably, said fusion protein has the amino acid sequence of SEQ ID No. 1 (termed Fc-GPVI-nt herein).

The invention further provides a nucleic acid sequence coding for the fusion protein of the invention. Said nucleic acid sequence comprises a sequence selected from the following group:
(i) the nucleic acid sequence of SEQ ID No: 2 or a variant thereof that codes for the same polypeptide according to the degeneracy of the genetic code;
(ii) a nucleic acid sequence coding for a polypeptide that has at least 70% sequence homology to the polypeptide encoded by SEQ ID No: 2;
(iii) a nucleic acid coding for a polypeptide of at least 300 amino acids, whereby a segment of at least 100 amino acids is functional for binding to collagen and a segment of at least 200 amino acids is functional as an Fc domain; and
(iv) a nucleic acid sequence coding for the fusion protein of claim 1.

The invention further provides a medicament for the prevention or treatment of intraarterial thrombosis, containing a protein that comprises the extracellular domain of glycoprotein VI or a variant thereof that is functional for binding to collagen. Preferably, said protein is said fusion protein of the invention. If said medicament contains said fusion protein, said medicament preferentially further comprises a suitable carrier. Said medicament is preferably administered parenterally, more preferably it is administered intravenously. As has been found by the present inventors, GP VI-collagen interactions are the major factor of platelet adhesion to an injured vessel wall. The fusion protein of the invention can prevent binding of platelets to blood-exposed collagen in the vascular system by blocking said blood-exposed collagen without inhibiting other platelet functions.

Alternatively, the medicament of the invention may contain a nucleic acid that codes for said fusion protein of the invention for gene therepy. Said nucleic acid preferably contains the nucleic acid sequence defined above. Said nucleic acid is preferably contained in a vector, preferentially a viral vector. Vectors encoding said fusion protein may be introduced into the vascular system of a patient such that e.g. endothelial cells are transduced therewith. Suitable vectors for gene therapy are known in the art. They may be based e.g. on adenoviruses, on adeno-associated viruses, on retro viruses, or on herpes simplex viruses. Vectors may be adopted for long-term or for short-term expression of the fusion protein by transduced cells, as the patient requires. The Fc domain of the fusion protein enables secretion of the fusion protein in active form by transduced cells.

The invention further provides a method of in vitro screening for inhibitors of binding of glycoprotein VI to collagen, comprising
(i) providing a surface that exposes collagen;
(ii) contacting a portion of said surface with the fusion protein of the invention under predetermined conditions that allow binding of said fusion protein to said surface;
(iii) contacting another portion of said surface with said fusion protein in the presence of a test compound under conditions as in step (ii);
(iv) determining the amount of said fusion protein bound to said surface in the absence and in the presence of said test compound;
(v) identifying a test compound as inhibitor if binding of said fusion protein to said surface is less in the presence of said test compound as compared to the absence of the test compound; and
(vi) optionally determining the functional effect of said inhibitor on platelet aggregation and/or platelet activation.

The surface of step (i) may be a glass or plastic surface coated with collagen. The portions of said surface may be the wells of a titer plate or a multi-well plate. A surface that exposes collagen may be easily prepared by coating a glass or plastic surface with collagen as described in the examples. Collagen-coated plates or multi-well plates are also commercially available. In step (ii), a predetermined amount of said fusion protein is contacted with a first portion of said surface under conditions (notably pH, buffer, temperature) that allow binding of the fusion protein to the surface. Preferably, conditions are chosen that allow optimal binding to said surface. In step (iii), another surface portion is contacted with the same amount of fusion protein and under the same conditions as in step (ii) in the presence of a predetermined amount or concentration of a test compound. More than one amount or concentration of a test compound may be used. Said determining of step (iv) preferably comprises washing of said surface portions contacted according to steps (ii) and (iiii) one or more times in order to remove unbound fusion protein. The amount of bound fusion protein may then be determined e.g. by measuring the fluorescence of a fluorescent label (e.g. fluorescein, rhodamine etc.) attached to the fusion protein. Alternatively, bound fusion protein may be detected using an antibody against said fusion protein, whereby said antibody may be fluorescently labelled. Alternatively, the antibody may be labelled with an enzyme (e.g. alkaline phosphatase, a peroxidase, luciferase) capable of producing a coloured or luminescent reaction product. Most conveniently, the fusion protein may be labelled with a chromogenic label such that the label changes its light absorption or light emission characteristics upon binding to collagen. In this embodiment, washing off of unbound fusion protein is not needed.

In step (v), inhibitors may identified. Identified inhibitors or selected moieties thereof may be used as lead structures for improvement of the inhibitor. Such lead structures may be modified using chemical methods and the modified structures may again be tested with this screening method. Modified structures or test compounds with improved inhibition properties may be selected and optionally further varied by chemical methods. In this way, iterative improvement of an inhibitor may be achieved. The inhibitors identified using the screening methods of the invention are valuable as potential drugs against thrombosis and arteriosclerosis.

In step (vi), the functional effect of said inhibitor on platelet aggregation and/or platelet activation may be determined according to methods described below, e.g. by intravital fluorescence microscopy.

Said screening method may be carried out on small, medium, or large scale depending on the number of test compounds to be tested. If many test compounds are to be tested (e.g. libraries of chemical compounds), the screening method preferably takes the form of a high-throughput screening (HTS). For HTS, the amount of bound fusion protein is preferably detected using fluorescently labelled fusion protein.

The above screening method may also be adopted for screening for antibodies that inhibit binding of GP VI to collagen, notably antibodies against the extracellular domain of GP VI. Such an antibody screening may be combined with e.g. hybridoma technology of generating monoclonal antibodies or any other antibody generating technique, whereby the fusion protein of the invention is preferably used as antigen. Antibodies in hybridoma cell supernatants may be used as said test compounds.

The invention further provides antibodies produced by using the fusion protein of the invention as immunogen. Moreover, use of an antibody against GPVI is provided for the preparation of a medicament for the prevention of platelet adhesion at exposed subendothelial matrix collagens in active atherosclerotic lesions as the initial trigger for acute coronary or carotid syndrome. Such indications may be diagnosed as described below. Preferably, the patient is further characterized by suffering from unstable atherosclerotic plaque. Said medicament is preferably administered parenterally. Preferably, said antibodies are monoclonal antibodies. Such antibodies may e.g. be prepared using the fusion protein of the invention as immunogen.

Furthermore, the invention provides a method of in vitro screening for an inhibitor of GPVI mediated adhesion of platelets to active intravascular lesions, said method comprising the steps of
(i) providing a surface exposing collagen;
(ii) contacting the surface with platelets under predetermined conditions allowing for an adhesion of the platelets to the collagen;
(iii) measuring the adhesion of platelets in the presence of a test compound; and
(iv) identifying the test compound as an inhibitor of GPVI when the adhesion of platelets to collagen is less in the presence of the test compound as compared to the absence of the test compound; and
(v) optionally determining the functional effect of said inhibitor on platelet aggregation and/or platelet activation.

Platelets to be used in this method may be isolated according to known procedures (cf. example 7). They may be isolated from blood of mammals like mice, rats, rabbits, pigs etc. Preferably, they are isolated from humans. Said platelets may be labelled e.g. with a fluorescent dye like fluorescein. The adhesion of platelets to said surface may be measured as described in the examples. The test compounds for this method may be small organic molecules. Preferably, the test compounds for this methods are inhibitors identified in the above method of screening for inhibitors of binding of GP VI to collagen. In this way, the number of compounds to be screened using platelets can be significantly reduced and the likelihood of finding inhibitors functional with platelets can be increased.

Method of in vivo screening for an inhibitor of GPVI mediated adhesion of platelets to active intravascular lesions, said method comprising the steps of
(i) providing an in vivo model for active intravascular lesions;
(ii) measuring the adhesion of platelets to an active intravascular lesion in the presence of a test compound, and
(iii) identifying the test compound as an inhibitor of GPVI when the adhesion of platelets to the active intravascular lesion is less in the presence of the test compound as compared to the absence of the test compound.

Said in vivo model may be a suitable mammal like a mouse, a rat, a rabbit etc. Preferably, it is a mouse. Platelets that are preferably fluorescently labelled are introduced into the model prior to measuring the adhesion of platelets to an active intravascular lesion in the presence and in the absence of a test compound. Said test compound has preferably been identified as an inhibitor in one of the above in vitro screening methods. Adhesion of platelets to an active intravascular lesion may be carried out by using in vivo fluorescence microscopy as described in example 8.

The present invention also provides a use of a fusion protein comprising
(a) the extracellular domain of glycoprotein VI or a variant thereof that is functional for binding to collagen and
(b) the Fc domain of an immunoglobulin or a function-conservative part thereof, for the manufacture of a medicament for the treatment of diabetes.

The fusion protein used for the manufacture of a medicament for the treatment of diabetes is preferably a dimeric fusion protein. In order to provide for the possibility of dimerisation, a hinge region must be present between domains (a) and (b) of the fusion protein. The hinge region is required for allowing suitable orientation of the polypeptide chains and formation of inter-chain disulfide bonds. Accordingly, the hinge region must have a sufficient length and contain cystein residues, preferably at least two cystein residues. Preferably, the fusion protein comprises residued 1 to 267 of SEQ ID No:1. The fusion protein is used for the treatment of acute complications of diabetes or for the treatment of chronic progression of atherosclerosis in diabetic patients. Preferably, the fusion protein is Fc-GPVI-nt.

The present invention also provides a method for the preparation of a fusion protein of the invention (Fc-GPVI-nt), which comprises the following steps:
(a) collecting 2 days after infection the culture supernatant of Hela cells infected with an adenovirus for Fc-GPVI-nt coding for an amino acid sequence as shown in FIG. 7;
(b) centrifuging (3800 g, 30 min, 4° C.) the supernatant of step (a);
(c) filtrating (0.45 µm) the supernatant of step (b);
(d) precipitating the immunoadhesin by addition of 1 vol. ammonium sulfate (761 g/l) and stirring overnight at 4° C.;
(e) pelletizing the proteins by centrifugation (3000 g, 30 min, 4° C.), (f) dissolving the pelletized proteins of step (e) in 0.1 Vol PBS and dialysed in PBS overnight at 4° C.;
(g) clarifying the protein solution by centrifugation (3000 g, 30 min, 4° C.);
(h) loading the solution of step (g) on a protein A column (HiTrap™ protein A HP, Amersham Pharmacia Biotech AB, Uppsala, Sweden);
(i) washing the column with binding buffer (20 mM sodium phoshate buffer pH 7.0, 0.02% $NaN_3$) until $OD_{280}$<0.01;
(k) eluting fractions with elution buffer (100 mM glycine pH 2.7);
(l) neutralizing the eluted fractions with neutralisation buffer (1 M Tris/HCl pH 9.0, 0.02% $NaN_3$);
(m) pooling the fractions;
(n) dialysing the pooled fractions in PBS overnight at 4° C.,
(o) aliquoting the dialysed product and freezing at −20° C.

DESCRIPTION OF THE FIGURES

FIG. 7 Amino acid sequence of Fc-GPVI-nt: SEQ ID No: 1.

FIG. 8 DNA-Sequence of immunoadhesin Fc-GPVI-nt: SEQ ID No. 2. Bases 1 to 807 encode the extracellular domain of GP VI. Bases 817 to 1515 encode the Fc part of the IgG.

FIG. 9 Characterization of GPVI-Fc. (a) upper panel: Fc-GPVI-nt and control Fc lacking the extracellular GPVI domain were used for SDS-PAGE under reducing conditions. Coomassie blue stain (left) and immunoblotting with peroxidase-conjugated goat anti-human Fc antibody (right) identified Fc-GPVI-nt with a molecular mass of ~80 kDa. Middle panel. Immunoblotting of Fc, Fc-GPVI-nt, or human platelets using the anti-GPVI monoclonal antibody 5C4. 5C4 detected both adenovirally expressed Fc-GPVI-nt fusion protein and platelet GPVI, but not the control Fc. Lower panel: Molecular mass under reducing (right) and non-reducing (left) conditions. While the molecular mass of Fc-GPVI-nt was approximately 80 kDa under reducing conditions, the complete nt with ~160 kDa protein was identified under non-reducing conditions. (b-d) Characterization of Fc-GPVI-nt collagen interactions. (b) Binding assays using different concentrations of soluble Fc-GPVI-nt and immobilized collagen (10 µg/ml) were performed to define Fc-GPVI-nt-collagen interactions. Bound Fc-GPVI-nt was detected by anti-Fc mAb antibody (dilution 1:10.000) and is given relative to the binding observed at 10 µg/ml Fc-GPVI-nt. Fc-GPVI-nt binds to collagen in a saturable manner. Mean±s.e.m., n=6 each Fc-GPVI-nt concentration, asterisk indicates significant difference compared to 0 µg/ml Fc-GPVI-nt, P<0.05. (c, left panel) shows binding of Fc-GPVI-nt (20 µg/ml) to various substrates. Binding of Fc-GPVI-nt to BSA (10 µg/ml) or vWF (10 µg/ml) is given as percentage of GPVI-dimer-binding to immobilized collagen. Binding of Fc-GPVI-nt did not occur to BSA or vWF, supporting the specificity of Fc-GPVI-nt binding. Mean±s.e.m., asterisk indicates significant difference compared to collagen, P<0.05. (c, right panel) illustrates binding of Fc-GPVI-nt (20 µg/ml) or Fc (20 µg/ml) to immobilized collagen (10 µg/ml). Bound Fc-GPVI-nt or Fc was detected by anti-Fc mAb antibody (dilution 1:10,000) and is given relative to the binding observed with Fc-GPVI-nt. Only Fc-GPVI-nt, but not Fc or anti-Fc mAb binds to immobilized collagen. Mean±s.e.m., n=8 each group, asterisk indicates significant difference compared to Fc-GPVI-nt binding, P<0.05. (d) Fc-GPVI-nt (20 µg/ml) was preincubated for 10 min with different concentrations of soluble collagen. After incubation the plates were washed and Fc-GPVI-nt binding was detected by peroxidase-conjugated goat anti-human IgG antibody (dilution 1:10.000). Fc-GPVI-nt binding is given relative to the binding observed in the absence of soluble collagen. Soluble collagen inhibits GPVI-Fc-dimer-dimer binding to immobilized collagen in a dose-dependent manner. Mean±s.e.m., n=3 each collagen concentration, asterisk indicates significant difference compared to 0 mg/ml collagen, P<0.05. (e) The difference of the binding affinity between the monomeric form of the GPVI-Fc fusion portein and Fc-GPVI-nt was assessed in direct comparison. The binding of the monomer and dimer was assessed on collagen type 1 coated ELISA plates. Increasing concentrations of the GPVI fusion proteins bond to collagen in a sturable manner. Here a Linewaver Burke plot is demonstrated for affinity assessment (e). The affinity of the monomeric GPVI fusion protein was about 10 times lower compared to equimolar concentrations of the dimeric form Fc-GPVI-nt.

FIG. 13 Fc-GPVI-nt inhibits platelet adhesion to immobilized collagen under flow conditions. Human platelets ($2 \times 10^8$ cells/ml) were isolated from whole blood (for details see "materials and methods"). Plates were coated with immobilized collagen (10 µg/ml) or vWF (10 µg/ml). Platelet adhesion to the coated plates was determined in a parallel plate flow chamber in the presence of Fc-GPVI-nt or Fc lacking the extracellular GPVI domain (200 µg/ml). Inhibition of platelet adhesion by Fc-GPVI-nt is given in % of control (Fc control). Fc-GPVI-nt significantly attenuated platelet adhesion on immobilized collagen at shear rates of 500 sec$^{-1}$ and 1000 sec$^{-1}$, respectively. In contrast, Fc-GPVI-nt did not affect platelet adhesion on immobilized vWF. Mean±s.e.m., n=4 each group, asterisk indicates significant difference compared to control Fc, P<0.05. The lower panels show representative microscopic images.

FIG. 16 Fc-GPVI-nt significantly attenuates atheroprogression in apo e −/− knockout mice in vivo. Apo e −/− mice were treated with Fc-GPVI-nt (4 μg/g) or control Fc (4 μg/g) intraperitoneally for 4 weeks twice weekly. Atheroprogression was investigated post mortem after sudan red staining of the large vessels to visualise atheroma and plaque formation. In control animals extensive plaque formation of carotid artery preparations was indicated by the red colour in particular in the branching region. In Fc-GPVI-nt treated animals atherosclerosis was almost completely abolished in carotid arteries of apo e −/− mice. Representative macroscopic whole vascular preparations of the carotide arteries of an apo e −/− mouse after 4 weeks treatment with Fc-GPVI-nt (left side) and of an apo e −/− mouse after 4 weeks treatment with the control Fc protein (right side) are shown.

FIG. 17 Freshly isolated platelets from patients suffering from diabetes mellitus show reduced expression of the fibrinogen receptor (CD61, top) and increased expression of the Fc receptor (CD32, middle) and therefore increased expression of GPVI. The correleation between CD32 expression and GPVI expression (detected by the specific monoclonal antibody 4C9) is shown on human platelets (bottom). Human platelets were isolated from whole blood from patients suffering from diabetes and incubated with fluorescent anti-CD61 and anti CD32 antibodies or FITC labelled 4C9 antibodies. Fluorescence was determined in a Becton Dickenson FACScalibur device. The means+/−s.e.m. from n=111 diabetic patients and from n=363 patients without diabetes are summarized. Correlation of CD32 fluorescence and 4C9 fluorescence was calculated with the correlation coefficient r=0.516.

FIG. 18 Amino acid sequence of a monomeric fusion protein based on Fc-GPVI-nt.

DETAILED DESCRIPTION OF THE INVENTION

Figure 1A:
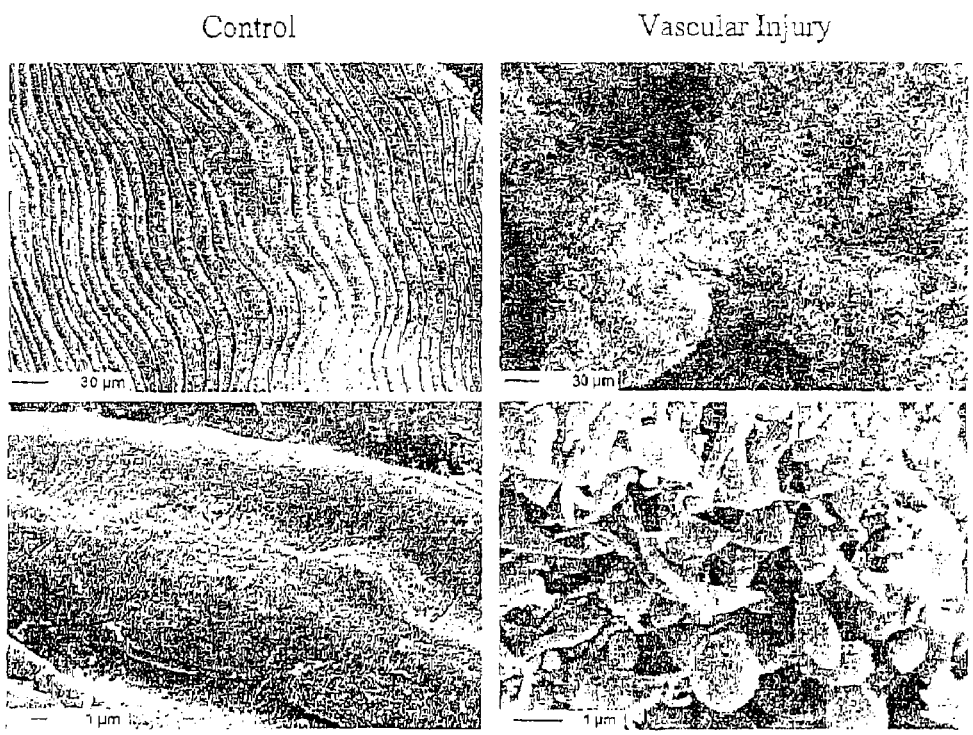
FIG. 1 Platelet adhesion and aggregation following vascular injury of the common carotid artery in C57BL6/J mice in vivo. (a) Scanning electron micrographs of carotid arteries prior to (left panels) and 2 hrs after (right panels) vascular injury. Endothelial denudation induces platelet adhesion and aggregation, resulting in the formation of a platelet-rich (lower left) thrombus. (b) Platelet-endothelial cell interactions 5 min after vascular injury were investigated by in vivo fluorescence microscopy of the common carotid artery in situ (black columns). Animals without vascular injury served as controls (open columns). The left and right panels summarize transient and firm platelet adhesion, respectively, of eight experiments per group. Platelets were classified according to their interaction with the endothelial cell lining as described[24] and are given per $mm^2$ of vessel surface. Mean±s.e.m., asterisk indicates significant difference compared to control, P<0.05. (c) Platelet aggregation following vascular injury was determined by fluorescence microscopy in vivo (black columns). Animals without vascular injury served as controls (open columns). Mean±s.e.m., n=8 each group, asterisk indicates significant difference compared to wild type mice, P<0.05. The microphotographs (right) show representative in vivo fluorescence microscopy images in control animals (upper panel) or following vascular injury (lower panel). White arrows indicate adherent platelets.

A previous hypothesis suggested that platelet glycoprotein (GP) lb binding to von vWf recruits flowing platelets to the injured vessel wall (Ruggeri, Z. M:. Mechanisms initiating platelet thrombus formation. *Thromb. Haemost* 1997; 78, 611-616), whereas subendothelial fibrillar collagens support firm adhesion and activation of platelets (van Zanten, G. H. et al. Increased platelet deposition on atherosclerotic coronary arteries. *J. Clin. Invest* 1994; 93, 615-632; Clemetson, K. J. & Clemetson, J. M. Platelet collagen receptors. *Thromb. Haemost.* 2001, 86, 189-197). However, the present invention demonstrates by in vivo fluorescence microscopy of the mouse carotid artery that inhibition or absence of the major platelet collagen receptor, GPVI, instead, abolishes platelet-vessel wall interactions following an endothelial erosion. Unexpectedly, inhibition of GPVI reduces platelet tethering and adhesion to the subendothelium by approximately 89%. Furthermore, stable arrest and aggregation of platelets is virtually abolished under these conditions. The strict requirement for GPVI in these processes was confirmed in GPVI-deficient mice, where platelets also fail to adhere and aggregate on the damaged vessel wall. These findings reveal an unexpected role of GPVI in the initiation of platelet attachment at sites of vascular injury and unequivocally identify platelet-collagen interactions as the major determinant of arterial platelet-induced atherosclerotic complications.

The fact that GPVI generally functions as a receptor for the subendothelial matrix collagen has been described (Moroi M, Jung S M, Okuma M, Shinmyozu K. A patient with platelets deficient in glycoprotein VI that lack both collagen-induced aggregation and adhesion. J Clin Invest 1989; 84: 1440-1445). These authors characterized platelets in vitro originating from patients with a GP VI receptor deficiency. However, the physiological significance of the interaction of collagen and GP VI receptor in the in vivo context and the relative contribution of the GP VI receptor for adhesion following vascular injury was unknown. In particular, it was not known that inhibition of this receptor inhibits the key step in the formation of intravascular thrombosis that is platelet tethering. The present invention reveals the GP VI receptor as an essential receptor for platelet adhesion to the subendothelium via the attachment to subendothelial matrix collagen in vivo. Amongst the variety of other platelet surface proteins such as GP lb (von Willebrand receptor), the αIIbβ3 integrin receptor, the α2β1 integrin or the GP V receptors, we have surprisingly identified the GP VI receptor to be an essential receptor to mediate platelet adhesion to the vascular wall. Since platelet adhesion is the first and most important step for platelet aggregation and intraarterial thrombus formation under physiologic shear stress conditions, the following deleterious effects leading to intraarterial occlusion are the functional basis for the clinical syndromes of myocardial infarction or cerebral stroke. In a chronic setting, the interaction of platelets with the endothelium propagates early steps of arteriosclerosis. Our invention also showed for the first time that the GP VI receptor plays a crucial role amongst the complex variety of several platelet surface proteins for initial platelet adhesion and for chronical platelet—endothelium interaction in the propagation of arteriosclerosis.

WO 01/16321 and WO 01/00810 disclose a DNA and protein sequence of the human GPVI receptor. However, the significance on platelet adhesion and activation by endothelial lesions has not been demonstrated in an in vivo background.

U.S. Pat. No. 6,383,779 discloses fusion proteins of GPVI. However, this reference does not disclose a dimeric fusion protein or any therapeutic effect of GPVI.

Recently, the different phases of platelet-collagen interaction to artificial collagen in vitro during perfusion conditions were investigated (Moroi M, Jung S M, Shinmyozu K, Tzomiyama Y. Ordinas A and Diaz-Ricart M. Analysis of platelet adhesion to collagen-coated surface under flow conditions: the involvement of glycoprotein VI in the platelet adhesion. Blood 1997; 88: 2081-2092). The authors of that study already pointed out the importance of collagen-GP VI interaction during shear stress conditions. However, the relevance of subendothelial matrix collagen for the adhesion could not be studied in this artificial in vitro situation. As a consequence of limited relevance of their in vitro model, the authors of the above mentioned study came to the conclusion that GP VI receptors are rather involved in platelet activation than in platelet adhesion to the endothelium. In contrast, the von Willebrand GP 1b receptor is significantly involved in platelet-subendothelial interaction. These authors also focussed all available information about platelet—collagen interaction in a review of the current literature. Previously, Moroi M and Jung, S M (Platelet receptors for collagen. Thromb. Haemost. 1997; 78: 439-444) have discussed collagen fibril interaction with different collagen receptors on platelets for the adhesion and thrombus formation of platelets. However, the authors did not expect a relevant role of the GP VI receptor for the adhesion in a clinically relevant in vivo situation as they could not validate the significance of the different collagen receptors to the adhesion process.

Therefore, the present invention provides a solution to the problem of inhibiting the relevant target for the platelet—subendothelial interaction and for platelet adhesion without provoking undesired side effects of bleeding complications. Besides the well known interaction of collagen—platelet via the GP VI receptor, we could provide data for the interaction of the native subendothelial matrix and platelets measured by in vivo platelet adhesion. Consecutively, we could validate the significance of the GP VI-endothelium interaction for platelet adhesion as initial step of intravascular thrombosis. Thus, our invention solves the problem of an effective antiplatelet drug treatment for the important step of platelet adhesion without undesired side effects.

Further, the invention provides an immunoadhesin (the fusion protein of the invention). In a specific embodiment, the immunoadhesin consists of the extracellular domain of the GP VI receptor together with the Fc part of an IgG immunoglobulin (Fc-GPVI-nt). This novel fusion protein is based approximately 50% on the original DNA sequence of GP VI as published previously. The protein structure of the immunoadhesin is novel as the recombinant fusion protein does not form a membrane protein like the GP VI receptor but is a soluble, immunoglobulin-like immunoadhesin released by the respective host cell. This immunoadhesin can block the ligand-receptor interaction of collagen and GP VI. Our results demonstrate that the immunoadhesin has marked effects on the main physiological functions of platelets induced by collagen stimulation. Collagen-induced aggregation, adhesion and the release function can be inhibited by the immunoadhesin to the same extent as does a specific, monoclonal antibody. The mechanism, however, is different: whereas the antibody inhibits GP VI activation by directly binding to the ligand binding site of the GP VI receptor, the immunoadhesin scavenges the GP VI ligand collagen and therefore prevents ligand-mediated GP VI activation.

The immunoadhesin of the invention is a novel GP VI inhibitor. It has the advantage of selective inhibition of the activated branch of GP VI mediated effects by ligand scavenging. Secondary effects, like antibody mediated effects on GP VI receptor internalisation are prevented. Fc-GPVI-nt can be used for the treatment of atherosclerotic complications caused by unstable atheroslerotic plaques with plaque rupture or endothelial lesion. Therefore, the immunoadhesin Fc-GPVI-nt serves as a therapeutic inhibitor for collagen-mediated GP VI activation without affecting the intrinsic activity of the GP VI receptor with the relevant signalling system.

Moreover, the GP VI immunoadhesin serves as an ideal epitope for antibody selection. The Fc part allows the convenient purification of the protein and simple fixation to surfaces to perform large scale antibody selection against antibody libraries i.e. by phage display. The selection allows selective antibody screening to the relevant epitope that resembles the intact protein with a similar structure as the native protein.

Finally, the Fc-GPVI-nt is an important tool for the screening for inhibitors of GP VI receptor activation. We have established an ELISA-based in vitro assay simulating the collagen GP VI interaction by collagen precoated plates as the ligand. This assay can alternatively be run with fluorescence-labelled Fc-GPVI-nt and thus be upscaled to high-throughput formats. This assay allows for the screening of both, inhibitory antibodies or small molecules for their potency to inhibit GP VI function by fluorescence measurement. With this cell free screening assay, a prototype method for a high-throughput-scaleable fluorescence screening assays for drug testing has been established.

Based on the recent improvements in imaging techniques by intravascular ultrasound or nuclear magnetic resonance imaging, it is possible to identify patients with atherosclerosis being at risk of acute clinical complications such as acute coronary or carotid syndrome, whereby the patients have active lesions as possible causes for intravascular thrombosis. It is then possible by the present invention to prevent the formation of intravascular thrombosis by the administration of a medicament containing an antibody against platelet glycoprotein VI (GPVI) without undesired side effects.

Active lesions are characterized by the unmasking of subendothelial matrix collagens and platelet activation. The occurrence of such lesions can be investigated e.g. by intravascular ultrasound or thermography (e.g., Fayed and Fuster, Clinical imaging of the high-risk or vulnerable atherosclerotic plaque. Circulation 2001; 89:305-316) or nuclear resonance imaging (Helft et al., Progression and Regression of Atherosclerotic Lesions. Circulation 2002; 105:993-998). Such lesions are highly probable in patients with acute coronary or carotid syndromes, and the risk of the reoccurrence of acute clinical complications such as myocardial infarction or stroke is very high, decreasing progressively with increasing time distance from the primary event.

Therefore, the present invention also provides a method of treating a patient suffering from an acute coronary or carotid syndrome, said method comprising for avoiding intravascular thrombosis the steps of
(a) determining the presence or absence of active intravascular lesions in the patient; and
(b) treating the patient with an antibody against platelet glycoprotein VI (GPVI) in case of the presence of intravascular lesions.

Moreover, based on the present invention, it is possible to treat patients being at risk of intravascular thrombosis due to the rupture of complex arteriosclerotic plaques. The rupture also unmasks the subendothelial collagen matrix. As a consequence of intraarterial thrombus formation, the perfusion of vital organs is blocked with the above described important and life threatenting clinical syndromes.

The present invention also provides a method of treating a patient suffering from a chronic atherosclerotic syndrome, said method comprising for avoiding intravascular thrombosis the steps of
(a) determining the presence or absence of the onset of atheroprogression in the patient; and
(b) treating the patient with an antibody against platelet glycoprotein VI (GPVI) in case of the presence of intravascular lesions.

Accordingly, based on the present invention, it is possible to treat patients being at risk of atherosclerosis. In order to prevent atheroprogression, a patient is treated with the fusion protein of the invention in order to prevent interaction between platelets and exposed subendothelial collagen. The fusion protein of the invention blocks the ligand for the GPVI platelet receptor in the vascular wall (e.g. subendothelium) so that an interaction between the platelets and exposed collagen is inhibited.

The fusion protein of the invention may be in the form of a lyophilised powder which is dispersed in a suitable pharmaceutically acceptable liquid carrier prior to administration to a patient. The fusion protein of the invention can also be incorporated into pharmaceutical compositions suitable for parenteral, in case of the treatment of acute complications preferably intraarterial or intravenous administration. Such compositions usually comprise the fusion protein and a pharmaceutically acceptable carrier. A pharmaceutically acceptable carrier includes solvents, dispersion media, antibacterial and antifungal agents and isotonic agents, which are compatible with pharmaceutical administration. The present invention includes methods for manufacturing pharmaceutical compositions for the treatment of chronic or acute cardiovascular disease. Such methods comprise formulating a pharmaceutically acceptable carrier with the fusion protein of the invention. In case of the treatment of acute cardiovascuar disease, the composition is preferably administered intravenously or intraarterially. In case of the treatment of chronic cardiovascular disease, the composition may also be administered subcutaneously and intraperitoneally. Such compositions can further include additional active compounds, such as further polypeptides (such as insulin) or therapeutically active small molecules. Thus, the invention further includes methods for preparing a pharmaceutical composition by formulating a pharmaceutically acceptable carrier with the fusion protein of the invention and one or more additional active compounds such as insulin. In case of the coformulation of the fusion protein and insulin for the treatment of diabetic patients, it is preferred that the dosage form allows separate storage of the different proteins whereby mixing of the proteins is carried out just prior or during the administration of the composition. Accordingly, application by a multichamber syringe is considered. A pharmaceutical composition of the invention is formulated to be compatible with its intended parenteral route of administration. Examples of routes of parenteral administration include, e.g., intraarterial and intravenous administration. Solutions or suspensions used for parenteral may include a sterile diluent such as water for injection, saline solution, polyethylene glycols, fixed oils, glycerine, propylene glycol, TWEEN or other synthetic solvents; antibacterial agents such as benzyl alcohol or methyl parabens; chelating agents such as ethylenediaminetetraacetic acid; antioxidants such as ascorbic acid or sodium bisulfite; buffers such as acetates, citrates or phosphates and agents for the adjustment of tonicity such as sodium chloride, dextrose, saccarose or mannitose. The pH can be adjusted with acids or bases, such as hydrochloric acid or sodium hydroxide. The parenteral preparation can be enclosed in ampoules, disposable syringes or multiple dose vials made of glass or plastic. Pharmaceutical compositions suitable for injectable use include sterile aqueous solutions or dispersions and sterile powders for the extemporaneous preparation of sterile injectable solutions or dispersions. For intravenous administration, suitable carriers include physiological saline, bacteriostatic water, or phosphate buffered saline (PBS). The carrier can be a solvent or dispersion medium containing, for example, water, ethanol, polyol (for example, glycerol, propylene glycol, and liquid polyetheylene glycol), and suitable mixtures thereof. The proper fluidity can be maintained, for example, by the use of a coating such as lecithin, by the maintenance of the required particle size in the case of dispersion and by the use of surfactants. Prevention of the action of micoorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin. Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. It is especially advantageous to formulate oral or parenteral compositions in dosage unit form. A dosage unit form are discrete units suited as unitary dosages for a patient. Each unit contains a predetermined quantity of active compound to produce the desired therapeutic effect in association with the required pharmaceutical carrier. A therapeutically effective amount of fusion protein (i.e., an effective dosage) for the treatment of acute complications ranges from 0.05 to 5 mg/kg body weight, preferably 0.1 to 2 mg/kg body weight, more preferably 0.1 to 1 mg/kg body weight. A therapeutically effective amount of fusion protein (i.e., an effective dosage) for the treatment of chronic atheroprogression ranges from 0.5 to 6 mg/kg body weight, preferably 1 to 5 mg/kg body weight, more preferably 2 to 5 mg/kg body weight. The treatment of a subject with a therapeutically effective amount of the fusion protein can include a single treatment or, preferably, can include a series of treatments. In a preferred example, a subject is treated with the fusion protein of the invention against chronic atheroprogression in the range of between 0.5 to 6 mg/kg body weight, preferably 1 to 5 mg/kg body weight, more preferably 2 to 5 mg/kg body weight, at least twice per week.

Methods to Investigate Platelet-Collagen Interaction and Modulation by Inhibitors Platelet Aggregation and ATP Release Stimulation of mouse platelet-rich plasma with increasing concentrations of bovine type I collagen from 0.2 to 4 µg/ml elicits a dose-dependent aggregation from 2 to 95% and a dose-dependent ATP release from 0 to 1.66 nM ATP release. A half-maximal collagen concentration was chosen for further experiments. Incubation of the mouse platelet-rich plasma with the specific anti-mouse GP VI antibody JAQ 1 (50 µg/ml and 100 µg/ml) almost completely abolished platelet aggregation after stimulation with 2 µg collagen/ml (with 50 µg JAQ 1:2+/−0.7; with 100 µg JAQ 1: 1.5+/−0.3%). Moreover, ATP release was inhibited in an antibody dose-dependent manner to 1.09 nM ATP (10 µg antibody/ml) or completely abolished (50 and 100 µg antibody/ml).

Similarly, incubation of mouse platelet-rich plasma with the immunoadhesin for GP VI (Fc-GPVI-nt) (50 µg/ml and 100 µg/ml) almost completely abolished platelet aggregation after stimulation with 2 µg collagen/ml (with 50 µg Fc-GPVI-nt: 2+/−0.7; with 100 µg Fc-GPVI-nt: 1.5 +/−0.3%) and ATP release to 0 nM ATP.

Therefore, the immunoadhesin sufficiently inhibited GP VI activation by scavenging the natural GP VI ligand collagen. Both the crucial platelet function aggregation and the platelet release mechanism as determined by ATP release could be influenced by the Fc-GPVI-nt.

GP VI Mediated Adhesion Under Physiological Flow Conditions (Flow Chamber)

Figure 4:
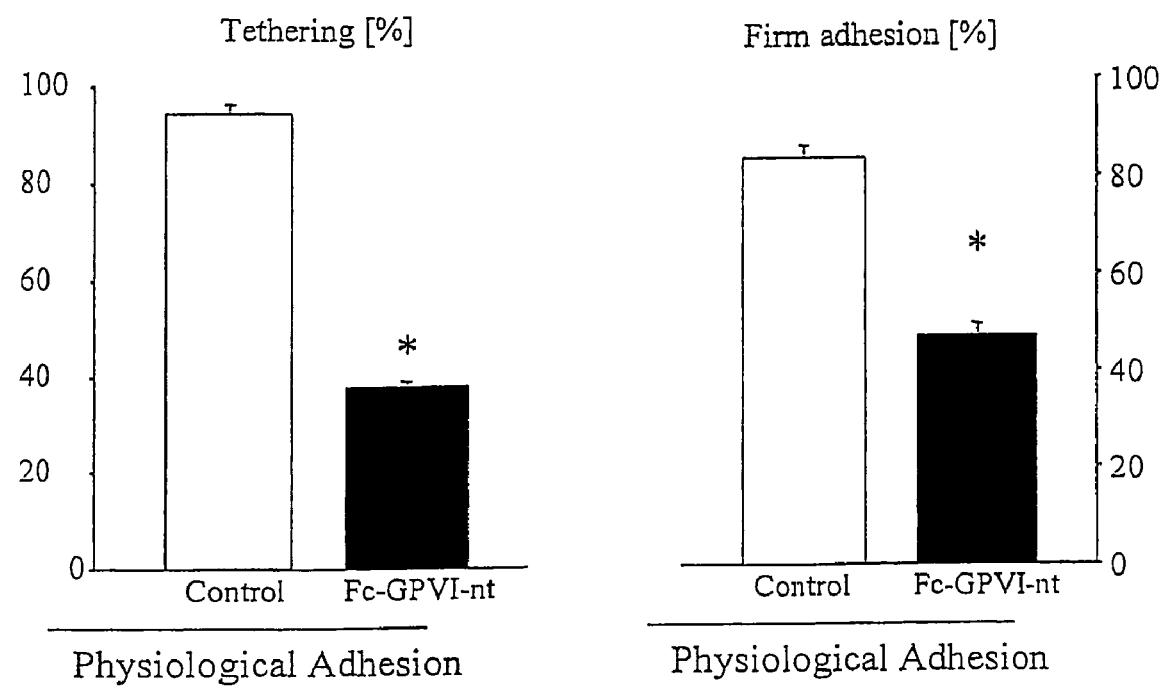
FIG. 4 Platelet adhesion to the surface of collagen coated glass coverslips under physiological flow conditions was assessed ex vivo. Left panel: Platelets from mice pretreated with irrelevant control IgG immunoadhesin (control) (left) or anti-GPVI immunoadhesin (Fc-GP VI-nt) (right) were investigated for adhesion under physiological flow conditions. The number of platelets was assessed by FACS counting of the washed coverslips at the end of each experiment. Platelet tethering as the first step of platelet adhesion was assessed after 30 seconds and firm platelet adhesion after 5 min under flow conditions. (for details see Example 6). The panels summarize transient and firm platelet adhesion in eight experiments per group. Mean±s.e.m., asterisk indicates significant difference compared to control IgG, P<0.05.

Adhesion of platelets under physiological shear conditions was tested in a flow chamber. Initial and firm adhesion of platelets was significantly inhibited by addition of the Fc-GPVI-nt immunoadhesin by 60% (see FIG. 4).

GP VI Binding Assay

Figure 5:
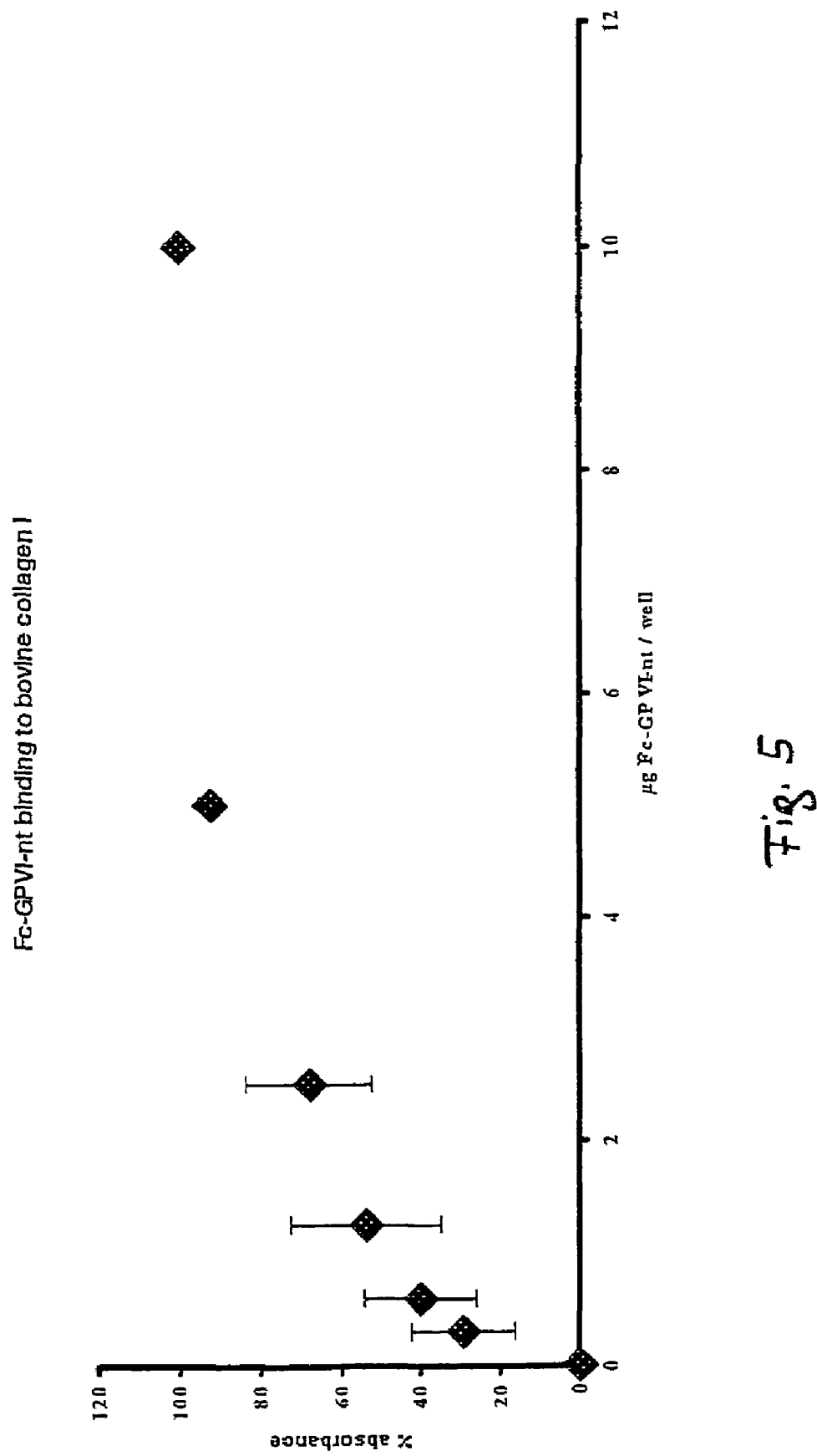
FIG. 5 Interaction of Fc-GP VI-nt with collagen was monitored in an ELISA based assay. Adhesion of the immunoadhesin Fc-GP VI-nt consisting of the extracellular domain of GPVI and the FC part of an IgG to collagen coated plates with increasing concentrations of Fc-GP VI-nt (0.5 µg to 10 µg) was investigated. The binding is visualised with a secondary antibody labelled with peroxidase directed to the Fc part of Fc-GP VI-nt. Peroxidase is finally detected by ELISA. In this representative experiment binding of Fc-GP VI-nt to collagen was monitored with sufficient affinity, which reached saturation at µg concentrations.
Figure 6:
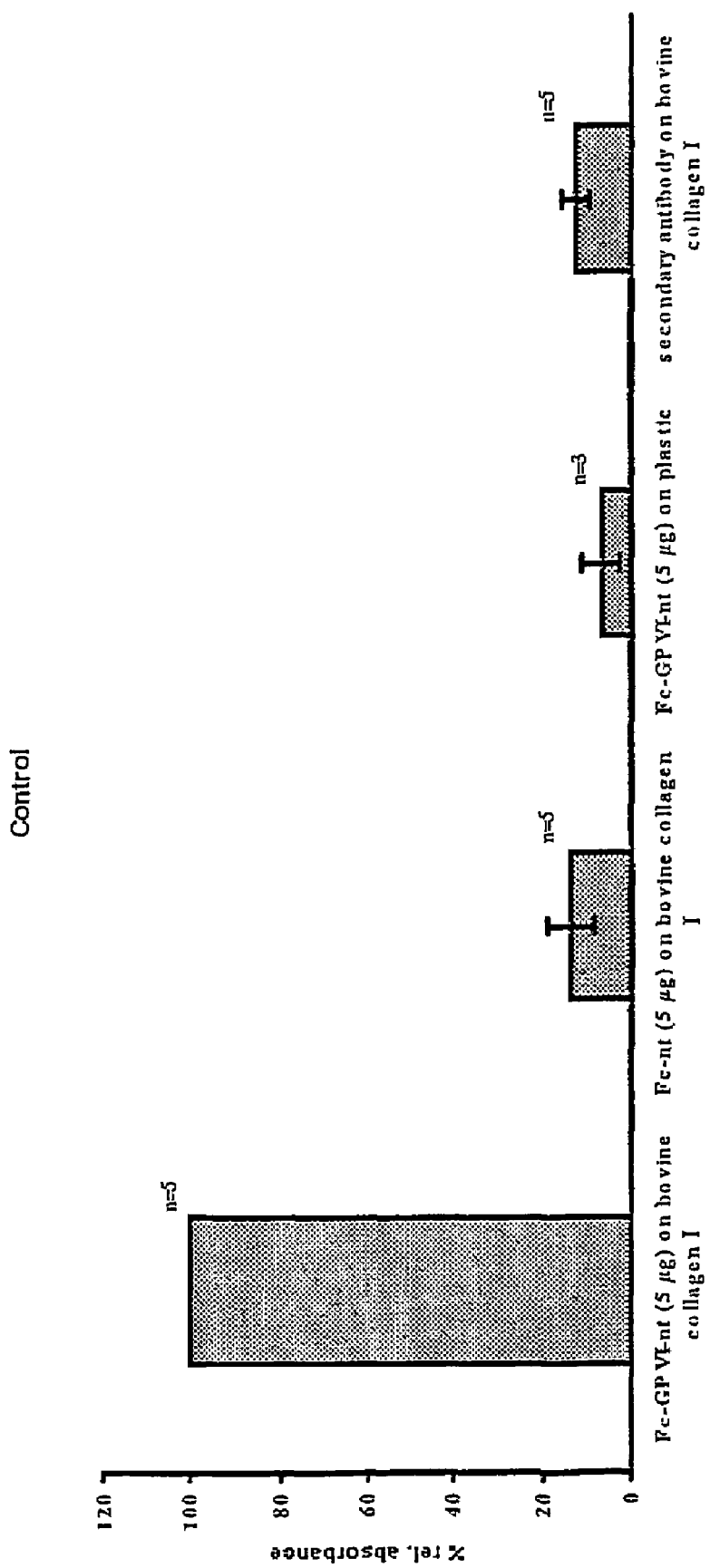
FIG. 6 Interaction of the Fc-GP VI-nt with collagen and the possibility to screen for GP VI inhibitors was demonstrated with the inhibitory anti mouse GP VI antibody JAQ 1. Adhesion of the immunoadhesin Fc-GP VI-nt (2 µg/well) to collagen coated ELISA plates is shown to be specific: the empty immunoadhesin Fc-nt did not show any binding. Thus, this provides an ELISA based assay for the screening against GP VI inhibitors with the upscale potential to high-throughput capacities.

Adhesion of Fc-GPVI-nt to collagen coated plates was determined in an ELISA based fluorescence assay. The binding of the immunoadhesin Fc-GPVI-nt dose dependently increased up to saturation levels in a concentration from 0.2 to 10 µg Fc-GPVI-nt (please see FIG. 5). The specificity was demonstrated by comparing binding of Fc-GPVI-nt with that of the empty immunoadhesin Fc-nt or the uncoated plastic surface (see FIG. 6).

Methods to Investigate Platelet Adhesion and Aggregation at Vascular Injury in Vivo as the Crucial Steps for Platelet Activation in Acute Vascular Events To test the biological significance of platelet-collagen interactions in the processes of adhesion to lesions in vivo, platelet-vessel wall interactions following vascular injury of the mouse carotid artery are assessed. Vascular injury to this important vascular bed may serve as a model for the first steps of arteriosclerosis such as the endothelial lesion in early stage arteriosclerosis or the plaque rupture in later stages of arteriosclerosis with the unmasking of collagen fibrils from the subendothelium. Moreover, this model allows the study of the subsequent complications of vascular injury. Small endothelial lesions lead to maximal activation of platelets with the following steps of platelet adhesion and aggregation. In further steps platelet aggregates can lead to embolism from the carotid artery with consecutive ischemic cerebral stroke. Thus, this experimental setup serves as a relevant in vivo model for a subgroup of patients with unstable atherosclerosis involving plaque rupture and endothelial lesions leading to acute coronary syndrome and stroke.

Figure 1B:
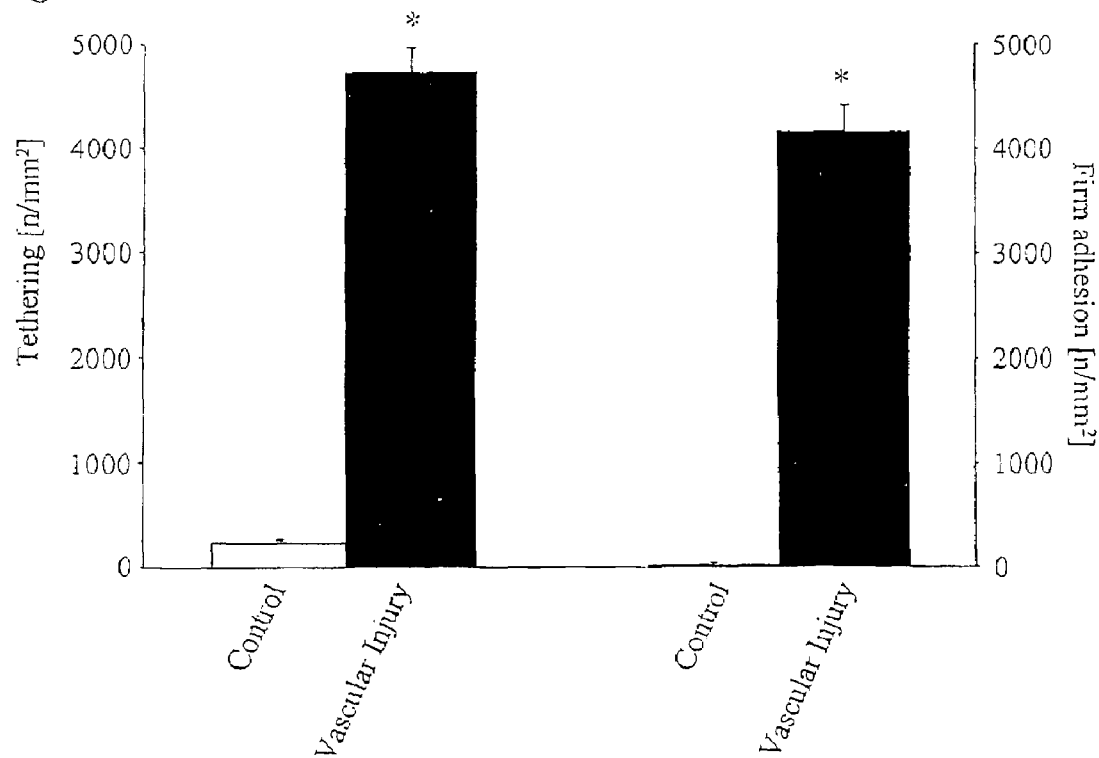

Vigorous ligation of the carotid artery for 5 min consistently causes complete loss of the endothelial cell layer and initiates platelet adhesion at the site of injury, as assessed by scanning electron microscopy (FIG. 1a). In vivo fluorescence microscopy may be used to directly visualize and quantify the dynamic process of platelet accumulation following vascular injury. Numerous platelets are tethered to the vascular wall within the first minutes after endothelial denudation (4620±205 platelets/mm$^2$). Virtually all platelets establishing contact with the subendothelium exhibit initially a slow surface translocation of the "stop-start" type (Savage, B., Saldivar, E. & Ruggeri, Z. M. Initiation of platelet adhesion by arrest onto fibrinogen or translocation on von Willebrand factor. *Cell* 1996; 84, 289-297). While we observed transition from initial slow surface translocation to irreversible platelet adhesion in 88% of all platelets (4182±253 platelets/mm$^2$) (FIG. 1b), platelet arrest remains transient in only 12% (543±32 platelets/mm$^2$). Once firm arrest is established, adherent platelets recruit additional platelets from the circulation, resulting in aggregate formation (FIG. 1c). Similar characteristics of platelet recruitment are obtained with immobilized collagen in vitro. In contrast, only few platelets are tethered to the intact vascular wall under physiological conditions (P<0.05 vs. vascular injury) and virtually 100% of these platelets are displaced from the vascular wall without firm arrest (P<0.05 vs. vascular injury, FIG. 1a-c).

Identification of GP VI as a Novel and Relevant Target Protein in Platelets for Vascular Injury In Vivo The high complexity of the platelet-vessel wall interaction which involves a variety of different receptors and signaling pathways makes the in vivo inhibition of this process very difficult. Besides GPIb-V-I-X and $\alpha_{IIb}\beta_3$ integrin which interact indirectly with collagen via von Willebrand factor (vWF), a large number of collagen receptors have been identified on platelets, including most importantly $\alpha_2\beta_1$ integrin (Santoro, S. A. Identification of a 160,000 dalton platelet membrane protein that mediates the initial divalent cation-dependent adhesion of platelets to collagen. *Cell* 1986; 46, 913-920), GPV (Moog, S. et al. Platelet glycoprotein V binds to collagen and participates in platelet adhesion and aggregation. *Blood* 2001; 98, 1038-1046), and GPVI (Moroi, M., Jung, S. M., Okuma, M. & Shinmyozu, K. A patient with platelets deficient in glycoprotein VI that lack both collagen-induced aggregation and adhesion. *J. Clin. Invest* 84, 1440-1445). Amidst several reports on different signaling systems which play a role in vitro, also GPVI has now been discussed (Gibbins, J. M., Okuma, M., Farndale, R., Baames, M. & Watson, S. P. Glycoprotein VI is the collagen receptor in platelets which underlies tyrosine phosphorylation of the Fc receptor gamma-chain. *FEBS Lett.* 1997; 413, 255-259; Nieswandt, B. et al., Long-term antithrombotic protection by in vivo depletion of platelet glycoprotein VI in mice. *J. Exp. Med.* 2001; 193, 459-469, Nieswandt, B. et al. Glycoprotein VI but not α2β1 integrin is essential for platelet interaction with collagen. *EMBO J.* 2001; 20, 2120-2130).

To directly test the in vivo relevance of platelet-collagen interactions in arterial thrombus formation, we inhibited or deleted GPVI in vivo. The monoclonal antibody (mAb) JAQ1 blocks the major collagen-binding site on mouse GPVI (Schulte, V. et al. Evidence for two distinct epitopes within collagen for activation of murine platelets. *J. Biol. Chem.*

Figure 2A:
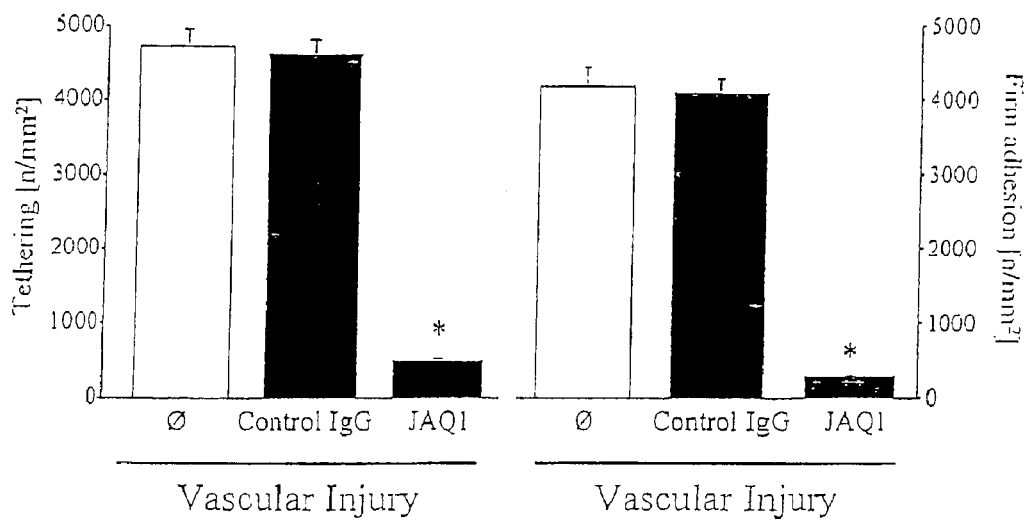
FIG. 2 Inhibition of GPVI abrogates platelet adhesion and aggregation after vascular injury. (a) Platelet adhesion following vascular injury was determined by intravital videofluorescence microscopy. Fluorescent platelets were preincubated with 50 µg/ml anti-GPVI (JAQ1) Fab fragments or control rat IgG. Platelets without mAb preincubation served as control. The left and right panels summarize transient and firm platelet adhesion, respectively. Mean±s.e.m., n=8 each group, asterisk indicates significant difference compared to control, P<0.05. (b) illustrates the percentage of platelets establishing irreversible adhesion after initial tethering/slow surface translocation is. (c) Platelet aggregation following vascular injury in vivo. Aggregation of platelets preincubated with tyrodes, irrelevant rat IgG, or anti-GPVI Fab (JAQ1) was assessed by fluorescence microscopy as described. Mean±s.e.m., n=8 each group, asterisk indicates significant difference compared to control, P<0.05. (d) The photomicrographs show representative in vivo fluorescence microscopy images illustrating platelet adhesion in the absence or presence of anti-GPVI Fab (JAQ1) or control IgG.
Figure 2B:
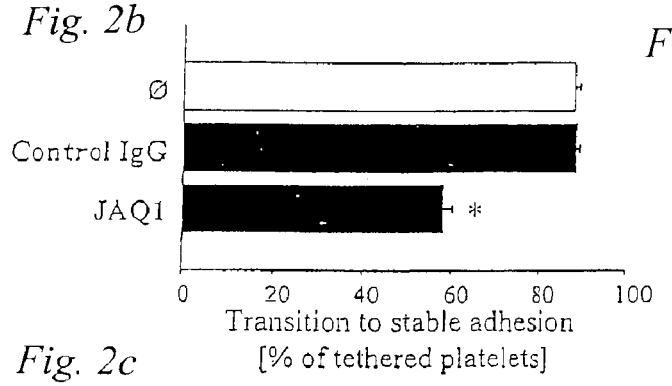
Figure 2C:
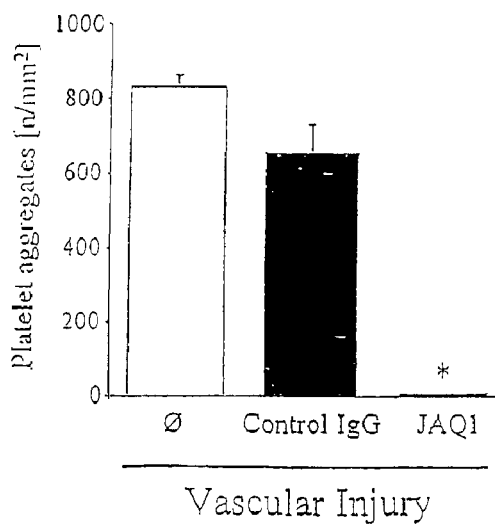
Figure 2D:
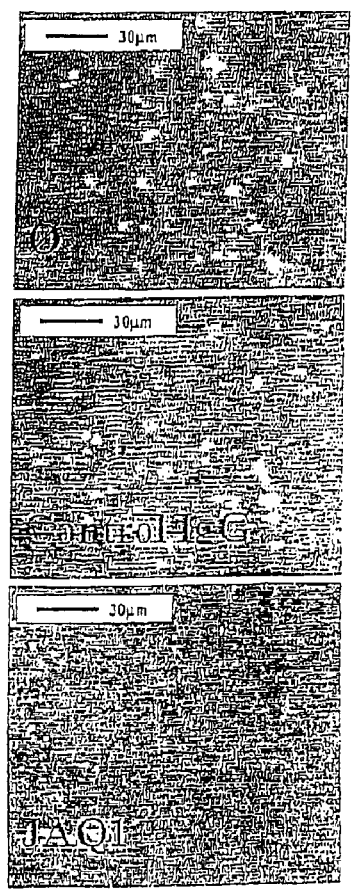

2001; 276, 364-368) and almost completely inhibits firm platelet adhesion to immobilized fibrillar collagen under high shear flow conditions (Nieswandt, B. et a. Glycoprotein VI but not alpha2beta1 integrin is essential for platelet interaction with collagen. *EMBO J.* 2001; 20, 2120-2130). To study the significance of GPVI-collagen interactions in the dynamic process of platelet adhesion/aggregation in arterial thrombus formation, mice received syngeneic, fluorescence-tagged platelets pre-incubated with JAQ1 Fab fragments or isotype-matched control IgG and carotid injury was induced as described above. Very unexpectedly, we found that the inhibition of GPVI reduced initial platelet tethering following endothelial denudation in the common carotid artery by 89% (P<0.05 vs. control IgG, FIG. 2a), a process thought to be mediated mainly by GPIbα interaction with immobilized vWF (Goto, S., Ikeda, Y., Saldivar, E. & Ruggeri, Z. M. Distinct mechanisms of platelet aggregation as a consequence of different shearing flow conditions. *J. Clin. Invest.* 1998; 101, 479-486; Sixma, J. J., van Zanten, G. H., Banga, J. D., Nieuwenhuls, H. K. & de Groot, P. G. Platelet adhesion. *Semin. Hematol.* 1995; 32, 89-98). Furthermore, stable platelet arrest was reduced by 93% by JAQ1 (FIG. 2a). We observed transition from initial tethering/slow surface translocation to irreversible platelet adhesion in only 58% of those platelets establishing initial contact with the subendothelial surface (compared to 89% with control IgG-pretreated platelets, P<0.05, FIG. 2b). Aggregation of adherent platelets was virtually absent following pretreatment of platelets with JAQ1 Fab fragments, but not in the controls (P<0.05 vs. control, FIGS. 2c and d). These data demonstrated that direct platelet-collagen interactions are crucial for initial platelet tethering and subsequent stable platelet adhesion and aggregation at sites of vascular injury. Furthermore, these findings show that GPVI is a key regulator in this process, while other surface receptors, most importantly GPIb-V-IX and $\alpha_2\beta_1$, are not sufficient to initiate platelet adhesion and aggregation on the subendothelium in vivo.

Figure 3A:
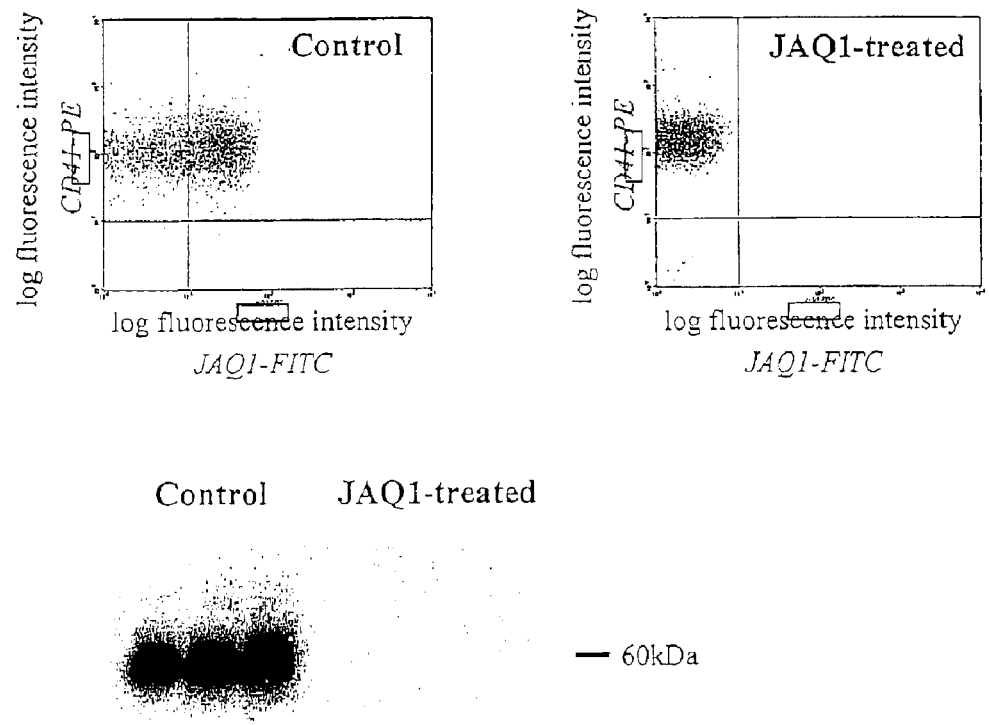
FIG. 3 Platelet adhesion following endothelial denudation in GPVI-deficient mice. (a) JAQ1-treated mice lack GPVI. Upper panels: Platelets from mice pretreated with irrelevant control IgG (left) or anti-GPVI (JAQ1) (right) were incubated with FITC-labeled JAQ1 and PE-labeled anti-mouse CD41 for 10 min at room temperature and directly analyzed on a FACScan™. A representative dot blot of 3 mice per group is presented. Lower panel: Whole platelet lysates from three control IgG or JAQ1-treated mice were separated by SDS-PAGE under non-reducing conditions and immunoblotted with FITC-labeled JAQ1, followed by incubation with HRP-labeled rabbit-anti-FITC mAb. (b) Scanning electron micrographs of carotid arteries 2 hrs after vascular injury in control animals (upper panels) or GPVI-depleted mice (lower panels). Endothelial denudation induced platelet adhesion and platelet aggregation in control animals. In contrast, only very few platelets attached along the damaged vessel wall in GPVI-depleted mice. Subendothelial collagen fibers are visible along the denuded area. (c) Platelet tethering and firm platelet adhesion, (d) transition from initial tethering to stable arrest (percentage of tethered platelets), and (e) platelet aggregation following vascular injury of the carotid artery was determined in GPVI-deficient (JAQ1-pretreated mice) or control IgG-pretreated mice (for details see Materials and Methods). The panels summarize platelet adhesion (transient and firm) and platelet aggregation in eight experiments per group. Mean±s.e.m., asterisk indicates significant difference compared to control IgG, P<0.05. (f) The photomicrographs show representative in vivo fluorescence microscopy images illustrating platelet adhesion in GPVI-deficient (JAQ1) and control IgG-treated mice.

To exclude the possibility that this effect is based on steric impairment of other receptors, e.g. GPIb-V-IX, by surface-bound JAQ1, we generated GPVI-deficient mice by injection of JAQ1 five days prior to vascular injury. As reported previously, such treatment induces virtually complete loss of GP VI e.g. by internalization and proteolytic degradation of GPVI in circulating platelets, resulting in a "GPVI knock out"-like phenotype for at least two weeks (Nieswandt, B. et al. Long-term antithrombotic protection by in vivo depletion of platelet glycoprotein VI in mice. *J. Exp. Med.* 2001; 193, 459-469). As illustrated in FIG. 3a, GPVI was undetectable in platelets from JAQ1-treated mice on day 5 after injection of 100 μg/mouse JAQ1, but not control IgG, while surface expression and function of all other tested receptors, including GPIb-V-IX, $\alpha_{IIb}\beta_3$, and $\alpha_2\beta_1$ was unchanged in both groups of mice, confirming earlier results (data not shown and Nieswandt, B. et al., Long-term antithrombotic protection by in vivo depletion of platelet glycoprotein VI in mice. *J. Exp. Med.* 2001; 193, 459-469).

Figure 3B:
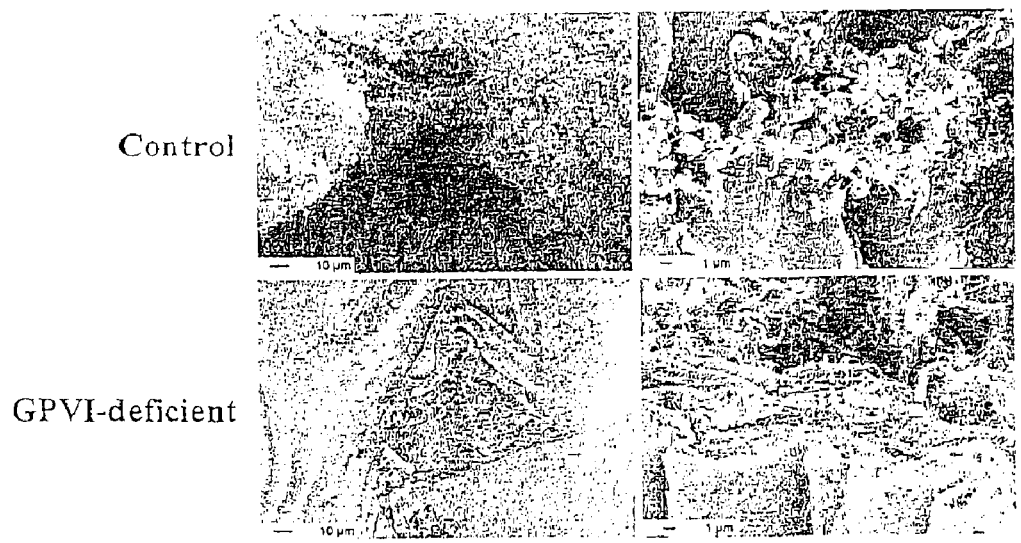
Figure 3C:
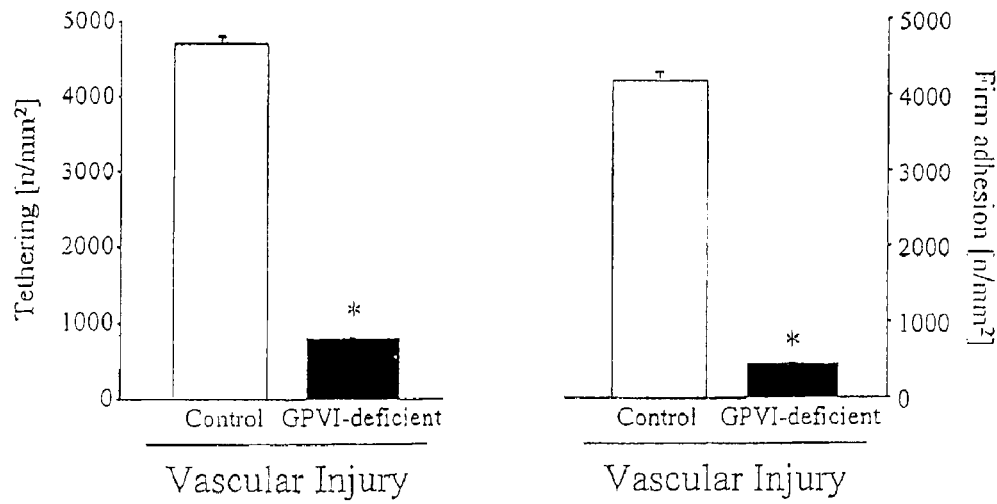
Figure 3D:
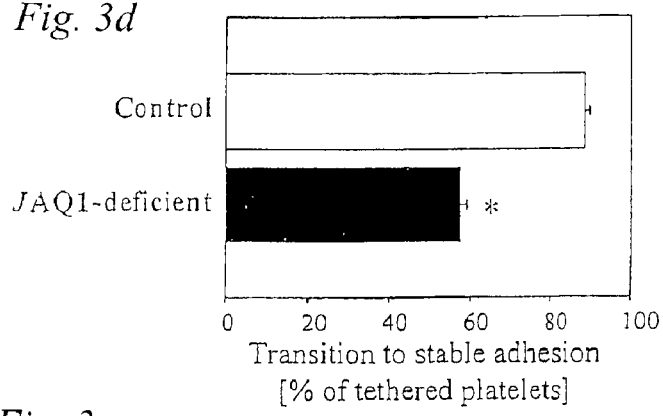
Figure 3E:
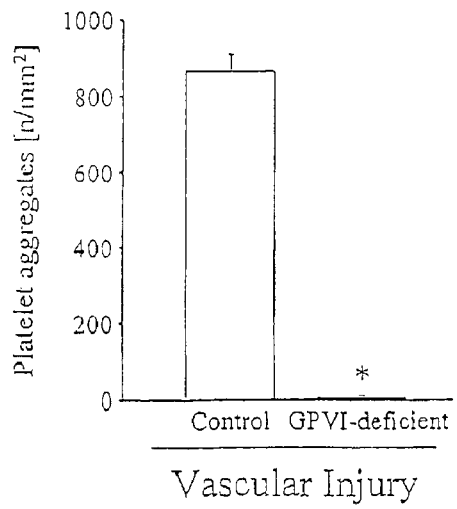
Figure 3F:
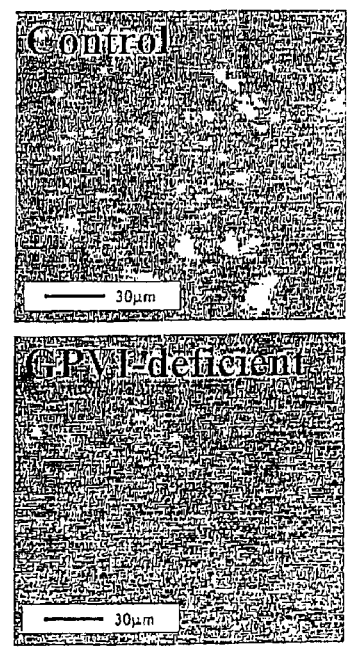

As shown by scanning electron microscopy, platelet adhesion and aggregation following endothelial denudation of the common carotid artery is virtually absent in GPVI-deficient, but not in IgG-pretreated mice (FIG. 3b). Next, in vivo video fluorescence microscopy was used to define platelet adhesion dynamics following vascular injury in GPVI-deficient mice (FIG. 3c-f).

The loss of GPVI significantly reduces tethering/slow surface translocation of platelets at the site of vascular injury (by 83% compared to IgG-pretreated mice, P<0.05). This GPVI-independent slow surface translocation requires vWF-GPIbα-interaction, since it is abrogated by preincubation of the platelets with Fab fragments of a function blocking mAb against GPIbα (p0p/B) confirming the critical role of GPIbα in this process (not shown). In the absence of GPVI, stable platelet adhesion is reduced by approximately 90% compared to the (IgG-treated) control, while aggregation of adherent platelets is virtually absent (FIG. 3b-f). We saw transition from platelet tethering to stable platelet adhesion in only 58% of all platelets initially tethered to the site of injury (compared to 89% with control mAb-pretreated platelets, P<0.05, FIG. 3d), indicating that GPIbα-dependent surface translocation is not sufficient to promote stable platelet adhesion and subsequent aggregation.

The profound inhibition of platelet tethering by GPVI blockade was surprising and suggested a previously unrecognized function of this receptor in the very Initial phase of firm platelet adhesion to vascular lesions. Fibrillar collagen is a major constituent of human atherosclerotic lesions (Rekhter, M. D. Collagen synthesis in atherosclerosis: too much and not enough. *Cardiovasc. Res.* 1999; 41, 376-384; Rekhter, M. D. et al. Type I collagen gene expression in human atherosclerosis. Localization to specific plaque regions. *Am. J. Pathol.* 1993; 143, 1634-1648); enhanced collagen synthesis (by intimal smooth muscle cells and fibroblasts) significantly contributes to luminal narrowing in the process of atherogenesis (Opsahl, W. P., DeLuca, D. J. & Ehrhart, L. A. Accelerated rates of collagen synthesis in atherosclerotic arteries quantified in vivo. *Arteriosclerosis* 1987; 7, 470-476). Plaque rupture or fissuring (either spontaneously or following balloon angioplasty) results in exposure of collagen fibrils to the flowing blood.

The invention teaches for the first time that such subendothelial collagens are the major trigger of arterial thrombus formation and reveal an unexpected function of the collagen receptor GPVI in platelet recruitment to the injured vessel wall. The processes of platelet tethering and slow surface translocation under conditions of elevated shear are known to largely depend on GPIbα interaction with immobilized vWF. This interaction is, however, not sufficient to establish inital platelet-vessel wall interactions in vivo as functional GPVI is also required (FIGS. 2 and 3). Thus, both GPIbα and GPVI must act in concert to recruit platelets to the subendothelium. During platelet tethering, ligation of GPVI can shift $\alpha_{IIb}\beta_3$ and $\alpha_2\beta_1$ integrins from a low to a high affinity state. Both $\alpha_{IIb}\beta_3$ and $\alpha_2\beta_1$ then act in concert to promote subsequent stable arrest of platelets on collagen, while $\alpha_{IIb}\beta_3$ is essential for subsequent aggregation of adherent platelets. Thus, ligation of GPVI during the initial contact between platelets and subendothelial collagen provides an activation signal that is essential for subsequent stable platelet adhesion and aggregation. Importantly, occupation or lateral clustering of GPIbα (during GPIbα-dependent surface translocation), which induced low levels of $\alpha_{IIb}\beta_3$ integrin activation in vitro (Kasirer-Friede, A. et al. Lateral clustering of platelet GP Ib-IX complexes leads to up-regulation of the adhesive function of Integrin αIIbβ3. *J. Biol. Chem.* 2002; Vol 277: 11949-11956), is not sufficient to promote platelet adhesion in vivo.

The invention therefore has identified an essential receptor for inhibiting platelet attachment to the subendothelium. An antibody which blocks the interaction of GPVI with exposed collagen can specifically inhibit all major phases of thrombus formation, i.e. platelet tethering, firm adhesion, and aggregation at sites of arterial injury (e.g. during acute coronary syndromes). The very profound protection that was achieved by inhibition or depletion of GPVI establishes the importance of selective pharmacological modulation of GPVI-collagen interactions to control the onset and progression of pathological atherosclerotic lesions.

Following rupture of the atherosclerotic plaque, exposure of subendothelial collagen is the major trigger that initiates platelet adhesion and aggregation at the site of injury, followed by arterial thrombosis (1;24;25). The platelet glycoprotein GPVI, which has been cloned recently (5;6), has been identified by the invention to be the major platelet collagen receptor (4), mediating platelet adhesion both in vitro (22) and under (patho-)physiological conditions in vivo (3). Therefore, inhibition of GPVI prevents platelet recruitment and arterial thrombosis in patients with advanced atherosclerosis as shown by the present invention by the inhibitory activities of the specific fusion protein Fc-GPVI-nt on platelet adhesion in vitro and in vivo.

The Fc-GPVI-nt fusion protein is expressed in HELA cells using an adenoviral expression system to obtain soluble Fc-GPVI-nt. Characterization of the soluble forms of GPVI revealed that Fc-GPVI-nt is secreted as dimer with a molecular mass of approximately 160 kDa. Consistently, Miura and co-workers recently reported that GPVI-Fc-dimer is present as a dimer, in which two GPVI-Fc-dimer molecules are cross-linked by disulfide bonds formed from the Cys in the Fc domain of each molecule (21). Importantly, only the dimeric form of GPVI, but not monomers of the extracellular domain of GPVI, has been reported to exhibit collagen binding affinity and to attenuate collagen-induced platelet aggregation (21).

Binding assays were performed to define GPVI-Fc-dimer-collagen interaction. Soluble GPVI binds to immobilized collagen in a saturable manner. GPVI-Fc-dimer binding to fibrillar collagen was highly specific, since it did not occur to immobilized vWF or BSA. Further, GPVI binding to immobilized collagen could be inhibited by soluble collagen. High concentrations of soluble collagen were required to block GPVI-Fc-dimer binding, indicating the fusion protein binds immobilized collagen with high affinity. Correspondingly, a high association and dissociation constant ($K_D$ approximately $5.8 \times 10^{-7}$ M) has been reported for the GPVI-collagen interaction (21).

Soluble Fc-GPVI-nt has been demonstrated earlier to attenuate platelet activation and aggregation in response to collagen or convulxin, a snake toxin, which binds to GPVI with high affinity (6;21;27). Apart from platelet aggregation, GPVI is critically involved in the process of platelet adhesion to collagen (3;22). In the present study, we, therefore, tested the effects of Fc-GPVI-nt on platelet adhesion under physiological flow conditions in vitro. We show that soluble Fc-GPVI-nt dose-dependently inhibits platelet adhesion under low and high shear conditions in vitro. In the presence of Fc-GPVI-nt, but not of control Fc peptide, aggregation of adherent platelets was virtually absent, indicating that GPVI contributes to the processes of both platelet adhesion and subsequent activation by immobilized collagen. GPVI confers collagen responses (i.e. adhesion and aggregation) in a receptor density-dependent fashion (22). Correspondingly, it has been reported that a more than 50% reduction in GPVI expression transfected RBL-2H3 cells is associated with a lack of collagen-induced aggregation in these cells (8;22). Since a low variability in the GPVI receptor density has been reported albeit in a small sample population (22), one might expect that inhibition of approx. 50% of collagen-GPVI bonds is sufficient to attenuate platelet recruitment to exposed collagen. In the present study doses of 1 mg/kg Fc-GPVI-nt were required to induce significant inhibition of platelet adhesion underflow, supporting the notion that multiple GPVI binding sites are available in each collagen fibril. Similar amounts of a function blocking anti-GPVI antibody were required to attenuate platelet-vessel wall injury in vivo (3).

Fibrillar collagen is a major constituent of the normal vessel wall but also of atherosclerotic lesions (28). Rupture or fissuring of the atherosclerotic plaque results in exposure of collagen fibrils to circulating platelets. As reported earlier, GPVI-collagen interactions are essentially involved in arterial thrombus formation following vascular injury (3). Here we demonstrate the in vivo effects of soluble Fc-GPVI-nt on platelet recruitment after arterial injury. Endothelial denudation was induced by reversible ligation of that carotid artery and the dynamic process of platelet attachment was monitored by intravital videofluorescence microscopy as described (3). We demonstrate for the first time in vivo that soluble Fc-GPVI-nt attenuates stable platelet tethering, adhesion and platelet aggregation following endothelial denudation. Inhibition of platelet recruitment by Fc-GPVI-nt was dose-dependent. Apart from preventing stable arrest of platelets, Fc-GPVI-nt significantly reduced initial platelet tethering/slow surface translocation at sites of endothelial denudation. We have demonstrated earlier that inhibition of GPIba or of GPVI attenuate platelet tethering to a similar extent (3), supporting that GPVI and GPIbα interaction need to act in contact to promote platlet tethering to subendothelial collagen (2;29-31). In fact, the high "on"- and "off"-rates reported for the GPVI-ligand interaction (22) are consistent with the role of GPVI as a tethering receptor.

The present invenvention identifies Fc-GPVI-nt as an active ingredient of a medicament to attenuate arterial thrombosis following vascular injury. This concept is further supported by the observation that Fc-GPVI-nt is targeted to the exposed subendothelium at the site of vascular injury, as demonstrated by immunohistochemistry. This implicates that inhibition of GPVI-collagen interactions are likely to be restricted to the site of vascular injury, while a prolonged systemic inhibition of platelet function is limited by the expected short half-life of unbound Fc-GPVI-nt. In contrast, administration of monoclonal antibodies directed against GPVI inevitably leads to systemic inhibition of GPVI on all circulating platelets. In addition, Fc-GPVI-nt administration did not affect platelet counts. In contrast, anti-GPVI mAbs may eventually induce immune thrombocytopenia or a complete loss of GPVI on circulating platelets (14;32), hampering their use in clinical practice. Accordingly, Fc-GPVI-nt therapy will likely be associated with a lower risk of clinical hemorrhage, compared to anti-GPVI mAb-based strategies.

Platelet adhesion and aggregation at sites of vascular injury is crucial for hemostasis but may lead to arterial occlusion in the setting of atherosclerosis and precipitate diseases such as coronary thrombosis and myocardial infarction. The use of intravenous GPIIb-IIIa receptor inhibitors, has significantly improved the clinical success of patients undergoing coronary stenting (33-35). However, severe bleeding complications have been reported to hamper the outcome of patients treated with abciximab (36). The present invention demonstrates that inhibition of GPVI-collagen interactions by Fc-GPVI-nt was sufficient to significantly reduce platelet adhesion both in vitro and in vivo; however, the soluble form of GPVI only moderately prolonged tail bleeding times. Similarly, mild bleeding disorders have been reported in patients with GPVI-deficient platelets (37), indicating that coagulation and hemostasis are effective even in the complete absence of GPVI. In part this discrepancy may be due to the fact that inhibition or absence of GPVI does not interfere with platelet aggregation in response to platelet agonists other than collagen, e.g. ADP, tissue factor or thrombin. In contrast, direct inhibition of GPIIb-IIIa, e.g. by 7E3 or its humanized derivative, blocks fibrinogen binding to platelets, a process which is essential for platelet aggregation, and substantially attenuates platelet aggregation to most platelet agonist known thus far. Accordingly, Fc-GPVI-nt therapy are associated with a lower risk of clinical hemorrhage, compared to anti-GPIIb-IIIa-based strategies.

In conclusion, the present invention provides the first in vivo evidence that Fc-GPVI-nt attenuates platelet adhesion under flow in vitro and following endothelial denudation in the carotid artery of mice in vivo. This further supports the concept that GPVI-collagen interactions play a central role in all major phases of thrombus formation, i.e. platelet tethering, firm adhesion, and aggregation at sites of arterial injury (e.g. during acute coronary syndromes). The present invention further supports the concept that GPVI plays a major role in the progression of atherosclerosis. Moreover, the present invention shows for the first time the causal connection between GPVI and diabetes.

The invention will now be described in further detail with reference to the following specific examples.

EXAMPLES

Animals. Specific pathogen-free C57BL6/J mice were obtained from Charles River (Sulzfeld, Germany). For experiments, 12-weeks-old male mice were used. All experimental procedures performed on animals were approved by the German legislation on protection of animals.

Monoclonal antibodies. Monoclonal antibody (mAb) anti GPVI (JAQ1) and anti GPIbα (p0p/B) and Fab fragments from JAQ and p0p/B were generated as described (Bergmeier, W., Rackebrandt, K., Schroder, W., Zirngibl, H. & Nieswandt, B. Structural and functional characterization of the mouse von Willebrand factor receptor GPIb-IX with novel monoclonal antibodies. *Blood* 2000; 95, 886-893; Nieswandt, B., Bergmeier, W., Rackebrandt, K., Gessner, J. E. & Zirngibl, H. Identification of critical antigen-specific mechanisms in the development of immune thrombocytopenic purpura in mice. *Blood* 2000; 96, 2520-2527). Irrelevant control rat IgG was obtained from Pharmingen (Hamburg, Germany).

Generation of GPVI-Deficient Mice

To generate mice lacking GPVI, C57BL6/J wild-type mice were injected with 100 µg JAQ1 i.c. Animals were used for in vivo assessment of platelet adhesion on day 5 after mAb injection. Absence of GPVI expression on platelets was verified by Western blot analysis and flow cytometry.

Flow Cytometry

Heparinized whole blood, obtained from wild type C57BL6/J mice or GPVI-depleted mice was diluted 1:30 with modified Tyrodes-HEPES buffer (134 mM NaCl, 0.34 mM $Na_2HPO_4$, 2.9 mM KCl, 12 mM $NaHCO_3$, 20 mM HEPES, 5 mM glucose, and 1mM $MgCl_2$, pH 6.6). The samples were incubated with fluorophore-labeled mAb anti-GPVI (JAQ1) and anti-CD41 for 10 min at room temperature and directly analyzed on a FACScan™ (Becton Dickinson).

Cloning, viral expression and purification of soluble human and murine GPVI. To generate a soluble form of human GPVI, the extracellular domain of human GPVI was cloned and fused to the human immunoglobin Fc domain according to the following examples 1 to 3. Adenoviral constructs coding for the GPVI-Fc-fusion protein or control Fc were prepared to generate the recombinant protein. GPVI-Fc and control Fc were expressed as secreted soluble proteins using the human HELA cell line to prevent misfolding and non-glycosylation of the expressed proteins.

Example 1

Cloning of the Immunoadhesin of GP VI (Fc-GPVI-nt)

We generated an immunoadhesin of the GP VI receptor by generating a recombinant fusion protein of the n-terminal part of GP VI—which encodes the extracellular domain of GPVI—together with the Fc part of an IgG. The Fc was amplified from a human heart cgcggggcggccgcgagtccaaatct-tgtgacaaaac-3' (SEQ ID No. 3) and the reverse primer 5'-gcgggaagctttcatttacccggagacagggag-3' (SEQ ID No. 4). The PCR reaction was performed at 58° C. annealing temperature and 20 cycles with the Expand High Fidelity PCR System (Roche Molecular Biochemicals, Mannheim, Germany). The PCR fragment was cloned in the plasmid pADTrack CMV with NotI/HindIII and the sequence was checked by sequencing (MediGenomix, Martinsried, Germany).

For cloning of the extracellular domain of the human GPVI RNA from cultured megakaryocytes was isolated (RNeasy Mini Kit; Qiagen, Hilden, Germany) according to the manufacter's protocol and reverse transcription was performed (Omniscript RT Kit; Qiagen) with 2 µg RNA at 37° C. overnight. 100 ng of the reaction was used as a template in PCR amplification of the hGPVI with the primer 5'-gcggggagatc-taccaccatgtctccatccccgacc-3' (SEQ ID No. 5) and 5'-cgcggggcggccgccgttgcccttggtgtagtac-3' (SEQ ID No. 6). The PCR reaction was performed at 54° C. annealing temperature and 24 cycles with the Expand High Fidelity PCR System (Roche Molecular Biochemicals, Mannheim, Germany). The PCR fragment was cloned in the plasmid pDATrack CMV Fc with BglII/NotI and the sequence was checked by sequencing.

Construction of a Monomeric Fusion Protein Based on Fc-GPVI-Nt

The Fc monomer fragment was amplified by PCR using the primer pair 5'-cgcggggcggccgcccagcacctgaactcctg-3' (SEQ ID No. 7) and 5'-cgcggggatatctcatttacccggagacagggag-3' (SEQ ID No. 8) and pADTrack CMV gpVI-Fc as a template. The PCR reaction was performed at 58° C. annealing temperature and 20 cycles with the Expand High Fidelity PCR System (Roche Molecular Biochemicals, Mannheim, Germany). The Fc monomer PCR fragment (NotI/EcoRV) and the gpVI fragment from pADTrack CMV gpVI-Fc (BglII/NotI) were cloned as described above.

Example 2

Generation of the Adenovirus for Fc-GPVI-nt (Ad-Fc-GPVI-nt)

The plasmid pADTrack CMV Fc-GPVI-nt was linearized with Pmel (New England Biolabs, Beverly, Mass.) overnight, dephosphorylated and purified (GFX DNA and Gel Purification Kit; Amersham Pharmacia Biotech, Uppsala, Sweden). For recombination electrocompetent *E. coli* BJ5183 (Stratagene, La Jolla, Calif.) were cotransformed with 1 µg of the linearized plasmid and 0.1 µg pAdeasy1 at 2500 V, 200 Ω and 25 µFD (*E. coli*-pulser; Biorad, Heidelberg, Germany), plated and incubated overnight at 37° C. The colonies were checked after minipreparation of the plasmid-DNA with Pacl and the positive clones were retransformed in *E. coli* DH5α.

For transfection (Effectene Transfection reagent; Qiagen, Hilden, Germany) of 293 cells plasmid-DNA was digested with Pacl. The cells were cultured for 7 days and harvested by scraping and centrifugation. The pellet was resuspended in Dulbecco's PBS and the cells were lysed by four repetitive freezing (−80° C.) and thawing (37° C.) cycles. Cell debris was removed by centrifugation and the lysate stored at −80° C.

For plaque selection of recombinant virus 293 cells are infected in Dulbeccos PBS for 1 hour at room temperature under gentle agitation with different serial dilutions of lysate from transfection. Following the infection, the cells are overlayed with growth medium containing 0.5% agarose (1:1 mix of modified Eagles medium 2×, Gibco Life Technologies #21935, supplemented with 20% serum, 2×Pencillin/Streptomycin, 2×L-glutamin and agarose in water 1%, Seacam). 5-14 days post infection the cell layer was monitored for formation of plaques which were picked using a pasteur pipett, resuspended in 0.5 ml Dulbeccos PBS and stored at −80° C. The plaques were used for further amplification rounds on 293 cells.

Construction of Human gpVI-Fc Monomer Expressing Stable CHO

The monomer expressing cells were generated in accordance with examle 2.

Example 3

Fc-GPVI-nt Protein and Fc Control Immunoadhesin Purification

The culture supernatant of Ad-Fc-GPVI-nt-infected Hela cells was collected 2 days after infection, centrifugated (3800 g, 30 min, 4° C.) and filtrated (0.45 μm). The immunoadhesin was precipitated by addition of 1 vol. ammonium sulfate (761 g/l) and stirred overnight at 4° C. The proteins were pelleted by centrifugation (3000 g, 30 min, 4° C.), dissolved in 0.1 Vol PBS and dialysed in PBS overnight at 4° C. The protein solution was clarified by centrifugation (3000 g, 30 min, 4° C.) and loaded on a protein A column (HiTrap™ protein A HP, Amersham Pharmacia Biotech AB, Uppsala, Sweden). The column was washed with binding buffer (20 mM sodium phoshate buffer pH 7.0, 0.02% $NaN_3$) until $OD_{280}$<0.01 and eluted with elution buffer (100 mM glycine pH 2.7). The eluted fractions were neutralized with neutralisation buffer (1 M Tris/HCl pH 9.0, 0.02% $NaN_3$), pooled, dialysed in PBS overnight at 4° C., aliquotated and frozen at −20° C.

The molecular mass of Fc-GPVI-nt protein was ~80 kDa under reducing conditions in SDS-PAGE, as detected by Coomassie blue stain or by immunoblotting with peroxidase-conjugated goat anti-human Fc antibody or by the anti-GPVI mAb 5C4 (FIG. 1a, upper and middle panel). In contrast, a ~160 kDa protein was identified under non-reducing conditions (FIG. 1a, lower panel), supporting the notion that GPVI-Fc is obtained solely as dimer (21).

Example 4

GP VI Inhibitor Screening Assay

ELISA plates (Immulon2 HB, Dynx Technologies, Chantilly, Va.) were coated overnight at 4° C. with 1 μg/well collagen (type I bovine; BD Bioscience, Bedford, Mass.) in 100 μl 50 mM Tris/HCl pH 8.0. The plate was washed with 250 μl/well PBS/0.05% Tween 20 (PBST) twice and blocked with 250 μl/well Roti-Block (Roth, Karlsruhe, Germany) overnight. The plate was washed with 250 μl/well PBST twice, 100 μl Fc-GPVI-nt in PBST was added (optimal 2 μg/well) and the plate was incubated for 1 h at room temperature. After 5-fold washing with 250 μl PBST 100 μl peroxidase-conjugated goat anti-humanIgG antibody (Dianova, Hamburg, Germany) was added in a dilution of 1:10000 and incubated for 1 h at room temperature. After repeated washing with 250 μl PBST 100 μl detection reagent (BM Blue POD Substrate; Roche, Mannheim, Germany) was added and incubated for 15 min. The reaction was stopped by the addition of 100 μl 1 M $H_2SO_4$ and the plate was measured at 450 nm against the reference wavelength 690 nm. To screen for potential inhibitors, test compounds are added to the incubation in 100 μl PBST at various concentrations.

Example 5

Platelet Aggregation and Luminometry

Platelet aggregation ex vivo and in vitro was evaluated by optical aggregometry in citrated blood samples at 37° C. using a two channel Chronolog aggregometer (Nobis, Germany). Platelet-rich plasma was prepared from citrated whole blood by centrifugation (200 g for 20 min). The final platelet count was adjusted to $2 \times 10^8$ platelets/ml with autologous plasma. After adjustment of the baseline, collagen (type I, bovine) from 0.2 to 4 μg/ml was added and aggregation was recorded for 5 min. Simultaneously, release of ATP was recorded using the firefly luminometer method. Incubation with the monoclonal GP VI antibody JAQ 1 was performed for 15 min with 50 μg/ml antibody.

Example 6

In Vitro Platelet Adhesion Assay for GP VI/Collagen Interaction

From ACD (20% final concentration) blood platelet rich plasma was prepared and adjusted to a final concentration of $10^8$ platelets/ml by Hepes Tyrode (pH 6.5). Coverslips were coated with monolayers of various adhesive proteins (Collagen, vWF) at different concentrations. Perfusion studies were carried out in a perfusion chamber generated from glass coverslips. Perfusion was performed at shear rates of 500/s representing low-medium flow and 2000/s representing high shear rates. Adhesion was measured at 37° C. for 20 minutes and then drawn through the chamber at fixed wall shear rates for 5 minutes using an automated syringe pump. After perfusion the coverslips were gently washed with Hepes Tyrode, taken from the chamber. Coverslips were repeatedly washed with Hepes Tyrode to completely remove adhesive platelets. The platelets in suspension were quantitatively analysed by FACS measurements. The analysis of the functional status of platelets was further assessed by analysis of surface marker expression (CD 41; CD 61 and CD 62 P) according to the standard flow cytometry protocol.

Example 7

Preparation of Platelets for Intravital Microscopy

Platelets (wild type, or GPVI-deficient) were isolated from whole blood as described (Massberg, S. et al. Platelet-endothelial cell interactions during ischemia/reperfusion: the role of P-selectin. *Blood* 1998; 92, 507-515) and labeled with 5-carboxyfluorescein diacetat succinimidyl ester (DCF). The DCF-labeled platelet suspension was adjusted to a final concentration of $200 \times 10^6$ platelets/250 μl. Where indicated, fluorescent wild type platelets were preincubated with 50 μg/ml anti-GPVI (JAQ1) Fab fragments, or anti GPIbα (p0p/B) Fab fragments for 10 min. Subsequently, the pretreated platelets together with the Fab fragments were infused into wild type recipient mice and platelet adhesion was assessed prior to and after carotid injury by in vivo video microscopy, as described below.

Example 8

Assessment of Platelet Adhesion and Aggregation by Intravital Microscopy

Wild type C57BL6/J or GPVI-deficient mice were anesthetized by intraperitoneal injection of a solution of midazolame (5 mg/kg body weight, Ratiopharm, Ulm, Germany), medetomidine (0.5 mg/kg body weight, Pfizer, Karlsruhe, Germany), and fentanyl (0.05 mg/kg body weight, CuraMed Pharma GmbH, Munich, Germany). Polyethylene catheters (Portex, Hythe, England) were implanted into the right jugular vein and fluorescent platelets ($200 \times 10^6/250$ µl) were infused intravenously. The right common carotid artery was dissected free and ligated vigorously near the carotid bifurcation for 5 min to induce vascular injury. Prior to and following vascular injury, the fluorescent platelets were visualized in situ by in vivo video microscopy of the right common carotid artery. Platelet-vessel wall interactions were monitored using a Zeiss Axiotech microscope (20× water immersion objective, W 20×/0.5, Zeiss) with a 100 W HBO mercury lamp for epi-illumination. All video-taped images were evaluated using a computer-assisted image analysis program (Cap Image 7.4, Dr. Zeintl, Heidelberg, Germany). Transiently adherent platelets were defined as cells crossing an imaginary perpendicular through the vessel at a velocity significantly lower than the centerline velocity; their numbers are given as cells per $mm^2$ endothelial surface. The number of adherent platelets was assessed by counting the cells that did not move or detach from the endothelial surface within 10 seconds. The number of platelet aggregates at the site of vascular injury was also quantified and is presented per $mm^2$.

Example 9

Scanning Electron Microscopy

Following intravital videofluorescence microscopy, the carotid artery was perfused with PBS (37° C.) for 1 min, followed by perfusion fixation with phosphate-buffered glutaraldehyde (1% vol/vol). The carotid artery was excised, opened longitudinally, further fixed by immersion in 1% PBS-buffered glutaraldehyde for 12 hours, dehydrated in ethanol, and processed by critical point drying with $CO_2$. Subsequently, the carotid artery specimens were oriented with the lumen exposed, mounted with carbon paint, sputter coated with platinum, and examined using a field emission scanning electron microscope (JSM-6300F, Jeol Ltd., Tokyo, Japan).

Example 10

Assessment of Fc-GPVI-nt binding to immobilized collagen. The binding of Fc-GPVI-nt to immobilized collagen was determined. ELISA plates (Immulon2 HB, Dynx Technologies, Chantilly, Va.) were coated over night at 4° C. with 1 µg collagen (typl bovine; BD Bioscience, Bedford, Mass.) in 100 µl coating buffer (1.59 g/l $Na_2CO_3$, 2.93 g/l $NaHCO_3$, 0.2 g/l $NaN_3$, pH 9.6). The plates were washed with 250 µl/well PBS/0.05% Tween 20 (PBST) twice and blocked with 250 µl/well Roti-Block (Roth, Karlsruhe, Germany) over night. The plates were washed with 250 µl/well PBST twice, then 3.0, 6.0, 12.5, 25.0, 50.0 or 100 µg/ml Fc-GPVI-nt in PBST was added and the plate was incubated for 1 hr at room temperature. Where indicated, Fc-GPVI-nt (20 µg/ml) was preincubated for 10 min with soluble collagen. After incubation the plates were washed 5 times with 250 µl PBST and peroxidase-conjugated goat anti-human IgG antibody Fcγ fragment specific (109-035-098; Dianova, Hamburg, Germany) was added in a dilution of 1:10.000 and incubated for 1 hr at room temperature. After 5 fold washing with 250 µl PBST 100 µl detection reagent (BM Blue POD Substrate; Roche, Mannheim, Germany) was added and incubated up to 10 min. The reaction was stopped by the addition of 100 µl 1 M $H_2SO_4$ and the plate was measured at 450 nm against reference wavelength 690 nm.

Fc-GPVI-nt showed a dose-dependent and saturable binding to immobilized collagen (FIG. 9b). Half maximal collagen binding was observed at a final Fc-GPVI-nt concentration of 6.0 µg/ml. Binding of GPVI-Fc did not occur to BSA, vWF (FIG. 9c, left panel) or Poly-L-Lysin (not shown), supporting the specificity of Fc-GPVI-nt binding. Moreover, we did not detect any significant binding of the control Fc protein lacking the external GPVI domain under identical conditions (FIG. 9c, right panel).

To further address the specificity of GPVI-binding, we the ability of solubilized fibrillar collagen to compete with immobilized collagen for the association with Fc-GPVI-nt was tested. Soluble collagen inhibited Fc-GPVI-nt-binding to immobilized collagen in a dose-dependent manner (FIG. 9d). A concentration of 100 µg/ml soluble collagen was required to reduce Fc-GPVI-nt binding by more than 50%. Together, these data indicated that Fc-GPVI-nt binding to collagen is specific and characterized by high affinity.

Example 11

Generation of monoclonal antibody against human GPVI. Monoclonal antibodies were generated essentially as described (17). Lou/C rats were immunized with the adenovirally expressed human Fc-GPVI-nt fusion protein. Screening of hybridoma supernatants was performed in a solid-phase immunoassay using Fc-GPVI-nt or FC lacking the GPVI domain. Screening identified the supernatant of hybridoma 5C4 to bind specifically to Fc-GPVI-nt but not to Fc lacking the external GPVI domain. The immunoglobulin type was determined with rat Ig class (anti-IgM) and IgG subclass-specific mouse mAbs. The monoclonal antibodies were purified using Protein G-Sepharose columns. Antibody specificity of 5C4 was verified by immunoblotting against Fc-GPVI-nt and control Fc. 5C4 monoclonal antibody detected adenovirally expressed Fc-GPVI-nt but not control Fc. Furthermore, human GPVI was recovered in lysates obtained from human platelets. In addition, 5C4 binds specifically to the surface of platelets but not of leukocytes or red blood cells, as demonstrated using flow cytometry (not shown).

Example 12

FACS measurement of CD62 P externalisation. Human citrate blood was collected from volunteers. Platelet rich plasma (PRP) was generated after centrifugation and washing procedures (PBS 1×; pH 7.2) with 2000 rpm at 4° C. and resuspension. PRP diluted in staining buffer (1×PBS (w/o $Ca^{2+}$ and $Mg^+$) with 0.1% sodium azide and 2% fetal bovine serum (FBS), 2 mM CaCl) was incubated with equine collagen type 1 (0; 2; 5 and 10 µg/ml; Nobis) in the presence of Fc-GPVI-nt (100 µg/ml) or equimolar concentrations control Fc. Anti CD 62P antibodies labelled with the fluorophor peroxidase (Immunotech) were added. FACS measurement was performed with an Becton Dickenson FACScalibur device.

Figure 10:
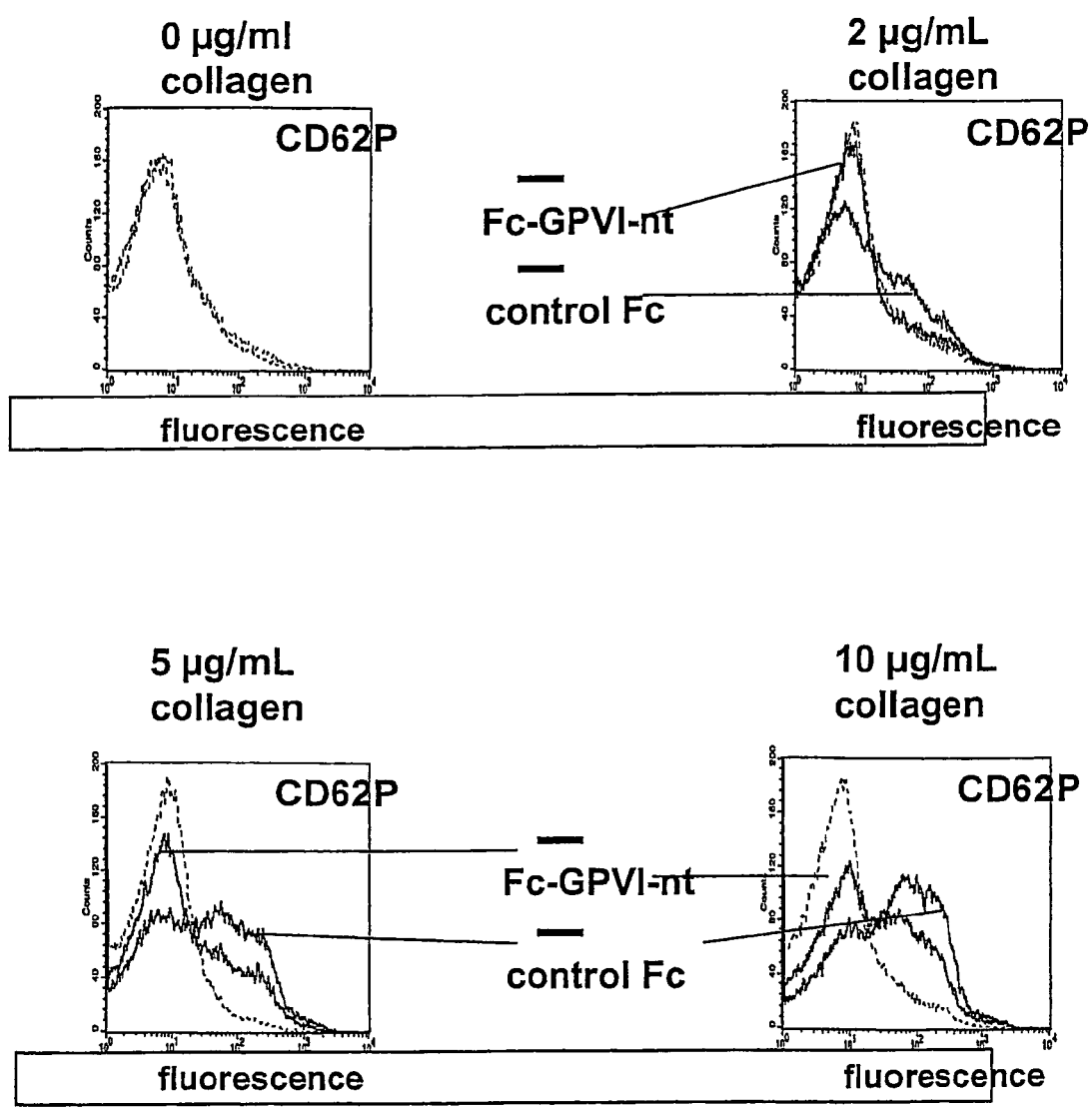
FIG. 10 Fc-GPVI-nt inhibits CD 62 P activation on human platelets as a parameter of release of intracellular transmitter substances from alpha granules by increasing doses of collagen. Human platelets were isolated from whole blood and incubated with anti-CD 62 antibodies labelled with PE (for details see Material and Methods). Fluorescence was determined in a Becton Dickenson FACS device. Representative histogramms are shown. Increasing concentrations of collagen from 0 to 10 µg/ml induced a shift of fluorescence in the presence of the control Fc protein (100 µg/ml; blue line). In the presence of Fc-GPVI-nt (100 µg/ml; red line), the shift of fluorescence and hence CD 62 P activation was markedly inhibited.

Increasing concentrations of collagen led to platelet secretion from alpha granules indicated by CD 62P externalisation. Co-incubation of collagen with Fc-GPVI-nt blunted the CD62 P externalisation determined by FACS (FIG. 10).

Example 13

Platelet aggregation and ATP release. PRP was generated as described above. Aggregation was determined in a Whole-Blood-Aggregometer 500VS (Chrono-Log Corporation). Platelet cell number from PRP was adjusted to $1.0 \times 10^8$ cells/ml by Thyrodes-HEPES buffer (2.5 mmol/l HEPES, 150 mmol/l NaCl, 12 mmol/l NaHCO$_3$, 2,5 mmol/l KCl, 1 mmol/l MgCl$_2$, 2 mmol/l CaCl$_2$, 5,5 mmol D-Glucose, 1 mg/ml BSA, pH 7.4). Chrono-Lume #395 (Chrono-Log Corporation) was added for ATP measurement. Agonists were added to the platelets, pipetted into the aggregometer and aggregation was started under defined stirring conditions. Aggregation was determined by change of light transmission due to coagulating platelets and normalised to an internal standard. ATP release is determined at the characteristic wavelength of Chrono-Lume for ATP and normalised to an internal standard according to the manufacturer's instructions.

Figure 11:
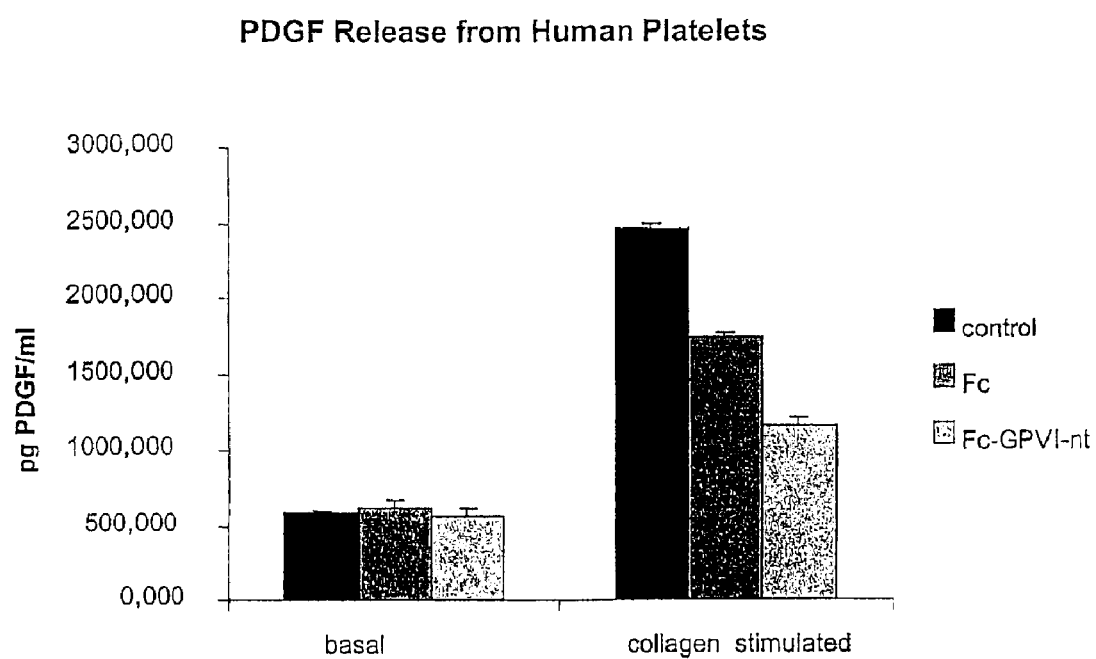
FIG. 11 Specific inhibition of collagen-mediated platelet aggregation and release of endogenous transmitters from dense and alpha granules by Fc-GPVI-nt. (a) Human platelets were incubated with control Fc (80 µg/ml) or Fc-GPVI-nt (80 µg/ml). Aggregation of platelets was induced with collagen (1 µg/ml) or ADP (5 µM) or TRAP (10 µM) and aggregation was determined in an aggregometer under stirring conditions (for details see Material and Methods). Triplet measurements from n=5 different blood donors were carried out. The means±s.e.m are given in % aggregation of the control aggregation without fusion proteins. (b) ATP release was measured simultaneously in the same probes after incubation with control Fc (80 µg/ml) or Fc-GPVI-nt (80 µg/ml). The amount of ATP release is given in % of controls without fusion protein. (c) PDGF release was determined in human platelets with an ELISA system specific for human PDGF under basal conditions and after collagen (20 µg/ml) stimulation (for details see Material and Methods). Preincubation with control Fc had no significant effect on PDGF release from collagen-stimulated platelets, whereas Fc-GPVI-nt (100 µg/ml) reduced the PDGF release significantly. Inhibition of PDGF release did not occur in unstimulated platelets.

Platelet aggregation and ATP release was specifically inhibited by Fc-GPVI-nt for collagen mediated agonist stimulation (FIG. 11a & b). ADP— and thrombin-mediated (TRAP 10 µM) platelet aggregation and ATP release was unaffected by Fc-GPVI-nt.

Example 14

PDGF release from human platelets. PRP from human volunteers was prepared as described above. PDGF release from human platelets was determined with a kit system (R & D Systems # DHD00B) according to the manufacturer's instructions. PDGF release was stimulated with collagen type 1 (20 µg/ml; Nobis) under control conditions and in the presence of Fc-GPVI-nt (100 µg/ml) or equimolar concentrations of control Fc. PDGF release is normalised to the manufacturer's standard probe.

PDGF release as an indicator for release of endogenous transmitters from alpha granules of platelets was also blunted after collagen stimulation. (FIG. 11c).

Example 15

Effect of Fc-GPVI-nt on bleeding time from human whole blood in vitro. In vitro bleeding time was determined with an PFA-100 device (Dade-Behring). 800 µl of human whole blood was injected in the PFA-100 device. Bleeding time was measured with ADP/collagen and epinephrine/collagen coated measuring cells according to the manusfacturer's instructions.

Figure 12:
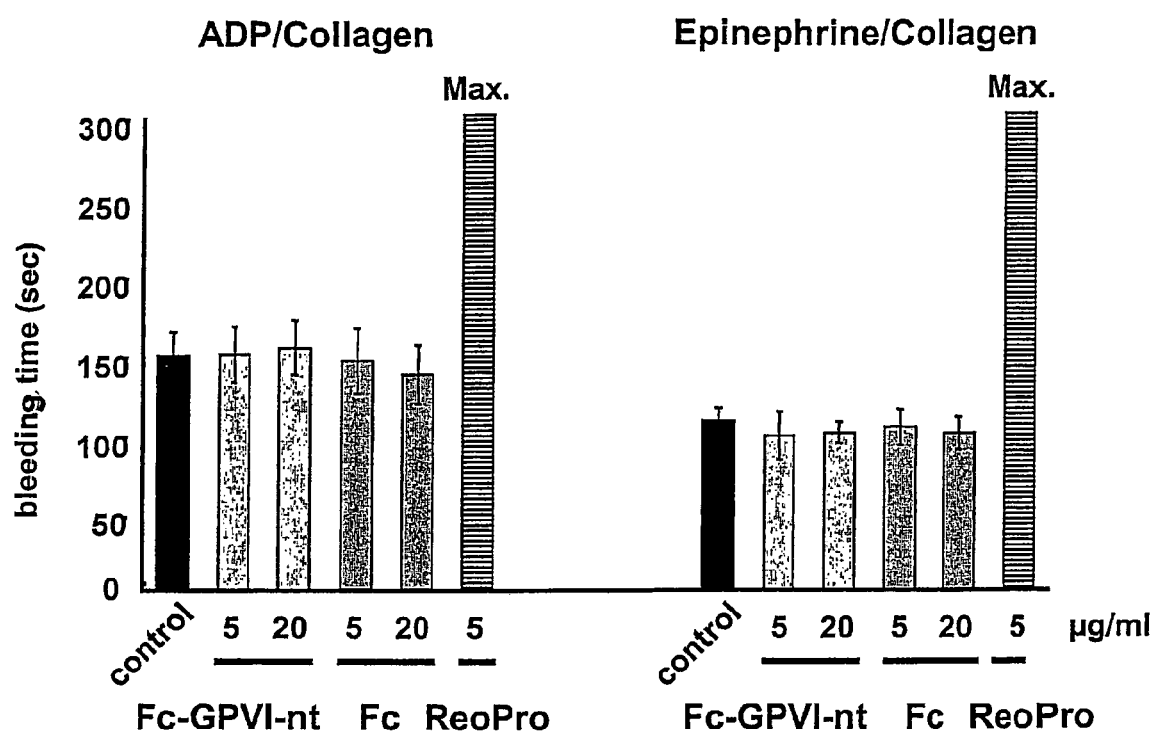
FIG. 12 Fc-GPVI-nt has no significant effect on bleeding time in human blood ex vivo. Bleeding time in human blood was measured ex vivo after ADP/collagen stimulation and epinephrine/collagen stimulation in a PFA-100 device. Fc-GPVI-nt (5 and 20 µg/ml) and Fc (5 and 20 µg/ml) did not prolong bleeding time whereas ReoPro$^R$ in a therapeutically relevant concentration (5 µg/ml) maximally prolonged bleeding time under both conditions. The means±s.e.m. from n=4 blood donors with triplet measurements are summarized.

There was no significant prolongation of bleeding time in vitro (PFA-100 device) with increasing concentrations of Fc-GPVI-nt after different agonist stimulations. In contrast, therapeutically relevant concentrations of ReoPro maximally prolonged bleeding time in the PFA-100 device (FIG. 12).

Example 16

Effect of soluble GPVI on platelet adhesion to immobilized collagen under flow. Human platelets were isolated from ADC-anticoagulated whole blood as described (18). Washed platelets were resuspended in Tyrodes-HEPES buffer (2.5 mmol/l HEPES, 150 mmol/l NaCl, 12 mmol/l NaHCO$_3$, 2,5 mmol/l KCl, 1 mmol/l MgCl$_2$, 2 mmol/l CaCl$_2$, 5,5 mmol D-Glucose, 1 mg/ml BSA, pH 7.4) to obtain a platelet count of $2 \times 10^8$ cells/ml. Adhesion of platelets to plates coated with immobilized collagen was determined in a parallel plate flow chamber in the presence of 200 µg/ml Fc-GPVI-nt or control Fc.

GPVI plays a crucial role in the process of platelet recruitment to immobilized collagen in vitro (22). We determined the effect of Fc-GPVI-nt on adhesion of human platelets to immobilized collagen under shear conditions in vitro. As reported by others earlier (23), platelets adhered firmly to immobilized collagen at both low (500 sec$^{-1}$) and high (1000 sec$^{-1}$) shear rates forming thrombi (FIG. 13). Soluble Fc-GPVI-nt, but not control Fc lacking the external GPVI domain, significantly attenuated platelet adhesion on immobilized collagen by 37 and 44% at shear rates of 500 sec$^{-1}$ and 1000 sec$^{-1}$, respectively (FIG. 13). Inhibition was specific since Fc-GPVI-nt did not affect platelet adhesion to immobilized vWF.

Example 17

Figure 14:
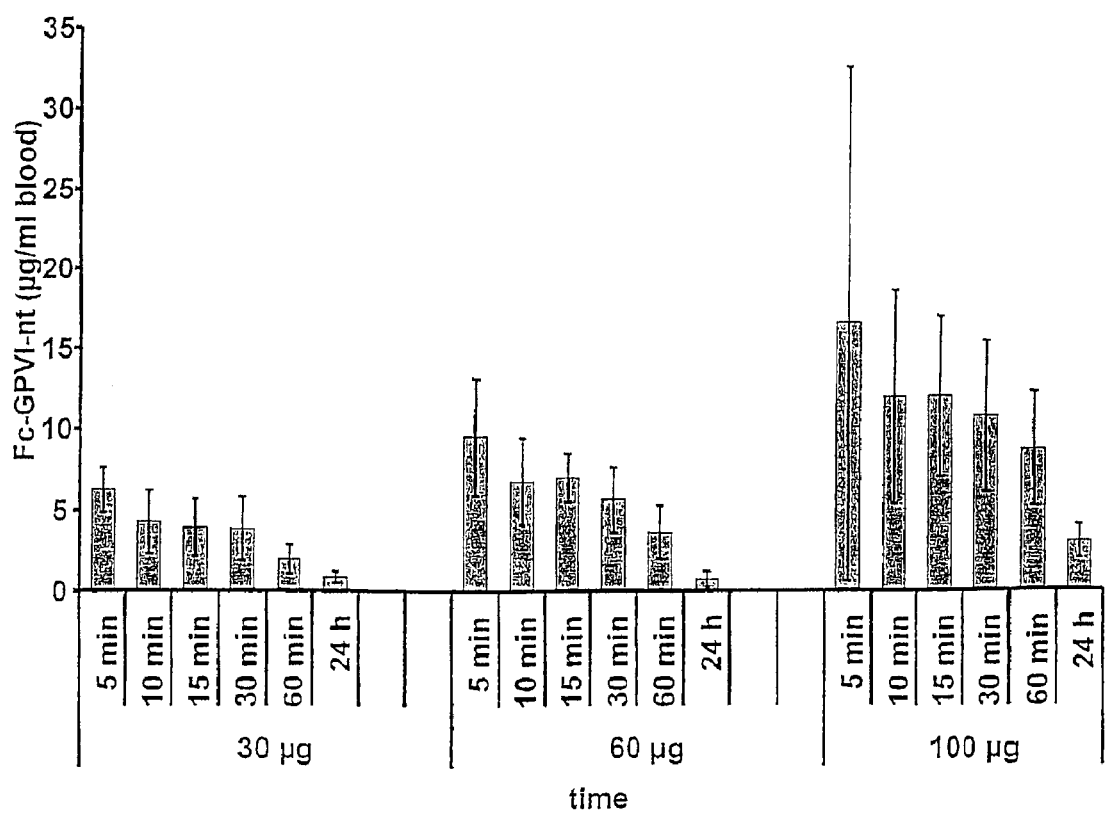
FIG. 14 Fc-GPVI-nt has favourable pharmacokinetics with a prolonged plasma half life after intraperitoneal injection in mice in vivo. Blood concentrations of Fc-GPVI-nt were determined with specific anti-Fc antibodies and ELISA (for details please see "material and methods"). (a) Single intraperitoneal injection of Fc-GPVI-nt (4 µg/g) led to rapid peak blood concentrations of Fc-GPVI-nt after ~24 h with slow decline of Fc-GPVI-nt blood concentrations. The means±s.e.m. from 10 animals are demonstrated. (b) Repeated intraperitoneal applications (10 µg/g; twice weekly) leads to continous accumulation of Fc-GPVI-nt in mice in vivo over 28 days. The means±s.e.m. from 6 animals are demonstrated. (c) Intravenous single dose injection of 30 µg Fc-GPVI-nt (1 µg/g body weight); 60 µg (2 µg/g body weight) and 100 µg Fc-GPVI-nt (3 µg/g body weight) per mouse led to a dose-dependent increase of immunoadhesin plasma concentration. The plasma concentration in the two higher doses in these mice in vivo reached prolonged elevated levels from 5 to 60 minutes and after 24 hours, sufficient for effective collagen scavenging and therefore effective inhibition of GPVI receptor activation on platelets. The means±s.e.m. from 5 animals are demonstrated.

Determination of Fc-GPVI-nt plasma concentrations was carried out with an IMMUNO-TEK ELISA system for the quatitative determination of human IgG (ZeptoMetrix Corporation; Cat # 0801182). Specific peroxidase conjugated goat anti-human IgG antibodies against the Fc part of the Fc-GPVI-nt are used (Dianova). After several washing steps with PBS-T according to the manufacturer's specifications peroxidase substrate (BM Blue POD, Roche) is added and measured at the characteristic 450 nm wavelength in an ELISA assay reader (Tecan Sunrise). The Fc-GPVI-nt concentration is quantified by comparison to an internal human IgG standard. Fc-GPVI-nt showed favourable in vivo pharmacokinetics. After single intraperitoneal injection in mice high plasma levels were measurable after 24 hours and the half life of the fusion protein exceeded 96 hours (FIG. 14a). Repeated intraperitoneal injection was leading to blood accumulation of the fusion protein (FIG. 14b) suggesting favourable kinetics for long term application for the treatment of chronic diseases. After single intravenous injection of Fc-GPVI-nt with increasing doses, dose-dependent plasma concentrations of Fc-GPVI-nt were detectable over 5 to 60 minutes up to 14 hours (FIG. 14c).

Example 18

Preparation of murine platelets for intravital fluorescence microscopy. Murine platelets were isolated from whole blood and labeled with 5-carboxyfluorescein diacetate succinimidyl ester (DCF) as reported earlier (19). The DCF-labeled platelet suspension was adjusted to a final concentration of $200 \times 10^6$ platelets/250 µl. Adhesion of murine platelets was assessed prior to and after carotid injury by in vivo video microscopy, as described below.

Example 19

Carotid ligation and assessment of platelet adhesion and aggregation by intravital microscopy. Platelet recruitment following endothelial denudation was performed as reported earlier (3). In brief, wild type C57BL6/J mice were anesthetized by intraperitoneal injection of a solution of midazolame (5 mg/kg body weight, Ratiopharm, Ulm, Germany), medetomidine (0.5 mg/kg body weight, Pfizer, Karlsruhe, Germany), and fentanyl (0.05 mg/kg body weight, CuraMed Pharma GmbH, Munich, Germany). Where indicated, Fc-GPVI-nt (1 or 2 mg/kg body weight) or control Fc in an amount equimolar to 2 mg/kg Fc-GPVI-nt was administered intravenously. Thereafter, endothelial denudation was induced near the carotid bifurcation by vigorous ligation for 5 min. Following induction of vascular injury luorescent platelets ($200 \times 10^6$/250 µl) were infused intravenously via polyethylene catheters (Portex, Hythe, England) implanted into the right jugular vein. The fluorescent platelets were visualized in situ by in vivo video microscopy of the right common carotid artery using a Zeiss Axiotech microscope (20× water immersion objective, W 20×/0.5, Zeiss) with a 100 W HBO mercury lamp for epi-illumination. All video-taped images were evaluated using a computer-assisted image analysis program (Cap Image 7.4, Dr. Zeintl, Heidelberg, Germany (19;20)). Tethered platelets were defined as all cells establishing initial contact with the vessel wall, followed by slow surface translocation (at a velocity significantly lower than the centerline velocity) or by firm adhesion; their numbers are given as cells per $mm^2$ endothelial surface. The number of adherent platelets was assessed by counting the cells that did not move or detach from the endothelial surface within 10 seconds. The number of platelet aggregates at the site of vascular injury was also quantified and is presented per $mm^2$. In addition, the total thrombus area was assessed using Cap Image 7.4.

Example 20

Scanning electron microscopy. Following intravital videofluorescence microscopy, the carotid artery was perfused with PBS (37° C.) for 1 min in three animals per group, followed by perfusion fixation with phosphate-buffered glutaraldehyde (1% vol/vol). The carotid artery was excised, opened longitudinally, further fixed by immersion in 1% PBS-buffered glutaraldehyde for 12 hours, dehydrated in ethanol, and processed by critical point drying with $CO_2$. Subsequently, the carotid artery specimens were oriented with the lumen exposed, mounted with carbon paint, sputter coated with platinum, and examined using a field emission scanning electron microscope (JSM-6300F, Jeol Ltd., Tokyo, Japan).

Example 21

Assessment of in vivo Fc-GPVI-nt binding by immunohistochemistry. Carotid arteries obtained from mice treated with Fc-GPVI-nt were shock frozen and embedded in cryoblocks (medite, Medizintechnik GmbH, Burgdorf, Germany). The binding of Fc-GPVI-nt to the endothelium and subendothelium was determined on 5 µm cryostat sections, stained with peroxidase-conjugated goat anti-human IgG antibody Fcγ fragment specific (109-035-098; Dianova, Hamburg, Germany). Carotid arteries obtained from Fc-treated mice served as controls.

Example 22

Figure 15:
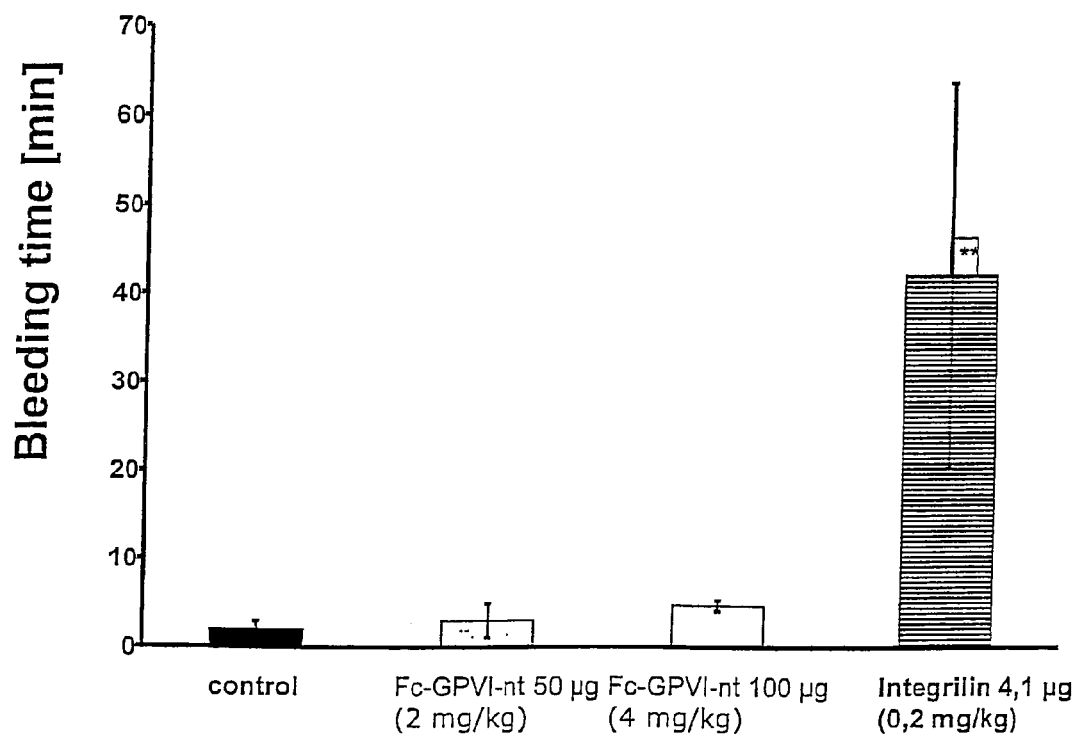
FIG. 15 Effects of Fc-GPVI-nt on platelet adhesion and aggregation in vivo. (a) Mice (n=6 per group) were treated with 2 mg/kg or 4 mg/kg Fc-GPVI-nt iv. Integrilin (0,2 mg/kg)-treated mice served as positive controls (n=8). Bleeding times were determined as described (see "materials and methods"). The Fc-GPVI-nt fusion protein did not increase tail bleeding times compared to control animals. In Integrilin-treated mice tail bleeding time was massively prolonged. **P<0.05 vs. control. (b) Inhibition of GPVI abrogates platelet adhesion and aggregation after vascular injury. Platelet adhesion following vascular injury was determined by intravital video fluorescence microscopy. Mice were pretreated with 1 or 2 mg/kg Fc-GPVI-nt or equimolar amounts of control Fc. The left and right panels summarize platelet tethering and firm platelet adhesion, respectively. Mean±s.e.m., n=5 each group, asterisk indicates significant difference compared to Fc, P<0.05. (c) Effects of Fc-GPVI-nt on thrombus formation following vascular injury in vivo. The number of platelet thrombi (right) and the total thrombus area (left) were assessed by fluorescence microscopy as described. Mean±s.e.m., n=5 each group, asterisk indicates significant difference compared to Fc, P<0.05. (d) The photomicrographs show representative in vivo fluorescence microscopy images illustrating platelet adhesion in the absence or presence of 1 or 2 mg/kg Fc-GPVI-nt or control Fc. Bars represent 50 μm. (e) Scanning electron micrographs of carotid arteries 1 hr after vascular injury in Fc- or Fc-GPVI-nt treated animals. Endothelial denudation induced platelet adhesion and platelet aggregation in Fc-treated mice. In contrast, only very few platelets attached along the damaged vessel wall in Fc-GPVI-nt-treated mice. Subendothelial collagen fibers are visible along the denuded area. Bars represent 10 μm (f) Fc-GPVI-nt specifically binds to the subendothelium of carotid arteries. The binding of Fc-GPVI-nt to the subendothelium was determined on carotid sections, stained with peroxidase-conjugated goat anti-human IgG antibody. Carotid arteries obtained from Fc-treated mice served as controls. Fc-GPVI-nt but not Fc control protein was detected at the subenothelium, as indicated by the brown staining. Original magnification: 100-fold.
Figure 15:

Effect of soluble GPVI on platelet counts, bleeding time and platelet adhesion in vivo. Animals were treated with 2 mg/kg or 4 mg/kg Fc-GPVI-nt or equimolar doses of control Fc lacking the external GPVI domain. Infusion of Fc-GPVI-nt or control Fc even at the highest dose of 4 mg/kg had not significant effects on peripheral platelet counts. Moreover, the Fc-GPVI-nt fusion protein, did not induce any significant prolongation of tail bleeding times compared to control animals (FIG. 15a). The absolute bleeding times were 1.9±0.9 in PBS treated mice and 2.9±1.9 min and 4.6±0.6 min in mice treated with 2 mg/kg or 4 mg/kg Fc-GPVI-nt. In contrast, bleeding times were prolonged condsiderably (42.6±21.6) in Integrilin -treated animals (0.2 mg per kg IV).

The effects of Fc-GPVI-nt on platelet recruitment in a mouse model of carotid injury may be studied using intravital fluorescence microscopy. Animals were treated with 1 mg/kg or 2 mg/kg Fc-GPVI-nt or an equimolar amount of control Fc lacking the external GPVI domain as described above. After infusion of Fc-GPVI-nt or control Fc endothelial denudation of the mouse carotid artery was induced by vigorous ligation as reported previously (3). Ligation of the carotid artery consistently caused complete loss of the endothelial cell layer. Platelet adhesion was directly visualized and quantified using in vivo fluorescence microscopy (19;20) (FIG. 15d). In control (Fc-treated) mice numerous platelets were tethered to the vascular wall within the first minutes after endothelial denudation (12.026±1.115 tethered platelets/$mm^2$). Platelets establishing contact with the subendothelium exhibited initially a slow surface translocation, which is frequently followed by subsequent firm platelet adhesion and platelet aggregation (5.494±874 adherent platelets/$mm^2$ and 114±17 platelet thrombi/$mm^2$). In contrast, in the presence of Fc-GPVI-nt platelet recruitment to the site of vascular injury was dramatically attenuated. Platelet tethering was reduced by 65 and 71% compared to Fc-treated animals following pretreatment with 1 mg/kg or 2 mg/kg Fc-GPVI-nt ($P<0.05$ vs. control). In parallel, firm platelet adhesion was reduced in a dose-dependent manner (by 49 and 65% following administration of 1 mg/kg or 2 mg/kg Fc-GPVI-nt, respectively; $P<0.05$ vs. control). Likewise, aggregation of adherent platelets was virtually absent in animals treated with 2 mg/kg Fc-GPVI-nt fusion protein ($P<0.05$ vs. control Fc, FIG. 15b-d). Scanning electron microscopy also clearly demonstrated that platelet adhesion and aggregation following endothelial denudation of the common carotid artery were virtually absent in Fc-GPVI-nt treated, but not in FC-pretreated mice (FIG. 15e). To confirm the presence of Fc-GPVI-nt at the site of injury, the carotid arteries were excised following in vivo microscopy and processed further for immunohistochemistry using peroxidase-conjugated goat anti-human IgG antibodies. In Fc-GPVI-nt-treated mice Fc-GPVI-nt was detected on at the luminal aspect of the site of vascular damage (FIG. 15f). Together, these data demonstrate that Fc-GPVI-nt specifically binds to sites of vascular injury in vivo and prevents subsequent platelet recruitment.

Effect of soluble GPVI on atherosclerosis. 4 weeks old apoE –/– mice (The Jackson Laboratory) consumed a 0.25% cholesterol diet (Harlan Research diets) for 6 weeks. After 2 weeks 4 apoE –/– mice were injected with Fc-GPVI-nt 200 µg per mouse twice weekly with continous cholesterol diet. 4 apoE –/– mice with the similar protocol were injected with the control Fc protein (200 µg) twice weekly and served as control mice. For assessment of plaque formation the animals were killed and the vascular tree was carefully dissected from the animals. The whole preparations of the aortae and carotides were flushed with 0.9% sodium chloride and fixed. The complete vascular preparation was stained with SUDAN III red to assess plaque formation and viewed under a microscope. Treatment of atherosclerosis prone apoE −/− knockout mice with Fc-GPVI-nt over 4 weeks significantly attenuated atheroprogression. (FIG. 16).

Example 23

FACS measurement of CD61 and CD32 surface expression on platelets from diabetic patients. Human citrate blood was collected from 111 patients suffering from diabetes or from 363 non-diabetic patients. Platelet rich plasma (PRP) was generated after centrifugation and washing procedures (PBS 1×, pH 7.2) with 2000 rpm at 4° C. and resuspension. Anti CD61 and anti CD32 antibodies labelled with the fluorophor peroxidase (Immunotech) were added or or the anti monoclonal anti-GPVI antibody 4C9 labelled with FITC. FACS measurement was performed with an Becton Dickenson FACScalibur device. Surface expression was quantified by fluorescence. Correleation of CD32 fluorescence and 4C9 fluorescence was calculated with the correlation coefficient r=0.516.

Statistical Analysis. Comparisons between group means were performed using Mann-Whitney Rank Sum Test. Data represent mean±s.e.m. A value of P<0.05 was regarded as significant.

Reference List

1. Baumgartner, H. R. 1977. Platelet interaction with collagen fibrils in flowing blood. I. Reaction of human platelets with alpha chymotrypsin-digested subendothelium. *Thromb Haenmost* 37:1-16.
2. Clemetson, K. J. and Clemetson, J. M. 2001. Platelet collagen receptors. *Thromb. Haemost.* 86:189-197.
3. Massberg, S., Gawaz, M., Gruner, S., Schulte, V., Konrad, I., Zohlnhöfer, D., Heinzmann, U., and Nieswandt, B. 2003. A crucial role of glycoprotein VI for platelet recruitment to the injured arterial wall in vivo. *J. Exp. Med.* 197:41-49.
4. Moroi, M., Jung, S. M., Okuma, M., and Shinmyozu, K. 1989. A patient with platelets deficient in glycoprotein VI that lack both collagen-induced aggregation and adhesion. *J. Clin. Invest* 84:1440-1445.
5. Clemetson, J. M., Polgar, J., Magnenat, E., Wells, T. N., and Clemetson, K. J. 1999. The platelet collagen receptor glycoprotein VI is a member of the immunoglobulin superfamily closely related to FcalphaR and the natural killer receptors. *J Bio. Chem.* 274:29019-29024.
6. Jandrot-Perrus, M., Busfield, S., Lagrue, A. H., Xiong, X., Debili, N., Chickering, T., Le Couedic, J. P., Goodearl, A., Dussault, B., Fraser, C. et al. 2000. Cloning, characterization, and functional studies of human and mouse glycoprotein VI: a platelet-specific collagen receptor from the immunoglobulin superfamily. *Blood* 96:1798-1807.
7. Gibbins, J. M., Okuma, M., Famdale, R., Barnes, M., and Watson, S. P. 1997. Glycoprotein VI is the collagen receptor in platelets which underlies tyrosine phosphorylation of the Fc receptor gamma-chain. *FEBS Lett.* 413:255-259.
8. Zheng, Y. M., Liu, C., Chen, H., Locke, D., Ryan, J. C., and Kahn, M. L. 2001. Expression of the platelet receptor GPVI confers signaling via the Fc receptor gamma -chain in response to the snake venom convulxin but not to collagen. *J. Biol. Chem.* 276:12999-13006.
9. Suzuki-Inoue, K., Tulasne, D., Shen, Y., Bori-Sanz, T., Inoue, O., Jung, S. M., Moroi, M., Andrews, R. K., Berndt, M. C., and Watson, S. P. 2002. Association of Fyn and Lyn with the proline rich domain of GPVI regulates intracellular signalling. *J. Biol. Chem.*
10. Barnes, M. J., Knight, C. G., and Famdale, R. W. 1998. The collagen-platelet interaction. *Curr. Opin. Hematol.* 5:314-320.
11. Falet, H., Barkalow, K. L., Pivniouk, V. I., Barnes, M. J., Geha, R. S., and Hartwig, J. H. 2000. Roles of SLP-76, phosphoinositide 3-kinase, and gelsolin in the platelet shape changes initiated by the collagen receptor GPVI/FcR gamma-chain complex. *Blood* 96:3786-3792.
12. Pasquet, J. M., Gross, B., Quek, L., Asazuma, N., Zhang, W., Sommers, C. L., Schweighoffer, E., Tybulewicz, V., Judd, B., Lee, J. R. et al. 1999. LAT is required for tyrosine phosphorylation of phospholipase cgamma2 and platelet activation by the collagen receptor GPVI. *Mol. Cell Biol.* 19:8326-8334.
13. Berlanga, O., Tulasne, D., Bori, T., Snell, D. C., Miura, Y., Jung, S., Moroi, M., Frampton, J., and Watson, S. P. 2002. The Fc receptor gammachain is necessary and sufficient to initiate signalling through glycoprotein VI in transfected cells by the snake C-type lectin, convuixin. *Eur. J. Biochem.* 269:2951-2960.
14. Sugiyama, T., Okuma, M., Ushikubi, F., Sensaki, S., Kanaji, K., and Uchino, H. 1987. A novel platelet aggregating factor found in a patient with defective collagen-induced platelet aggregation and autoimmune thrombocytopenia. *Blood* 69:1712-1720.
15. Sugiyama, T., Ishibashi, T., and Okuma, M. 1993. Functional role of the antigen recognized by an antiplatelet antibody specific for a putative collagen receptor in platelet-collagen interaction. *Inf. J. Hematol.* 58:99-104.
16. Schulte, V., Snell, D., Bergmeier, W., Zirngibl, H., Watson, S. P., and Nieswandt, B. 2001. Evidence for two distinct epitopes within collagen for activation of murine platelets. *J. Biol. Chem;* 276:36-368.
17. Kremmer, E., Kranz, B. R., Hille, A., Klein, K., Eulitz, M., Hoffmann-Fezer, G., Feiden, W., Herrmann, K., Delecluse, H. J., Delsol, G. et al. 1995. Rat monoclonal antibodies differentiating between the Epstein-Barr virus nuclear antigens 2A (EBNA2A) and 2B (EBNA2B). *Virology* 208: 336-342.
18. Dickfeld, T., Lengyel, E., May, A. E., Massberg, S., Brand, K., Page, S., Thielen, C., Langenbrink, K., and Gawaz, M. 2001. Transient interaction of activated platelets with endothelial cells induces expression of monocyte-chemoattractant protein-1 via a p38 mitogen-activated protein kinase mediated pathway. Implications for atherogenesis. *Cardiovasc. Res.* 49:189-199.
19. Massberg, S., Enders, G., Leiderer, R., Eisenmenger, S., Vestweber, D., Krombach, F., and Messmer, K. 1998. Platelet-endothelial cell interactions during ischemia/reperfusion: the role of P-selectin. *Blood* 92:507-515.
20. Massberg, S., Enders, G., Matos, F. C., Tomic, L. I., Leiderer, R., Eisenmenger, S., Messmer, K., and Krombach, F. 1999. Fibrinogen deposition at the postischemic vessel wall promotes platelet adhesion during ischemia-reperfusion in vivo. *Blood* 94:3829-3838.
21. Miura, Y., Takahashi, T., Jung, S. M., and Moroi, M. 2002. Analysis of the interaction of platelet collagen receptor glycoprotein VI (GPVI) with collagen. A dimeric form of GPVI, but not the monomeric form, shows affinity to fibrous collagen. *J. Biol. Chem.* 277:46197-46204.
22. Chen, H., Locke, D., Liu, Y., Liu, C., and Kahn, M. L. 2002. The platelet receptor GPVI mediates both adhesion and signaling responses to collagen in a receptor density-dependent fashion. *J. Biol. Chem.* 277:3011-3019.

23. Savage, B., Almus-Jacobs, F., and Ruggeri, Z. M. 1998. Specific synergy of multiple substrate-receptor interactions in platelet thrombus formation under flow. *Cell* 94:657-666.
24. van Zanten, G. H., de Graaf, S., Slootweg, P. J., Heijnen, H. F., Connolly, T. M., de Groot, P. G., and Sixma, J. J. 1994. Increased platelet deposition on atherosclerotic coronary arteries. *J. Clin. Invest* 93:615-632.
25. Baumgartner, H. R., Muggli, R., Tschopp, T. B., and Turifto, V. T. 1976. Platelet adhesion, release and aggregation in flowing blood: effects of surface properties and platelet function. *Thromb. Haemost.* 35:124-138.
27. Jandrot-Perrus, M., Lagrue, A. H., Okuma, M., and Bon, C. 1997. Adhesion and activation of human platelets induced by convulxin involve glycoprotein VI and integrin alpha2beta1. *J Bio. Chem.* 272:27035-27041.
28. Rekhter, M. D. 1999. Collagen synthesis in atherosclerosis: too much and not enough. *Cardiovasc. Res.* 41:376-384.
29. Ruggeri, Z. M. 1997. Mechanisms initiating platelet thrombus formation. *Thromb. Haemost.* 78:611-616.
30. Goto, S., Ikeda, Y., Saldivar, E., and Ruggeri, Z. M. 1998. Distinct mechanisms of platelet aggregation as a consequence of different shearing flow conditions. *J. Clin. Invest.* 101:479-486.
31. Sixma, J. J., van Zanten, G. H., Banga, J. D., Nieuwenhuls, H. K., and de Groot, P. G. 1995. Platelet adhesion. *Semin. Hematol* 32:89-98.
32. Nieswandt, B., Schulte, V., Bergmeier, W., Mokhtari-Nejad, R., Rackebrandt, K., Cazenave, J. P., Ohlmann, P., Gachet, C., and Zimgibl, H. 2001. Long-term antithrombotic protection by in vivo depletion of platelet glycoprotein VI in mice. *J Exp Med* 193:459-469.
33. Lincoff, A. M., Califf, R. M., and Topol, E. J. 2000. Platelet glycoprotein IIb/IIIa receptor blockade in coronary artery disease. *J. Am. Coll. Cardiol.* 35:1103-1115.
34. Neumann, F. J. and Schomig, A. 1998. Glycoprotein IIb/IIIa receptor blockade with coronary stent placement. *Semin. Interv. Cardiol.* 3:81-90.
35. Bertrand, M. E., Rupprecht, H. J., Urban, P., Gershlick, A. H., and Investigators, f. 2000. Double-blind study of the safety of clopidogrel with and without a loading dose in combination with aspirin compared with ticlopidine in combination with aspirin after coronary stenting: the clopidogrel aspirin stent international cooperative study (CLASSICS). *Circulation* 102:624-629.
36. Foster, R. H. and Wiseman, L. R. 1998. Abciximab. An updated review of its use in ischaemic heart disease. *Drugs* 56:629-665.
37. Arai, M., Yamamoto, N., Moroi, M., Akamatsu, N., Fukutake, K., and Tanoue, K. 1995. Platelets with 10% of the normal amount of glycoprotein VI have an impaired response to collagen that results in a mild bleeding tendency. *Br. J Haematol.* 89:124-130.

---

The invention claimed is:

1. A recombinant nucleic acid molecule comprising the nucleic acid sequence of SEQ ID NO: 2 or a variant thereof that codes for the same polypeptide according to the degeneracy of the genetic code,
   wherein the polypeptide encoded by the nucleic acid is secreted from a cell in a form functional for binding to collagen.

2. The recombinant nucleic acid molecule according to claim 1, wherein said nucleic acid molecule consists of the nucleic acid sequence of SEQ ID NO: 2.

3. A recombinant nucleic acid molecule encoding a polypeptide comprising the amino acid sequence of SEQ ID NO: 1.

4. A vector comprising the nucleic acid according to claim 1.

5. An isolated host cell comprising the vector of claim 4.

6. An isolated host cell comprising a vector, wherein the vector comprises the nucleic acid of claim 3.

7. A method for producing a polypeptide, comprising:
   culturing the host cell of claim 5 under conditions in which the nucleic acid molecule is expressed, thereby producing the polypeptide.

8. A method for producing a polypeptide comprising culturing a host cell which comprises the nucleic acid molecule of claim 1, under conditions in which the nucleic acid sequence is expressed.

9. A method for producing a polypeptide comprising culturing a host cell which comprises the nucleic acid molecule of claim 2, under conditions in which the nucleic acid sequence is expressed.

10. A method for producing a polypeptide comprising culturing a host cell which comprises the nucleic acid molecule of claim 3, under conditions in which the nucleic acid sequence is expressed.

11. A method for producing a dimeric fusion protein comprising: culturing a host cell which comprises a nucleic acid molecule comprising the nucleic acid sequence of SEQ ID NO: 2 or a variant thereof that codes for the same polypeptide according to the degeneracy of the genetic code under conditions in which the nucleic acid sequence is expressed and the fusion protein is produced as a dimer under non-reducing conditions.

* * * * *

```
SEQUENCE LISTING

<160> NUMBER OF SEQ ID NOS: 2

<210> SEQ ID NO 1
<211> LENGTH: 504
<212> TYPE: PRT
<213> ORGANISM: Artificial
<220> FEATURE:
<223> OTHER INFORMATION: Fc-GPVI-nt amino acid sequence

<400> SEQUENCE: 1

Met Ser Pro Ser Pro Thr Ala Leu Phe Cys Leu Gly Leu Cys Leu Gly
1               5                   10                  15

Arg Val Pro Ala Gln Ser Gly Pro Leu Pro Lys Pro Ser Leu Gln Ala
            20                  25                  30

Leu Pro Ser Ser Leu Val Pro Leu Glu Lys Pro Val Thr Leu Arg Cys
        35                  40                  45

Gln Gly Pro Pro Gly Val Asp Leu Tyr Arg Leu Glu Lys Leu Ser Ser
    50                  55                  60

Ser Arg Tyr Gln Asp Gln Ala Val Leu Phe Ile Pro Ala Met Lys Arg
65                  70                  75                  80

Ser Leu Ala Gly Arg Tyr Arg Cys Ser Tyr Gln Asn Gly Ser Leu Trp
                85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
    130                 135                 140

Leu Tyr Lys Glu Gly Asp Pro Ala Pro Tyr Lys Asn Pro Glu Arg Trp
145                 150                 155                 160
```

```
Tyr Arg Ala Ser Phe Pro Ile Ile Thr Val Thr Ala Ala His Ser Gly
            165                 170                 175

Thr Tyr Arg Cys Tyr Ser Phe Ser Ser Arg Asp Pro Tyr Leu Trp Ser
            180                 185                 190

Ala Pro Ser Asp Pro Leu Glu Leu Val Val Thr Gly Thr Ser Val Thr
            195                 200                 205

Pro Ser Arg Leu Pro Thr Glu Pro Pro Ser Ser Val Ala Glu Phe Ser
            210                 215                 220

Glu Ala Thr Ala Glu Leu Thr Val Ser Phe Thr Asn Lys Val Phe Thr
225                 230                 235                 240

Thr Glu Thr Ser Arg Ser Ile Thr Thr Ser Pro Lys Glu Ser Asp Ser
                245                 250                 255

Pro Ala Gly Pro Ala Arg Gln Tyr Tyr Thr Lys Gly Asn Gly Gly Arg
            260                 265                 270

Glu Ser Lys Ser Cys Asp Lys Thr His Thr Cys Pro Pro Cys Pro Ala
            275                 280                 285

Pro Glu Leu Leu Gly Gly Pro Ser Val Phe Leu Phe Pro Pro Lys Pro
            290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
            355                 360                 365

Asp Trp Leu Asn Gly Lys Glu Tyr Lys Cys Lys Val Ser Asn Lys Ala
370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Asp Glu Leu Thr
                405                 410                 415

Lys Asn Gln Val Ser Leu Thr Cys Leu Val Lys Gly Phe Tyr Pro Ser
            420                 425                 430

Asp Ile Ala Val Glu Trp Glu Ser Asn Gly Gln Pro Glu Asn Asn Tyr
            435                 440                 445

Lys Thr Thr Pro Pro Val Leu Asp Ser Asp Gly Ser Phe Phe Leu Tyr
450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
            500

<210> SEQ ID NO 2
<211> LENGTH: 1515
<212> TYPE: DNA
<213> ORGANISM: Artificial
<220> FEATURE:
<223> OTHER INFORMATION: Fc-GPVI-nt nucleotide sequence

<400> SEQUENCE: 2
atgtctccat ccccgaccgc cctcttctgt cttgggctgt gtctggggcg tgtgccagcg      60
```

```
cagagtggac cgctccccaa gccctccctc caggctctgc ccagctccct ggtgcccctg    120
gagaagccag tgaccctccg gtgccaggga cctccgggcg tggacctgta ccgcctggag    180
aagctgagtt ccagcaggta ccaggatcag gcagtcctct tcatcccggc catgaagaga    240
agtctggctg gacgctaccg ctgctcctac cagaacggaa gcctctggtc cctgcccagc    300
gaccagctgg agctcgttgc cacgggagtt tttgccaaac cctcgctctc agcccagccc    360
ggcccggcgg tgtcgtcagg aggggacgta accctacagt gtcagactcg gtatggcttt    420
gaccaatttg ctctgtacaa ggaaggggac cctgcgccct acaagaatcc cgagagatgg    480
taccgggcta gtttccccat catcacggtg accgccgccc acagcggaac ctaccgatgc    540
tacagcttct ccagcaggga cccatacctg tggtcggccc ccagcgaccc cctggagctt    600
gtggtcacag gaacctctgt gacccccagc cggttaccaa cagaaccacc ttcctcggta    660
gcagaattct cagaagccac cgctgaactg accgtctcat tcacaaacaa agtcttcaca    720
actgagactt ctaggagtat caccaccagt ccaaaggagt cagactctcc agctggtcct    780
gcccgccagt actacaccaa gggcaacggc ggccgcgagt ccaaatcttg tgacaaaact    840
cacacatgcc caccgtgccc agcacctgaa ctcctggggg gaccgtcagt cttcctcttc    900
cccccaaaac ccaaggacac cctcatgatc tcccggaccc ctgaggtcac atgcgtggtg    960
gtggacgtga gccacgaaga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggagtacaa gtgcaaggtc   1140
tccaacaaag ccctcccagc ccccatcgag aaaaccatct ccaaagccaa agggcagccc   1200
cgagagccac aggtgtacac cctgcccca tcccgggatg agctgaccaa gaaccaggtc   1260
agcctgacct gcctggtcaa aggcttctat cccagcgaca tcgccgtgga gtgggagagc   1320
aatgggcagc cggagaacaa ctacaagacc acgcctcccg tgctggactc cgacggctcc   1380
ttcttcctct acagcaagct caccgtggac aagagcaggt ggcagcaggg gaacgtcttc   1440
tcatgctccg tgatgcatga ggctctgcac aaccactaca cgcagaagag cctctccctg   1500
tctccgggta aatga                                                    1515
```